(12) United States Patent
Flynn et al.

(10) Patent No.: US 8,921,565 B2
(45) Date of Patent: Dec. 30, 2014

(54) PYRIDONE AMIDES AND ANALOGS EXHIBITING ANTI-CANCER AND ANTI-PROLIFERATIVE ACTIVITIES

(71) Applicants: Daniel L. Flynn, Lawrence, KS (US); Michael D. Kaufman, Lawrence, KS (US)

(72) Inventors: Daniel L. Flynn, Lawrence, KS (US); Michael D. Kaufman, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 13/683,277

(22) Filed: Nov. 21, 2012

(65) Prior Publication Data
US 2013/0317066 A1    Nov. 28, 2013

Related U.S. Application Data

(60) Provisional application No. 61/562,602, filed on Nov. 22, 2011.

(51) Int. Cl.
*C07D 213/82* (2006.01)
*A61K 31/444* (2006.01)

(52) U.S. Cl.
CPC ............ *C07D 213/82* (2013.01); *A61K 31/444* (2013.01)

USPC .......................................... 546/261; 514/335

(58) Field of Classification Search
CPC ..................................................... C07D 213/82
See application file for complete search history.

(56) References Cited

FOREIGN PATENT DOCUMENTS

WO    WO 2008/058229 A1  *  5/2008

* cited by examiner

*Primary Examiner* — James D Anderson
(74) *Attorney, Agent, or Firm* — Cooley LLP

(57) ABSTRACT

Compounds useful in the treatment of mammalian cancers and especially human cancers according to Formula I are disclosed.

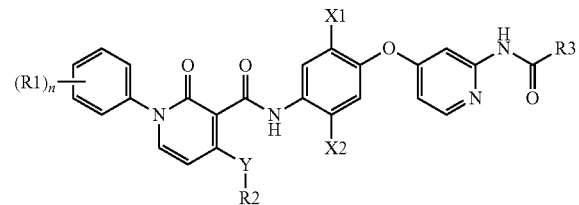

Formula I

Pharmaceutical compositions and methods of treatment employing the compounds disclosed herein are also disclosed.

23 Claims, No Drawings

SEQUENCE LISTING

```
<160> NUMBER OF SEQ ID NOS: 4

<210> SEQ ID NO 1
<211> LENGTH: 676
<212> TYPE: PRT
<213> ORGANISM: Artificial Sequence
<220> FEATURE:
<223> OTHER INFORMATION: c-KIT with N-terminal CST fusion

<400> SEQUENCE: 1

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
                20                  25                  30

Glu Gly Asp Lys Trp Arg Asn Lys Lys Phe Glu Leu Gly Leu Glu Phe
            35                  40                  45

Pro Asn Leu Pro Tyr Tyr Ile Asp Gly Asp Val Lys Leu Thr Gln Ser
    50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
            100                 105                 110

Leu Lys Val Asp Phe Leu Ser Lys Leu Pro Glu Met Leu Lys Met Phe
        115                 120                 125

Glu Asp Arg Leu Cys His Lys Thr Tyr Leu Asn Gly Asp His Val Thr
    130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
        195                 200                 205

His Pro Pro Lys Ser Asp Leu Val Pro Arg His Asn Gln Thr Ser Leu
    210                 215                 220

Tyr Lys Lys Ala Gly Ser Ala Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
```

```
              260             265             270
Pro Thr Gln Leu Pro Tyr Asp His Lys Trp Glu Phe Pro Arg Asn Arg
            275             280             285

Leu Ser Phe Gly Lys Thr Leu Gly Ala Gly Ala Phe Gly Lys Val Val
290             295             300

Glu Ala Thr Ala Tyr Gly Leu Ile Lys Ser Asp Ala Ala Met Thr Val
305             310             315             320

Ala Val Lys Met Leu Lys Pro Ser Ala His Leu Thr Glu Arg Glu Ala
            325             330             335

Leu Met Ser Glu Leu Lys Val Leu Ser Tyr Leu Gly Asn His Met Asn
            340             345             350

Ile Val Asn Leu Leu Gly Ala Cys Thr Ile Gly Gly Pro Thr Leu Val
            355             360             365

Ile Thr Glu Tyr Cys Cys Tyr Gly Asp Leu Leu Asn Phe Leu Arg Arg
            370             375             380

Lys Arg Asp Ser Phe Ile Cys Ser Lys Gln Glu Asp His Ala Glu Ala
385             390             395             400

Ala Leu Tyr Lys Asn Leu Leu His Ser Lys Glu Ser Ser Cys Ser Asp
            405             410             415

Ser Thr Asn Glu Tyr Met Asp Met Lys Pro Gly Val Ser Tyr Val Val
            420             425             430

Pro Thr Lys Ala Asp Lys Arg Arg Ser Val Arg Ile Gly Ser Tyr Ile
            435             440             445

Glu Arg Asp Val Thr Pro Ala Ile Met Glu Asp Asp Glu Leu Ala Leu
            450             455             460

Asp Leu Glu Asp Leu Leu Ser Phe Ser Tyr Gln Val Ala Lys Gly Met
465             470             475             480

Ala Phe Leu Ala Ser Lys Asn Cys Ile His Arg Asp Leu Ala Ala Arg
            485             490             495

Asn Ile Leu Leu Thr His Gly Arg Ile Thr Lys Ile Cys Asp Phe Gly
            500             505             510

Leu Ala Arg Asp Ile Lys Asn Asp Ser Asn Tyr Val Val Lys Gly Asn
            515             520             525

Ala Arg Leu Pro Val Lys Trp Met Ala Pro Glu Ser Ile Phe Asn Cys
            530             535             540

Val Tyr Thr Phe Glu Ser Asp Val Trp Ser Tyr Gly Ile Phe Leu Trp
545             550             555             560

Glu Leu Phe Ser Leu Gly Ser Ser Pro Tyr Pro Gly Met Pro Val Asp
            565             570             575

Ser Lys Phe Tyr Lys Met Ile Lys Glu Gly Phe Arg Met Leu Ser Pro
            580             585             590

Glu His Ala Pro Ala Glu Met Tyr Asp Ile Met Lys Thr Cys Trp Asp
            595             600             605

Ala Asp Pro Leu Lys Arg Pro Thr Phe Lys Gln Ile Val Gln Leu Ile
            610             615             620

Glu Lys Gln Ile Ser Glu Ser Thr Asn His Ile Tyr Ser Asn Leu Ala
625             630             635             640

Asn Cys Ser Pro Asn Arg Gln Lys Pro Val Val Asp His Ser Val Arg
            645             650             655

Ile Asn Ser Val Gly Ser Thr Ala Ser Ser Ser Gln Pro Leu Leu Val
            660             665             670

His Asp Asp Val
            675
```

```
<210> SEQ ID NO 2
<211> LENGTH: 474
<212> TYPE: PRT
<213> ORGANISM: Unknown
<220> FEATURE:
<223> OTHER INFORMATION: c-MET kinase

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Leu Val Pro Arg Gly Ser
            20                  25                  30

Pro Trp Ile Pro Phe Thr Met Lys Lys Arg Lys Gln Ile Lys Asp Leu
        35                  40                  45

Gly Ser Glu Leu Val Arg Tyr Asp Ala Arg Val His Thr Pro His Leu
    50                  55                  60

Asp Arg Leu Val Ser Ala Arg Ser Val Ser Pro Thr Thr Glu Met Val
65                  70                  75                  80

Ser Asn Glu Ser Val Asp Tyr Arg Ala Thr Phe Pro Glu Asp Gln Phe
                85                  90                  95

Pro Asn Ser Ser Gln Asn Gly Ser Cys Arg Gln Val Gln Tyr Pro Leu
            100                 105                 110

Thr Asp Met Ser Pro Ile Leu Thr Ser Gly Asp Ser Asp Ile Ser Ser
        115                 120                 125

Pro Leu Leu Gln Asn Thr Val His Ile Asp Leu Ser Ala Leu Asn Pro
    130                 135                 140

Glu Leu Val Gln Ala Val Gln His Val Val Ile Gly Pro Ser Ser Leu
145                 150                 155                 160

Ile Val His Phe Asn Glu Val Ile Gly Arg Gly His Phe Gly Cys Val
                165                 170                 175

Tyr His Gly Thr Leu Leu Asp Asn Asp Gly Lys Lys Ile His Cys Ala
            180                 185                 190

Val Lys Ser Leu Asn Arg Ile Thr Asp Ile Gly Glu Val Ser Gln Phe
        195                 200                 205

Leu Thr Glu Gly Ile Ile Met Lys Asp Phe Ser His Pro Asn Val Leu
    210                 215                 220

Ser Leu Leu Gly Ile Cys Leu Arg Ser Glu Gly Ser Pro Leu Val Val
225                 230                 235                 240

Leu Pro Tyr Met Lys His Gly Asp Leu Arg Asn Phe Ile Arg Asn Glu
                245                 250                 255

Thr His Asn Pro Thr Val Lys Asp Leu Ile Gly Phe Gly Leu Gln Val
            260                 265                 270

Ala Lys Gly Met Lys Tyr Leu Ala Ser Lys Lys Phe Val His Arg Asp
        275                 280                 285

Leu Ala Ala Arg Asn Cys Met Leu Asp Glu Lys Phe Thr Val Lys Val
    290                 295                 300

Ala Asp Phe Gly Leu Ala Arg Asp Met Tyr Asp Lys Glu Tyr Tyr Ser
305                 310                 315                 320

Val His Asn Lys Thr Gly Ala Lys Leu Pro Val Lys Trp Met Ala Leu
                325                 330                 335

Glu Ser Leu Gln Thr Gln Lys Phe Thr Thr Lys Ser Asp Val Trp Ser
            340                 345                 350

Phe Gly Val Leu Leu Trp Glu Leu Met Thr Arg Gly Ala Pro Pro Tyr
        355                 360                 365
```

```
Pro Asp Val Asn Thr Phe Asp Ile Thr Val Tyr Leu Leu Gln Gly Arg
    370                 375                 380

Arg Leu Leu Gln Pro Glu Tyr Cys Pro Asp Pro Leu Tyr Glu Val Met
385                 390                 395                 400

Leu Lys Cys Trp His Pro Lys Ala Glu Met Arg Pro Ser Phe Ser Glu
            405                 410                 415

Leu Val Ser Arg Ile Ser Ala Ile Phe Ser Thr Phe Ile Gly Glu His
            420                 425                 430

Tyr Val His Val Asn Ala Thr Tyr Val Asn Val Lys Cys Val Ala Pro
        435                 440                 445

Tyr Pro Ser Leu Leu Ser Ser Glu Asp Asn Ala Asp Asp Glu Val Asp
    450                 455                 460

Thr Arg Pro Ala Ser Phe Trp Glu Thr Ser
465                 470
```

<210> SEQ ID NO 3
<211> LENGTH: 315
<212> TYPE: PRT
<213> ORGANISM: Unknown
<220> FEATURE:
<223> OTHER INFORMATION: KDR protein sequence used for screening

<400> SEQUENCE: 3

```
Asp Pro Asp Glu Leu Pro Leu Asp Glu His Cys Glu Arg Leu Pro Tyr
1               5                   10                  15

Asp Ala Ser Lys Trp Glu Phe Pro Arg Asp Arg Leu Lys Leu Gly Lys
            20                  25                  30

Pro Leu Gly Arg Gly Ala Phe Gly Gln Val Ile Glu Ala Asp Ala Phe
        35                  40                  45

Gly Ile Asp Lys Thr Ala Thr Cys Arg Thr Val Ala Val Lys Met Leu
    50                  55                  60

Lys Glu Gly Ala Thr His Ser Glu His Arg Ala Leu Met Ser Glu Leu
65                  70                  75                  80

Lys Ile Leu Ile His Ile Gly His His Leu Asn Val Val Asn Leu Leu
                85                  90                  95

Gly Ala Cys Thr Lys Pro Gly Gly Pro Leu Met Val Ile Val Glu Phe
            100                 105                 110

Cys Lys Phe Gly Asn Leu Ser Thr Tyr Leu Arg Ser Lys Arg Asn Glu
        115                 120                 125

Phe Val Pro Tyr Lys Val Ala Pro Glu Asp Leu Tyr Lys Asp Phe Leu
    130                 135                 140

Thr Leu Glu His Leu Ile Cys Tyr Ser Phe Gln Val Ala Lys Gly Met
145                 150                 155                 160

Glu Phe Leu Ala Ser Arg Lys Cys Ile His Arg Asp Leu Ala Ala Arg
                165                 170                 175

Asn Ile Leu Leu Ser Glu Lys Asn Val Val Lys Ile Cys Asp Phe Gly
            180                 185                 190

Leu Ala Arg Asp Ile Tyr Lys Asp Pro Asp Tyr Val Arg Lys Gly Asp
        195                 200                 205

Ala Arg Leu Pro Leu Lys Trp Met Ala Pro Glu Thr Ile Phe Asp Arg
    210                 215                 220

Val Tyr Thr Ile Gln Ser Asp Val Trp Ser Phe Gly Val Leu Leu Trp
225                 230                 235                 240

Glu Ile Phe Ser Leu Gly Ala Ser Pro Tyr Pro Gly Val Lys Ile Asp
                245                 250                 255
```

```
Glu Phe Cys Arg Arg Leu Lys Glu Gly Thr Arg Met Arg Ala Pro
            260                 265                 270

Asp Tyr Thr Thr Pro Glu Met Tyr Gln Thr Met Leu Asp Cys Trp His
            275                 280                 285

Gly Glu Pro Ser Gln Arg Pro Thr Phe Ser Glu Leu Val Glu His Leu
            290                 295                 300

Gly Asn Leu Leu Gln Ala Asn Ala Gln Asp
305                 310                 315

<210> SEQ ID NO 4
<211> LENGTH: 435
<212> TYPE: PRT
<213> ORGANISM: Unknown
<220> FEATURE:
<223> OTHER INFORMATION: cFMS protein sequence used for screening

<400> SEQUENCE: 4

Tyr Lys Tyr Lys Gln Lys Pro Lys Tyr Gln Val Arg Trp Lys Ile Ile
1               5                   10                  15

Glu Ser Tyr Glu Gly Asn Ser Tyr Thr Phe Ile Asp Pro Thr Gln Leu
            20                  25                  30

Pro Tyr Asn Glu Lys Trp Glu Phe Pro Arg Asn Asn Leu Gln Phe Gly
            35                  40                  45

Lys Thr Leu Gly Ala Gly Ala Phe Gly Lys Val Glu Ala Thr Ala
    50                  55                  60

Phe Gly Leu Gly Lys Glu Asp Ala Val Leu Lys Val Ala Val Lys Met
65                  70                  75                  80

Leu Lys Ser Thr Ala His Ala Asp Glu Lys Glu Ala Leu Met Ser Glu
                85                  90                  95

Leu Lys Ile Met Ser His Leu Gly Gln His Glu Asn Ile Val Asn Leu
            100                 105                 110

Leu Gly Ala Cys Thr His Gly Gly Pro Val Leu Val Ile Thr Glu Tyr
        115                 120                 125

Cys Cys Tyr Gly Asp Leu Leu Asn Phe Leu Arg Arg Lys Ala Glu Ala
130                 135                 140

Met Leu Gly Pro Ser Leu Ser Pro Gly Gln Asp Pro Glu Gly Gly Val
145                 150                 155                 160

Asp Tyr Lys Asn Ile His Leu Glu Lys Lys Tyr Val Arg Arg Asp Ser
                165                 170                 175

Gly Phe Ser Ser Gln Gly Val Asp Thr Tyr Val Glu Met Arg Pro Val
            180                 185                 190

Ser Thr Ser Ser Asn Asp Ser Phe Ser Glu Gln Asp Leu Asp Lys Glu
        195                 200                 205

Asp Gly Arg Pro Leu Glu Leu Arg Asp Leu Leu His Phe Ser Ser Gln
    210                 215                 220

Val Ala Gln Gly Met Ala Phe Leu Ala Ser Lys Asn Cys Ile His Arg
225                 230                 235                 240

Asp Val Ala Ala Arg Asn Val Leu Leu Thr Asn Gly His Val Ala Lys
                245                 250                 255

Ile Gly Asp Phe Gly Leu Ala Arg Asp Ile Met Asn Asp Ser Asn Tyr
            260                 265                 270

Ile Val Lys Gly Asn Ala Arg Leu Pro Val Lys Trp Met Ala Pro Glu
        275                 280                 285

Ser Ile Phe Asp Cys Val Tyr Thr Val Gln Ser Asp Val Trp Ser Tyr
    290                 295                 300
```

```
Gly Ile Leu Leu Trp Glu Ile Phe Ser Leu Gly Leu Asn Pro Tyr Pro
305                 310                 315                 320

Gly Ile Leu Val Asn Ser Lys Phe Tyr Lys Leu Val Lys Asp Gly Tyr
                325                 330                 335

Gln Met Ala Gln Pro Ala Phe Ala Pro Lys Asn Ile Tyr Ser Ile Met
            340                 345                 350

Gln Ala Cys Trp Ala Leu Glu Pro Thr His Arg Pro Thr Phe Gln Gln
            355                 360                 365

Ile Cys Ser Phe Leu Gln Glu Gln Ala Gln Glu Asp Arg Arg Glu Arg
            370             375             380

Asp Tyr Thr Asn Leu Pro Ser Ser Ser Arg Ser Gly Gly Ser Gly Ser
385                 390                 395                 400

Ser Ser Ser Glu Leu Glu Glu Glu Ser Ser Ser Glu His Leu Thr Cys
                405                 410                 415

Cys Glu Gln Gly Asp Ile Ala Gln Pro Leu Leu Gln Pro Asn Asn Tyr
            420                 425                 430

Gln Phe Cys
435
```

PYRIDONE AMIDES AND ANALOGS EXHIBITING ANTI-CANCER AND ANTI-PROLIFERATIVE ACTIVITIES

This application claims the priority benefit of U.S. Provisional Application No. 61/562,602 filed Nov. 22, 2011. This provisional application is incorporated by reference herein in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_051_01US_SeqList_ST25.txt, date recorded: Nov. 21, 2012, file size 17 kilobytes).

FIELD OF THE INVENTION

The present invention relates to kinase inhibitors exhibiting novel and unexpected properties useful for the treatment of various diseases including hyperproliferative diseases and cancer. More particularly, the invention is concerned with such compounds, methods of treating diseases, and methods of synthesis of the compounds. Preferably, the compounds are useful for the modulation of activity of c-MET kinase, c-MET kinase polymorphs, c-MET kinase mutants, or c-MET kinase fusion proteins in the treatment of mammalian diseases, and in particular human hyperproliferative diseases and human cancers. In some embodiments, compounds disclosed herein exhibit unexpected selectivity for modulation of c-MET kinase activity.

BACKGROUND OF THE INVENTION c-MET is a receptor tyrosine kinase (RTK) encoded by human chromosome 7p and activated via its natural extracellular ligand hepatocyte growth factor (HGF) or activated in the absence of HGF when overexpressed or mutated. c-MET is found mutated in a variety of solid tumors (Ma, P. C. et al. *Cancer Metastasis* (2003) 22: 309). Mutations in the tyrosine kinase domain are associated with hereditary papillary renal cell carcinomas (Schmidt, L. et al. *Nat. Genet.* (1997)16: 68; Schmidt, L. et al. *Oncogene* (1999) 18: 2343), whereas mutations in the sema and juxtamembrane domains are often found in small cell lung cancers (Ma, P. C. et al. *Cancer Res.* (2003) 63: 6272). Many activating mutations are also found in breast cancers (Nakopoulou, et al. *Histopath.* (2000) 36(4): 313). The panoply of tumor types for which c-MET mediated growth has been implicated suggests this is a target suited for modulation by specific c-MET small molecule inhibitors.

The TPR-MET oncogene is a transforming variant of the c-MET RTK and was initially identified after treatment of a human osteogenic sarcoma cell line transformed by the chemical carcinogen N-methyl-N-nitro-N-nitrosoguanidine (Park, M. et al. *Cell* (1986) 45: 895). The TPR-MET fusion oncoprotein is the result of a chromosomal translocation, placing the TPR3 locus on chromosome 1 upstream of a portion of the c-MET gene on chromosome 7 encoding only for the cytoplasmic region. Studies suggest that TPR-MET is detectable in experimental cancers (e.g., Yu, J. et al. *Cancer* (2000) 88: 1801). Dimerization of the $M_r$ 65,000 TPR-MET oncoprotein through a leucine zipper motif encoded by TPR leads to constitutive activation of the c-MET kinase (Zhen, Z. et al. *Oncogene* (1994) 9: 1691). TPR-MET activates wild-type c-MET RTK and can activate crucial cellular growth pathways, including the Ras pathway (Aklilu, F. et al. *Am. J. Physiol.* (1996) 271: E277) and the phosphatidylinositol 3-kinase (PI3K)/AKT pathway (Ponzetto, C. et al. *Mol. Cell. Biol.* (1993) 13: 4600). Conversely, in contrast to c-MET RTK, TPR-MET is ligand independent, lacks the CBL-like SH2 domain binding site in the juxtamembrane region in c-MET, and is mainly cytoplasmic. c-MET immunohistochemical expression seems to be associated with abnormal β-catenin expression, a hallmark feature of epithelial to mesenchymal transition (EMT) and provides good prognostic and predictive factors in breast cancer patients.

It has recently been reported that sustained signaling through cMET kinase may drive the disease etiology of autozomal-dominant polcystic kidney disease (PKD) (Quin, S. et al. *J. Clin. Investigation* (2010) 120: 3617-3628). Therefore a c-MET kinase inhibitor finds utility in the treatment of PKD and other related ciliopathies.

In human therapeutics, it is desirable to provide small molecule inhibitors of a protein target within in a protein family which do not cross-inhibit closely related protein family members. These closely related protein family members are often referred to as 'off-targets', to distinguish them from the essential target of interest referred to as the 'on target' of the inhibitor. A small molecule which inhibits multiple protein family members, while being potent against the target of interest, can be limited in its utility as a human therapeutic due to unintended side effects and toxicities introduced due to the consequences of inhibition of these 'off targets.'

Protein kinases constitute an important therapeutic protein family. There are approximately 518 human protein kinases. While inhibition of a desired kinase 'on target' is desirable for a human therapeutic, it is also desirable in many cases to provide a selective kinase inhibitor which does not substantially inhibit other kinase 'off targets' from within this protein family. Monoclonal antibodies are one approach to providing specific inhibitors to a specific kinase without inhibiting 'off targets.' Achieving this level of selectivity with small molecule inhibitors, however, is not as easily achievable nor as straightforward. Accordingly, there is a need for kinase inhibitors that are selective for a particular protein kinase.

SUMMARY OF THE INVENTION

In has been unexpectedly found that compounds described herein exhibit potent and selective inhibition of c-MET kinase relative to other kinases. As such, compounds described herein find utility in the treatment of mammalian cancers and especially human cancers including, but not limited to, solid tumors, gastric cancers, melanomas, glioblastomas, ovarian cancer, pancreatic cancer, prostate cancer, lung cancers, non small cell lung cancer, breast cancers, kidney cancers, cervical carcinomas, metastasis of primary tumor sites, colonic cancers, myeloproliferative diseases, ciliopathies including polycystic kidney disease, diseases wherein the etiology or progression is dependent on c-MET kinase activity, or on the activity of oncogenic forms, aberrant fusion protein forms, and mutant forms of c-MET kinase.

Specifically, pyridone amide compounds of Formula I are disclosed which find utility in the treatment of diseases as described above.

Formula I

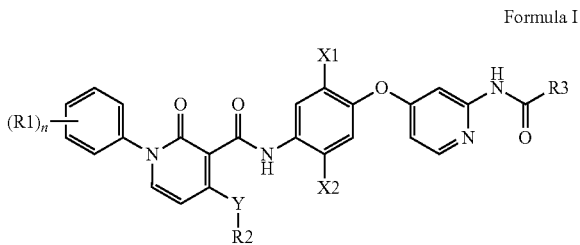

wherein R1, R2, R3, m, X1, X2, and Y are as defined below for Formula I.

Accordingly, in one embodiment, the present invention comprises a compound of Formula I, Formula I

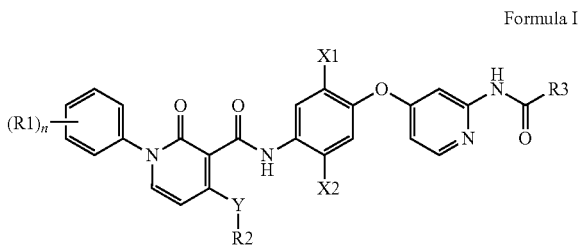

or a pharmaceutically acceptable salt, hydrate, solvate, enantiomer, stereoisomer or tautomer thereof, wherein:
X1 is halogen;
X2 is halogen;
Y is O, —NH;
each R1 is individually and independently halogen, H, C1-C6 alkyl, C3-C8 branched alkyl, C3-C8 cycloalkyl, C1-C6 alkoxy, branched C3-C6 alkoxy, or cyano;
each R2 is individually and independently C1-C6 alkyl, deuteroC1-C6alkyl wherein the alkyl moiety can be partially or fully deuterated, C3-C8 branched alkyl, deuteroC3-C8 branched alkyl wherein the alkyl moiety can be partially or fully deuterated, C3-C8 cycloalkyl, C1-C6 alkoxy C1-C6 alkyl, branched C3-C6 alkoxy C1-C6 alkyl or (R7)R6N—C1-C6-alkyl;
R3 is C1-C6 alkyl, C3-C8 branched alkyl, C3-C8 cycloalkyl, —NR6(R7), —R4, wherein each alkyl, branched or cycloalkyl may be optionally substituted with cyano, C1-C6alkoxy, or hydroxy;
each R4 is independently and individually selected from the group consisting of

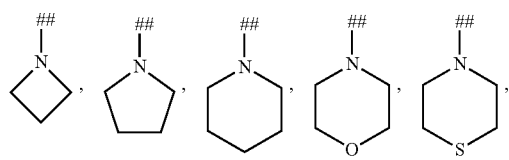

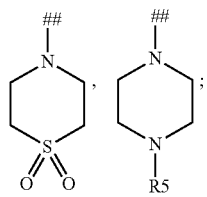

and wherein the symbol (##) is the point of attachment of the R4 moiety;
R5 is C1-C6 alkyl, C3-C8 branched alkyl, C3-C8 cycloalkyl, C1-C6 alkoxy C1-C6 alkyl;
each R6 and R7 is individually and independently H, C1-C6 alkyl, or branched C3-C8 alkyl;
each cycloalkyl and R4 is independently and optionally substituted with —(R8)$_p$;
each R8 is individually and independently C1-C6 alkyl, branched C3-C8 alkyl, halogen, —(CH$_2$)$_m$—CN, —(CH$_2$)$_m$—OR6, —(CH$_2$)$_m$—NR6(R7), —(CH$_2$)$_m$—SO$_2$—C1-C6-alkyl, —(CH$_2$)$_m$—C(O)NR6(R7), —(CH$_2$)$_m$—C(O)—C4-C6-heterocyclyl, or —(CH$_2$)$_m$—C4-C6-heterocyclyl, wherein each alkyl or alkylene is optionally substituted with one or two C1-C6 alkyl;
each m is individually and independently 0, 1, 2, or 3;
n is 0, 1, 2, or 3;
p is 0, 1, 2, 3, or 4.

In some embodiments of the compound of Formula I, R1 is fluoro or H and n is 1.

In some embodiments of the compound of Formula I, R2 is C1-C6 alkyl or C3-C8 branched alkyl.

In some embodiments of the compound of Formula I, R3 is C1-C6 alkyl, C3-C8 branched alkyl, or C3-C8 cycloalkyl.

In some embodiments of the compound of Formula I, R3 is —NR6(R7) or R4.

In some embodiments, the compound of Formula I is a compound of Formula Ia,

Formula Ia

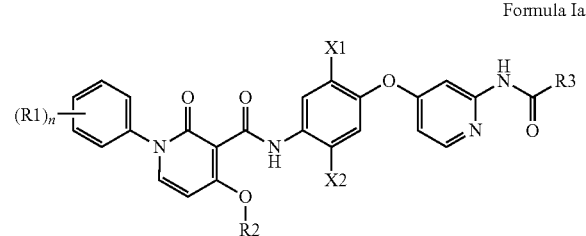

or a pharmaceutically acceptable salt, hydrate, solvate, enantiomer, stereoisomer or tautomer thereof.

In some embodiments of the compound of Formula Ia, R1 is fluoro or H and n is 1.

In some embodiments of the compound of Formula Ia, R2 is C1-C6 alkyl or C3-C8 branched alkyl.

In some embodiments of the compound of Formula Ia, R3 is C1-C6 alkyl, C3-C8 branched alkyl, or C3-C8 cycloalkyl.

In some embodiments of the compound of Formula Ia, R3 is —NR6(R7) or R4.

In some embodiments, the compound of Formula Ia is a compound of Formula Ib,

Formula Ib

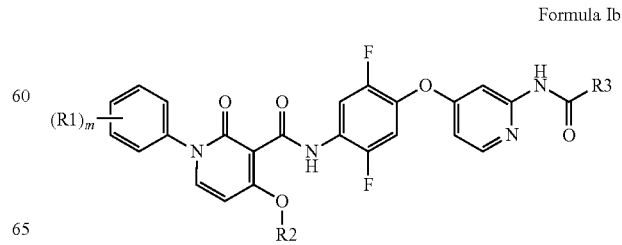

or a pharmaceutically acceptable salt, hydrate, solvate, enantiomer, stereoisomer or tautomer thereof.

In some embodiments of the compound of Formula Ib, R1 is fluoro or H and n is 1.

In some embodiments of the compound of Formula Ib, R2 is C1-C6 alkyl or C3-C8 branched alkyl.

In some embodiments of the compound of Formula Ib, R3 is C1-C6 alkyl, C3-C8 branched alkyl, or C3-C8 cycloalkyl.

In some embodiments of the compound of Formula Ib, R3 is —NR6(R7) or R4.

In some embodiments, the compound of Formula Ib is a compound of Formula Ic,

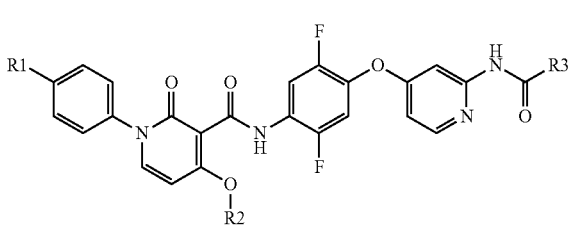

Formula Ic or a pharmaceutically acceptable salt, hydrate, solvate, enantiomer, stereoisomer or tautomer thereof.

In some embodiments of the compound of Formula Ic, R1 is fluoro or H.

In some embodiments of the compound of Formula Ic, R2 is C1-C6 alkyl or C3-C8 branched alkyl.

In some embodiments of the compound of Formula Ic, R3 is C1-C6 alkyl, C3-C8 branched alkyl, or C3-C8 cycloalkyl.

In some embodiments of the compound of Formula Ic, R3 is —NR6(R7) or R4.

In some embodiments of the compound of Formula Ic, R1 is fluoro or H, R2 is C1-C6 alkyl or C3-C8 branched alkyl, and R3 is C1-C6 alkyl, C3-C8 branched alkyl, or C3-C8 cycloalkyl.

In some embodiments of the compound of Formula Ic, R1 is fluoro or H, R2 is C1-C6 alkyl or C3-C8 branched alkyl, and R3 is —NR6(R7) or R4.

In some embodiments, the compound of Formula I is a compound of Formula Id,

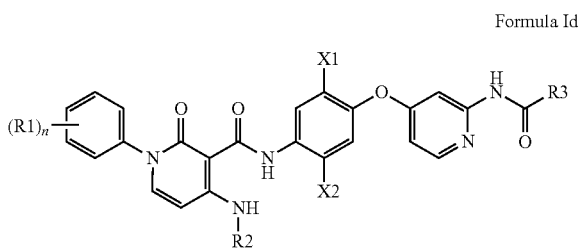

Formula Id or a pharmaceutically acceptable salt, hydrate, solvate, enantiomer, stereoisomer or tautomer thereof.

In some embodiments of the compound of Formula Id, R1 is fluoro or H and n is 1.

In some embodiments of the compound of Formula Id, R2 is C1-C6 alkyl or C3-C8 branched alkyl.

In some embodiments of the compound of Formula Id, R3 is C1-C6 alkyl, C3-C8 branched alkyl, or C3-C8 cycloalkyl.

In some embodiments of the compound of Formula Id, R3 is —NR6(R7) or R4.

In some embodiments, the compound of Formula Id is a compound of Formula Ie,

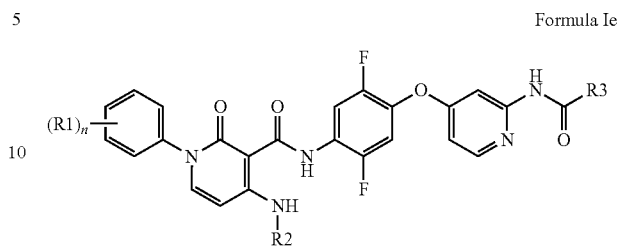

Formula Ie or a pharmaceutically acceptable salt, hydrate, solvate, enantiomer, stereoisomer or tautomer thereof.

In some embodiments of the compound of Formula Ie, R1 is fluoro or H and n is 1.

In some embodiments of the compound of Formula Ie, R2 is C1-C6 alkyl or C3-C8 branched alkyl.

In some embodiments of the compound of Formula Ie, R3 is C1-C6 alkyl, C3-C8 branched alkyl, or C3-C8 cycloalkyl.

In some embodiments of the compound of Formula Ie, R3 is —NR6(R7) or R4.

In some embodiments, the compound of Formula Ie is a compound of Formula If,

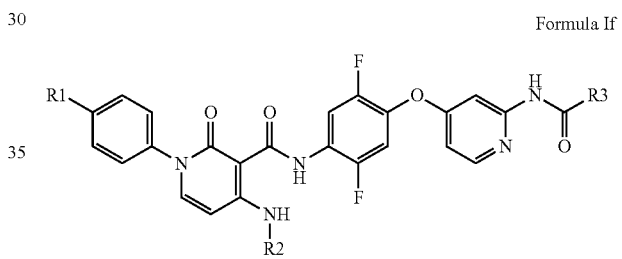

Formula If or a pharmaceutically acceptable salt, hydrate, solvate, enantiomer, stereoisomer or tautomer thereof.

In some embodiments of the compound of Formula If, R1 is fluoro or H.

In some embodiments of the compound of Formula If, R2 is C1-C6 alkyl or C3-C8 branched alkyl.

In some embodiments of the compound of Formula If, R3 is C1-C6 alkyl, C3-C8 branched alkyl, or C3-C8 cycloalkyl.

In some embodiments of the compound of Formula If, R3 is —NR6(R7) or R4.

In some embodiments of the compound of Formula If, R1 is fluoro or H, R2 is C1-C6 alkyl or C3-C8 branched alkyl, and R3 is C1-C6 alkyl, C3-C8 branched alkyl, or C3-C8 cycloalkyl.

In some embodiments of the compound of Formula If, R1 is fluoro or H, R2 is C1-C6 alkyl or C3-C8 branched alkyl, and R3 is —NR6(R7) or R4.

In some embodiments, any one or more hydrogens of the alkyl substituents of R1, R2, R3, R5, R6, and R7 may be substituted with deuterium.

In some embodiments, the invention comprises a compound selected from the group consisting of N-(4-((2-acetamidopyridin-4-yl)oxy)-2,5-difluorophenyl)-4-ethoxy-1-(4-fluorophenyl)-2-oxo-1,2-dihydropyridine-3-carboxamide,
N-(2,5-difluoro-4-((2-propionamidopyridin-4-yl)oxy)phenyl)-4-ethoxy-1-(4-fluorophenyl)-2-oxo-1,2-dihydropyridine-3-carboxamide, N-(4-((2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-pivalamidopyridin-4-yl)oxy)phenyl)-4-ethoxy-1-(4-fluorophenyl)-2-oxo-1,2-dihydropyridine-3-carboxamide, N-(2,5-difluoro-4-((2-isobutyramidopyridin-4-yl)oxy)phenyl)-4-ethoxy-1-(4-fluorophenyl)-2-oxo-1,2-dihydropyridine-3-carboxamide, N-(4-((2-(cyclopropanecarboxamido)pyridin-4-yl)oxy)-2,5-difluorophenyl)-4-(ethylamino)-1-(4-fluorophenyl)-2-oxo-1,2-dihydropyridine-3-carboxamide, N-(4-((2-acetamidopyridin-4-yl)oxy)-2,5-difluorophenyl)-1-(4-fluorophenyl)-4-(methylamino)-2-oxo-1,2-dihydropyridine-3-carboxamide, N-(4-((2-acetamidopyridin-4-yl)oxy)-2,5-difluorophenyl)-4-(ethylamino)-1-(4-fluorophenyl)-2-oxo-1,2-dihydropyridine-3-carboxamide, N-(4-((2-acetamidopyridin-4-yl)oxy)-2,5-difluorophenyl)-1-(4-fluorophenyl)-4-isopropoxy-2-oxo-1,2-dihydropyridine-3-carboxamide, N-(2,5-difluoro-4-((2-propionamidopyridin-4-yl)oxy)phenyl)-1-(4-fluorophenyl)-4-isopropoxy-2-oxo-1,2-dihydropyridine-3-carboxamide, 1-(4-(2,5-difluoro-4-(1-(4-fluorophenyl)-4-(methylamino)-2-oxo-1,2-dihydropyridine-3-carboxamido)phenoxy)pyridin-2-yl)-3-methylurea, N-(4-((2-acetamidopyridin-4-yl)oxy)-5-chloro-2-fluorophenyl)-4-ethoxy-1-(4-fluorophenyl)-2-oxo-1,2-dihydropyridine-3-carboxamide, N-(5-chloro-2-fluoro-4-((2-propionamidopyridin-4-yl)oxy)phenyl)-4-ethoxy-1-(4-fluorophenyl)-2-oxo-1,2-dihydropyridine-3-carboxamide, N-(5-chloro-4-(2-(cyclopropanecarboxamido)pyridin-4-yl)oxy)-2-fluorophenyl)-4-ethoxy-1-(4-fluorophenyl)-2-oxo-1,2-dihydropyridine-3-carboxamide, N-(4-((2-(3,3-dimethylureido)pyridin-4-yl)oxy)-2,5-difluorophenyl)-4-ethoxy-1-(4-fluorophenyl)-2-oxo-1,2-dihydropyridine-3-carboxamide, or N-(2,5-difluoro-4-((2-propionamidopyridin-4-yl)oxy)phenyl)-4-(ethoxy-d5)-1-(4-fluorophenyl)-2-oxo-1,2-dihydropyridine-3-carboxamide, and pharmaceutically acceptable salts, solvates, hydrates and tautomers thereof.

In certain embodiments, the invention comprises a method of treating mammalian disease wherein the disease etiology or progression is at least partially mediated by a kinase activity, wherein the kinase is a wildtype form, a mutant oncogenic form, an aberrant fusion protein form or a polymorph, the method comprising administering to a mammal in need thereof an effective amount of a compound of formula I.

In certain embodiments, the disease etiology or progression is at least partially mediated by the kinase activity of c-MET, mutant oncogenic forms, aberrant fusion proteins, or polymorphs thereof.

In other embodiments, the present invention comprises a pharmaceutical composition, comprising a compound of formula I and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, or diseases characterized by angiogenesis, such as solid tumors, melanomas, glioblastomas, ovarian cancer, pancreatic cancer, prostate cancer, lung cancers, breast cancers, renal cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, colonic cancers, ocular diseases characterized by hyperproliferation leading to blindness including retinopathies, diabetic retinopathy, age-related macular degeneration, hypereosinophilic syndrome, rheumatoid arthritis, asthma, chronic obstructive pulmonary disease, mastocytosis, or mast cell leukemia, the method comprising administering to a patient in need thereof an effective amount of a compound of formula I.

In some embodiments, the invention includes a method of treating ciliopathies or polycystic kidney disease, the method comprising administering to a patient in need thereof an effective amount of a compound of formula I.

In certain embodiments of the present methods, the compound is administered orally, parenterally, by inhalation, or subcutaneously.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION OF THE INVENTION

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, pharmaceutically acceptable salts, and solvates thereof, as well as crystalline polymorphic forms of the disclosed compounds and any and all possible isomers, stereoisomers, enantiomers, diastereomers, tautomers, pharmaceutically acceptable salts, and solvates thereof. Thus, the terms "compound", "compounds", "test compound" or "test compounds" as used in this disclosure refer to the compounds of this disclosure and any and all possible isomers, stereoisomers, enantiomers, diastereomers, tautomers, pharmaceutically acceptable salts, solvates, and crystalline polymorphs thereof.

DEFINITIONS

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —$CH_2$—, —$CH_2CH_2$—, and —$CH_2CH_2CH_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands. For example, in some embodiments, a ring N atom from the heterocyclyl is the bonding atom of the heterocylic moiety. In exemplary embodiments, "heterocyclyl" refers to a cyclic hydrocarbon as described above containing 4, 5, or 6 ring atoms (i.e., C4-C6 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term "subject" includes, without limitation, a human or an animal. Exemplary animals include, but are not limited to, mammals such as mouse, rat, guinea pig, dog, feline, horse, cow, pig, monkey, chimpanzee, baboon, or rhesus monkey.

The term "treating" as used herein with regard to a subject, refers to improving at least one symptom of the subject's disorder. Treating can be curing, improving, or at least partially ameliorating the disorder.

The term "hydrate" as used herein refers to a compound disclosed herein which is associated with water in the molecular form, i.e., in which the H—OH bond is not split, and may be represented, for example, by the formula R.H$_2$O, where R is a compound disclosed herein. A given compound may form more than one hydrate including, for example, monohydrates (R.H$_2$O), dihydrates (R.2H$_2$O), trihydrates (R.3H$_2$O), and the like.

The term "solvate" as used herein refers to a compound disclosed herein which is associated with solvent in the molecular form, i.e., in which the solvent is coordinatively bound, and may be represented, for example, by the formula R.(solvent), where R is a compound disclosed herein. A given compound may form more than one solvate including, for example, monosolvates (R.(solvent)) or polysolvates (R.n (solvent)) wherein n is an integer greater than 1) including, for example, disolvates (R.2(solvent)), trisolvates (R.3(solvent)), and the like, or hemisolvates, such as, for example, R.n/2(solvent), R.n/3(solvent), R.n/4(solvent) and the like, wherein n is an integer. Solvents herein include mixed solvents, for example, methanol/water, and as such, the solvates may incorporate one or more solvents within the solvate.

The term "acid hydrate" as used herein refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

G-X—Y=Z ⇌ X=Y—Z-G where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is H', is also known as "prototropy." Tautomers are defined as isomers that arise from tautomerism, independent of whether the isomers are isolable.

ChemDraw version 8.0 or 10, (CambridgeSoft Corporation, Cambridge, Mass.) was used to name sructures.

The following abbreviations are used in this disclosure and have the following definitions: ADP is adenosine diphosphate, ATP is adenosine triphosphate, DCM is dichloromethane, DIEA is N,N-diisopropylethylamine, DMA is N,N-dimethylacetamide, DMAP is 4-(dimethylamino)pyridine, DMF is N,N-dimethylformamide, DMSO is dimethylsulfoxide, DTT is dithiothreitol, ESI is electrospray ionization, EtOAc is ethyl acetate, EtOH is ethanol, GST is glutathione S-transferase, "h" is hour or hours, Hex is hexane, IC$_{50}$ is half maximal inhibitory concentration, min is minutes, MeCN is acetonitrile, MeOH is methanol, MHz is megahertz, MS is mass spectrometry, MTBE is methyl tert-butyl ether, NADH is nicotinamide adenine dinucleotide, NMR is nuclear magnetic resonance, PBS is phosphate buffered saline, Pd$_2$(dba)$_3$ is tris(dibenzylideneacetone)dipalladium(0), prep-HPLC is preparative high performance liquid chromatography, RT is room temperature which is also known as "ambient temp," which will be understood to consist of a range of normal laboratory temperatures ranging from 15-25° C., TBTU is O-(Benzotriazol-1-yl)-N,N,N',N'-tetramethyluronium tetrafluoroborate, TFA is trifluoroacetic acid, THF is tetrahydrofuran, Tris is tris(hydroxymethyl)aminomethane, and Xantphos is 4,5-bis(diphenylphosphino)-9,9-dimethylxanthene.

Compounds

In one embodiment, compounds of the Formula I are described:

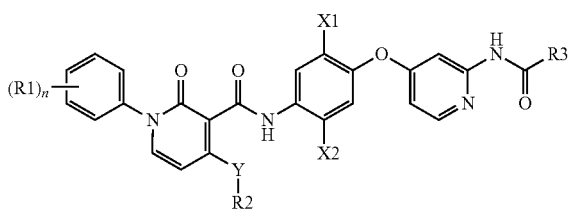

Formula I and pharmaceutically acceptable salts, hydrates, solvates, enantiomers, stereoisomers, and tautomers thereof; wherein X1, X2, Y, R1, R2, R3, R4, R5, R6, R7, R8, m, n, and p are as defined above for Formula I;

In further embodiments, compounds of the Formula I are compounds of Formula I.1 wherein X1, X2, Y, R2, R3, R4, R5, R6, R7, R8, m, and p are as broadly defined above for Formula I; and R1 is fluoro or H and n is 1.

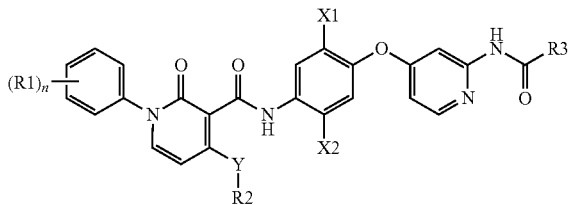

Formula I.1

In some embodiments, compounds of the Formula I are compounds of Formula I.2, wherein X1, X2, Y, R1, R3, R4, R5, R6, R7, R8, m, n, and p are as broadly defined above for Formula I; and R2 is C1-C6 alkyl or C3-C8 branched alkyl.

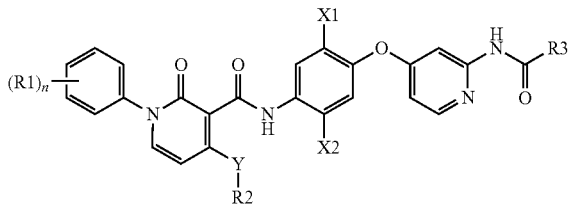

Formula I.2

In some embodiments, compounds of the Formula I are compounds of Formula I.3, wherein X1, X2, Y, R1, R2, R4, R5, R6, R7, R8, m, n, and p are as broadly defined above for Formula I; and R3 is C1-C6 alkyl, C3-C8 branched alkyl, or C3-C8 cycloalkyl.

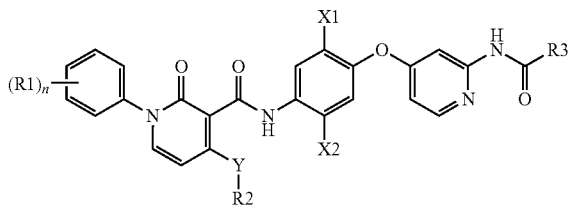

Formula I.3

In some embodiments, compounds of the Formula I are compounds of Formula I.4, wherein X1, X2, Y, R1, R2, R4, R5, R6, R7, R8, m, n, and p are as broadly defined above for Formula I; and R3 is —NR6(R7) or R4.

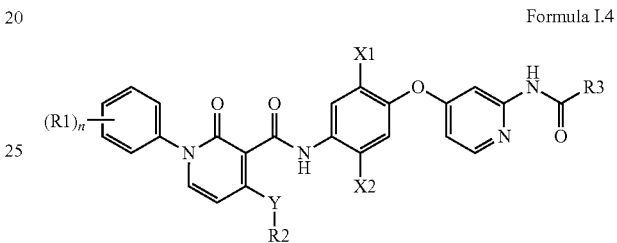

Formula I.4

In some embodiments, the compounds of the Formula I are compounds of the Formula Ia:

Formula Ia wherein

X1, X2, R1, R2, R3, R4, R5, R6, R7, R8, m, n, and p are as broadly defined above for Formula I.

In some embodiments, the compounds of the Formula Ia are compounds of Formula Ia.1, Formula Ia.1 wherein

X1, X2, R2, R3, R4, R5, R6, R7, R8, m, and p are as broadly defined above for Formula I; and R1 is fluoro or H, and n is 1.

In some embodiments, the compounds of the Formula Ia are compounds of Formula Ia.2, Formula Ia.2 wherein

X1, X2, R1, R3, R4, R5, R6, R7, R8, m, n, and p are as broadly defined above for Formula I; and R2 is C1-C6 alkyl or C3-C8 branched alkyl.

In some embodiments, the compounds of the Formula Ia are compounds of Formula Ia.3, Formula Ia.3 wherein

X1, X2, R1, R2, R4, R5, R6, R7, R8, m, n, and p are as broadly defined above for Formula I; and R3 is C1-C6 alkyl, C3-C8 branched alkyl, or C3-C8 cycloalkyl.

In some embodiments, the compounds of the Formula Ia are compounds of Formula Ia.4, Formula Ia.4 wherein

X1, X2, R1, R2, R4, R5, R6, R7, R8, m, n, and p are as broadly defined above for Formula I; and R3 is —NR6(R7) or R4.

In some embodiments, the compounds of the Formula Ia are compounds of the Formula Ib:

Formula Ib wherein

R1, R2, R3, R4, R5, R6, R7, R8, m, n, and p are as broadly defined above for Formula I.

In some embodiments, the compounds of the Formula Ib are compounds of the Formula Ib.1:

Formula Ib.1 wherein

R2, R3, R4, R5, R6, R7, R8, m, and p are as broadly defined above for Formula I; and R1 is fluoro or H, and n is 1.

In some embodiments, the compounds of the Formula Ib are compounds of the Formula Ib.2:

Formula Ib.2 wherein

R1, R3, R4, R5, R6, R7, R8, m, n, and p are as broadly defined above for Formula I; and R2 is C1-C6 alkyl or C3-C8 branched alkyl.

In some embodiments, the compounds of the Formula Ib are compounds of the Formula Ib.3:

Formula Ib.3 wherein
R1, R2, R4, R5, R6, R7, R8, m, n, and p are as broadly defined above for Formula I; and R3 is C1-C6 alkyl, C3-C8 branched alkyl, or C3-C8 cycloalkyl.

In some embodiments, the compounds of the Formula Ib are compounds of the Formula Ib.4:

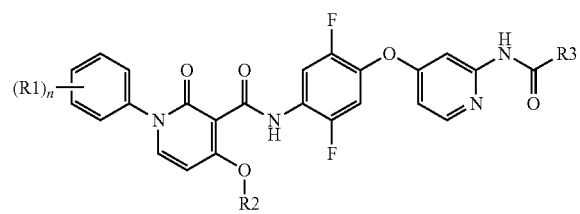

Formula Ib.4 wherein
R1, R2, R4, R5, R6, R7, R8, m, n, and p are as broadly defined above for Formula I; and R3 is —NR6(R7) or R4.

In some embodiments, compounds of the Formula Ib are compounds of the Formula Ic:

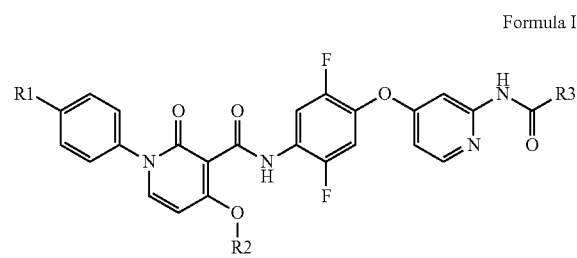

Formula Ic wherein
R1, R2, R3, R4, R5, R6, R7, R8, m, and p are as broadly defined above for Formula I.

In some embodiments, compounds of the Formula Ic are compounds of the Formula Ic.1:

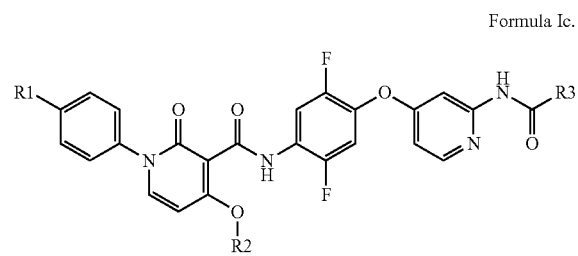

Formula Ic.1 wherein
R1, R2, R4, R5, R6, R7, R8, m, and p are as broadly defined above for Formula I; and
R3 is C1-C6 alkyl, C3-C8 branched alkyl, or C3-C8 cycloalkyl.

In some embodiments, compounds of the Formula Ic are compounds of the Formula Ic.2:

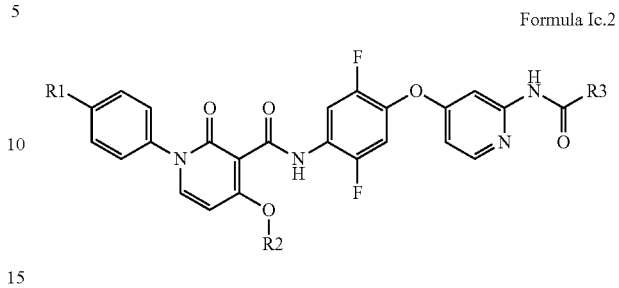

Formula Ic.2 wherein
R1, R2, R4, R5, R6, R7, R8, m, and p are as broadly defined above for Formula I; and
R3 is —NR6(R7) or R4.

In some embodiments, compounds of the Formula Ic are compounds of the Formula Ic.3:

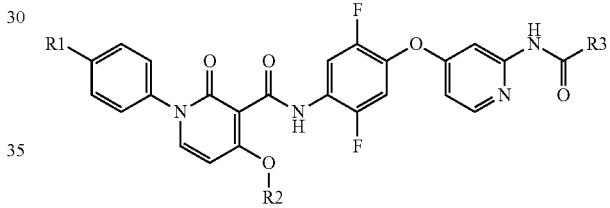

Formula Ic.3 wherein
R2, R3, R4, R5, R6, R7, R8, m, and p are as broadly defined above for Formula I; and R1 is fluoro or H.

In some embodiments, compounds of the Formula Ic are compounds of the Formula Ic.4:

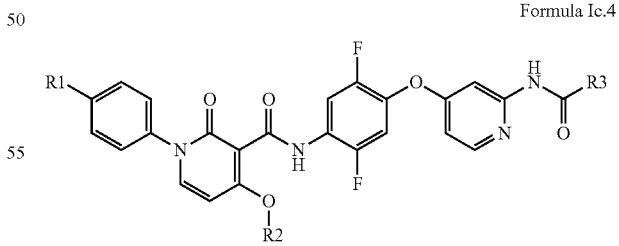

Formula Ic.4 wherein
R1, R3, R4, R5, R6, R7, R8, m, and p are as broadly defined above for Formula I; and
R2 is C1-C6 alkyl or C3-C8 branched alkyl.

In some embodiments, compounds of the Formula Ic are compounds of the Formula Ic.5:

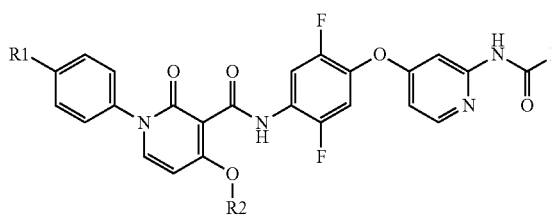

Formula Ic.5 wherein
R4, R5, R6, R7, R8, m, and p are as broadly defined above for Formula I; and R1 is fluoro or H, R2 is C1-C6 alkyl or C3-C8 branched alkyl, and R3 is C1-C6 alkyl, C3-C8 branched alkyl, or C3-C8 cycloalkyl.

In some embodiments, compounds of the Formula Ic are compounds of the Formula Ic.5:

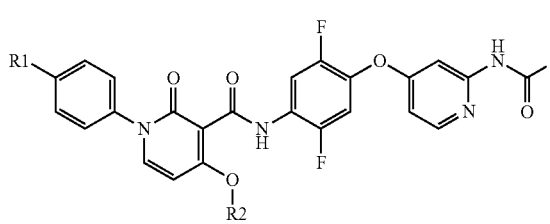

Formula Ic.5 wherein
R4, R5, R6, R7, R8, m, and p are as broadly defined above for Formula I; and R1 is fluoro or H, R2 is C1-C6 alkyl or C3-C8 branched alkyl, and R3 is —NR6(R7) or R4.

In some embodiments, compounds of the Formula I are compounds of the Formula Id:

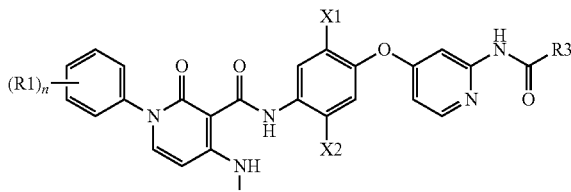

Formula Id wherein
X1, X2, R1, R2, R3, R4, R5, R6, R7, R8, m, n, and p are as broadly defined above for Formula I.

In some embodiments, compounds of the Formula Id are compounds of the Formula Id.1,

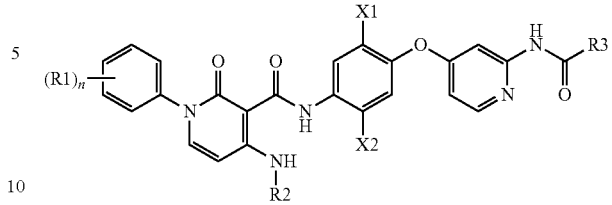

Formula Id.1 wherein
X1, X2, R2, R3, R4, R5, R6, R7, R8, m, and p are as broadly defined above for Formula I; and R1 is fluoro or H, and n is 1.

In some embodiments, compounds of the Formula Id are compounds of the Formula Id.2,

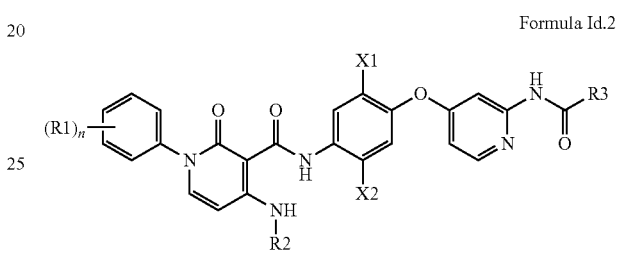

Formula Id.2 wherein
X1, X2, R1, R3, R4, R5, R6, R7, R8, m, n, and p are as broadly defined above for Formula I; and R2 is C1-C6 alkyl or C3-C8 branched alkyl.

In some embodiments, compounds of the Formula Id are compounds of the Formula Id.3, Formula Id.3

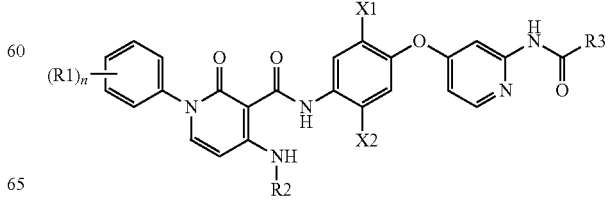

wherein
X1, X2, R1, R2, R4, R5, R6, R7, R8, m, n, and p are as broadly defined above for Formula I; and R3 is C1-C6 alkyl, C3-C8 branched alkyl, or C3-C8 cycloalkyl.

In some embodiments, compounds of the Formula Id are compounds of the Formula Id.4, Formula Id.4 wherein
X1, X2, R1, R2, R4, R5, R6, R7, R8, m, n, and p are as broadly defined above for Formula I; and R3 is —NR6(R7) or R4.

In further embodiments, the compounds of the Formula Id are compounds of the Formula Ie:

Formula Ie

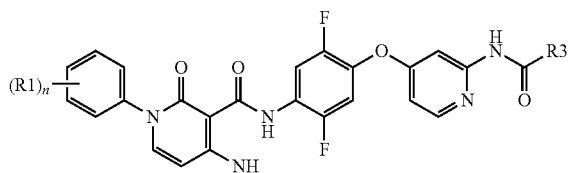

wherein
R1, R2, R3, R4, R5, R6, R7, R8, m, n, and p are as broadly defined above for Formula I.

In some embodiments, the compounds of the Formula Ie are compounds of the Formula Ie.1:

Formula Ie.1

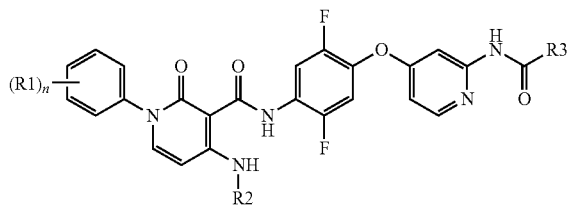

wherein
R2, R3, R4, R5, R6, R7, R8, m, and p are as broadly defined above for Formula I; and R1 is fluoro or H, and n is 1.

In some embodiments, the compounds of the Formula Ie are compounds of the Formula Ie.2:

Formula Ie.2

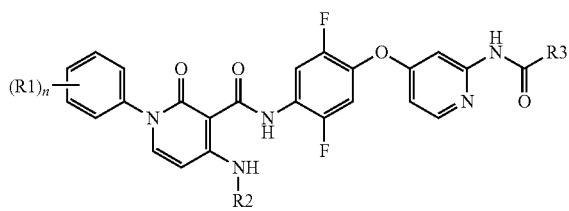

wherein
R1, R3, R4, R5, R6, R7, R8, m, n, and p are as broadly defined above for Formula I; and R2 is C1-C6 alkyl or C3-C8 branched alkyl.

In some embodiments, the compounds of the Formula Ie are compounds of the Formula Ie.3:

Formula Ie.3

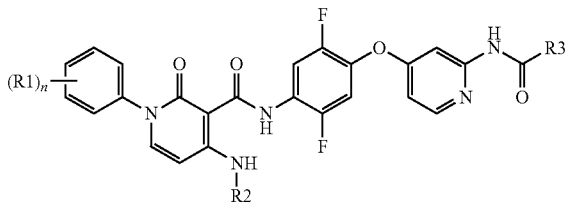

wherein
R1, R2, R4, R5, R6, R7, R8, m, n, and p are as broadly defined above for Formula I; and R3 is C1-C6 alkyl, C3-C8 branched alkyl, or C3-C8 cycloalkyl.

In some embodiments, the compounds of the Formula Ie are compounds of the Formula Ie.4:

Formula Ie.4

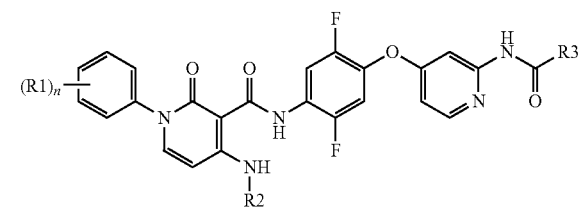

wherein
R1, R2, R4, R5, R6, R7, R8, m, n, and p are as broadly defined above for Formula I; and R3 is —NR6(R7) or R4.

In some embodiments, compounds of the Formula Ie are compounds of the Formula If:

Formula If

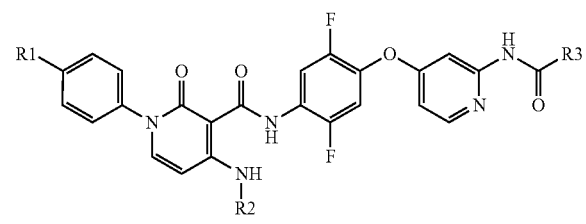

wherein
R1, R2, R3, R4, R5, R6, R7, R8, m, and p are as broadly defined above for Formula I.

In some embodiments, compounds of the Formula If are compounds of the Formula If.1:

Formula If.1

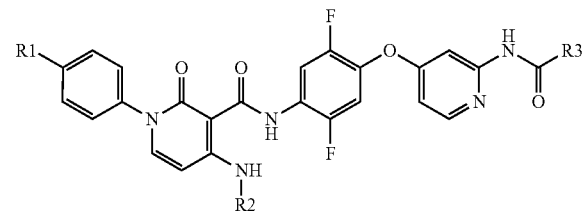

wherein

R1, R2, R4, R5, R6, R7, R8, m, and p are as broadly defined above for Formula I; and R3 is C1-C6 alkyl, C3-C8 branched alkyl, or C3-C8 cycloalkyl.

In some embodiments, compounds of the Formula If are compounds of the Formula If.2:

Formula If.2 wherein

R1, R2, R4, R5, R6, R7, R8, m, and p are as broadly defined above for Formula I; and R3 is —NR6(R7) or R4.

In some embodiments, compounds of the Formula If are compounds of the Formula If.3:

Formula If.3 wherein

R2, R3, R4, R5, R6, R7, R8, m, and p are as broadly defined above for Formula I; and R1 is fluoro or H.

In some embodiments, compounds of the Formula If are compounds of the Formula If.4:

Formula If.4 wherein

R1, R3, R4, R5, R6, R7, R8, m, and p are as broadly defined above for Formula I; and R2 is C1-C6 alkyl or C3-C8 branched alkyl.

In some embodiments, compounds of the Formula If are compounds of the Formula If.5:

Formula If.5 wherein

R4, R5, R6, R7, R8, m, and p are as broadly defined above for Formula I; and R1 is fluoro or H, R2 is C1-C6 alkyl or C3-C8 branched alkyl, and R3 is C1-C6 alkyl, C3-C8 branched alkyl, or C3-C8 cycloalkyl.

In some embodiments, compounds of the Formula If are compounds of the Formula If.6:

Formula If.6 wherein

R4, R5, R6, R7, R8, m, and p are as defined above for Formula I; and R1 is fluoro or H, R2 is C1-C6 alkyl or C3-C8 branched alkyl, and R3 is —NR6(R7) or R4.

In some embodiments, compounds of the Formula Ia are compounds of the Formula Ig:

Formula Ig wherein

R1, R2, R3, R4, R5, R6, R7, R8, m, n, and p are as broadly defined above for Formula I.

In some embodiments, compounds of the Formula Ig are compounds of the Formula Ig.1:

Formula Ig.1

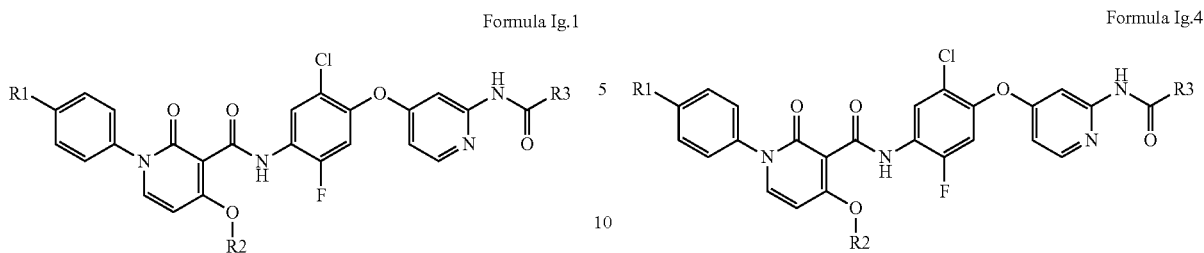

wherein
R1, R2, R3, R4, R5, R6, R7, R8, m, and p are as broadly defined above for Formula I.

In some embodiments, compounds of the Formula Ig are compounds of the Formula Ig.2:

Formula Ig.2

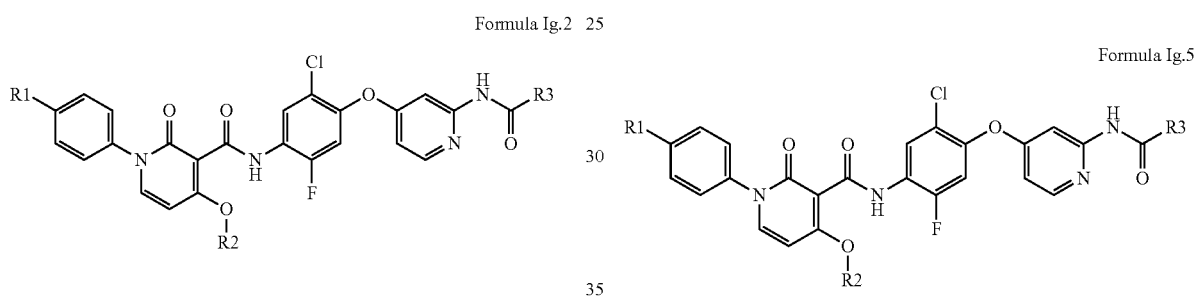

wherein
R1, R2, R4, R5, R6, R7, R8, m, and p are as broadly defined above for Formula I; and
R3 is C1-C6 alkyl, C3-C8 branched alkyl, or C3-C8 cycloalkyl.

In some embodiments, compounds of the Formula Ig are compounds of the Formula Ig.3:

Formula Ig.3

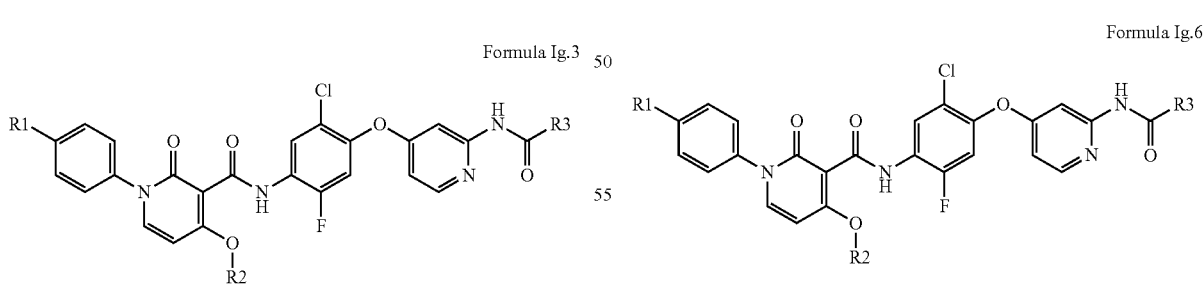

wherein
R1, R2, R4, R5, R6, R7, R8, m, and p are as broadly defined above for Formula I; and
R3 is —NR6(R7) or R4.

In some embodiments, compounds of the Formula Ig are compounds of the Formula Ig.4:

Formula Ig.4 wherein
R2, R3, R4, R5, R6, R7, R8, m, and p are as broadly defined above for Formula I; and
R1 is fluoro or H.

In some embodiments, compounds of the Formula Ig are compounds of the Formula Ig.5:

Formula Ig.5 wherein
R1, R3, R4, R5, R6, R7, R8, m, and p are as broadly defined above for Formula I; and
R2 is C1-C6 alkyl or C3-C8 branched alkyl.

In some embodiments, compounds of the Formula Ig are compounds of the Formula Ig.6:

Formula Ig.6 wherein
R4, R5, R6, R7, R8, m, and p are as broadly defined above for Formula I; and R1 is fluoro or H, R2 is C1-C6 alkyl or C3-C8 branched alkyl, and R3 is C1-C6 alkyl, C3-C8 branched alkyl, C3-C8 cycloalkyl, or —NR6(R7) or R4.

In some embodiments, compounds of the Formula Id are compounds of the Formula Ih:

Formula Ih

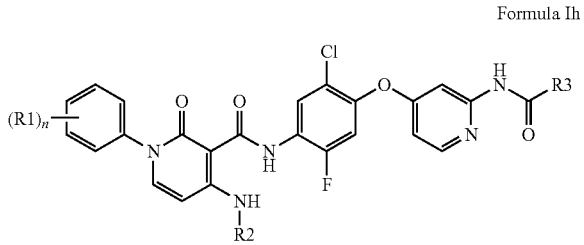

wherein
R1, R2, R3, R4, R5, R6, R7, R8, m, n, and p are as broadly defined above for Formula I.

In some embodiments, compounds of the Formula Ih are compounds of the Formula Ih.1:

Formula Ih.1

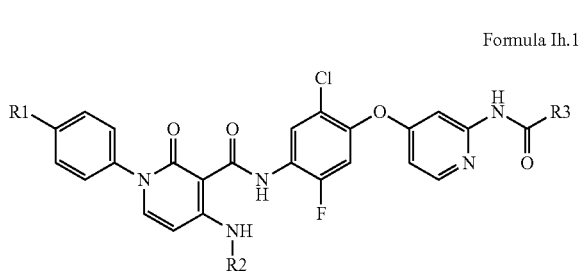

wherein
R1, R2, R3, R4, R5, R6, R7, R8, m, and p are as broadly defined above for Formula I.

In some embodiments, compounds of the Formula Ih are compounds of the Formula Ih.2:

Formula Ih.2

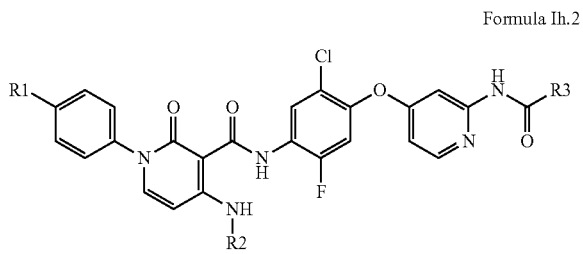

wherein
R1, R2, R4, R5, R6, R7, R8, m, and p are as broadly defined above for Formula I; and
R3 is C1-C6 alkyl, C3-C8 branched alkyl, or C3-C8 cycloalkyl.

In some embodiments, compounds of the Formula Ih are compounds of the Formula Ih.3:

Formula Ih.3

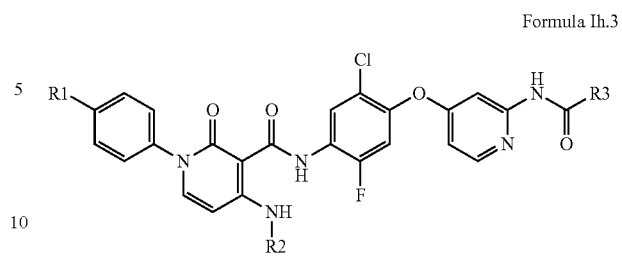

wherein
R1, R2, R4, R5, R6, R7, R8, m, and p are as broadly defined above for Formula I; and
R3 is —NR6(R7) or R4.

In some embodiments, compounds of the Formula Ih are compounds of the Formula Ih.4:

Formula Ih.4

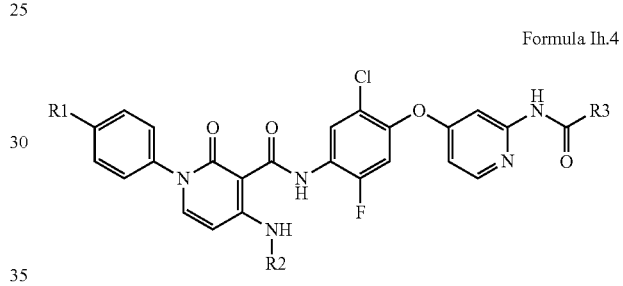

wherein
R2, R3, R4, R5, R6, R7, R8, m, and p are as broadly defined above for Formula I; and
R1 is fluoro or H.

In some embodiments, compounds of the Formula Ih are compounds of the Formula Ih.5:

Formula Ih.5

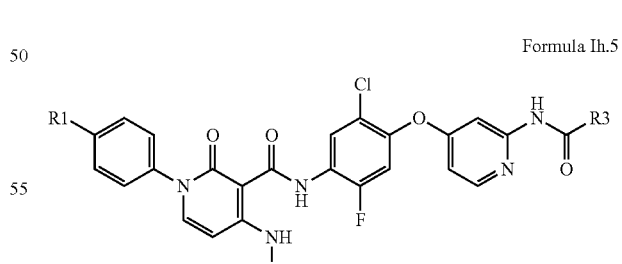

wherein
R1, R3, R4, R5, R6, R7, R8, m, and p are as broadly defined above for Formula I; and
R2 is C1-C6 alkyl or C3-C8 branched alkyl.

In some embodiments, compounds of the Formula Ig are compounds of the Formula Ih.6:

Formula Ih.6

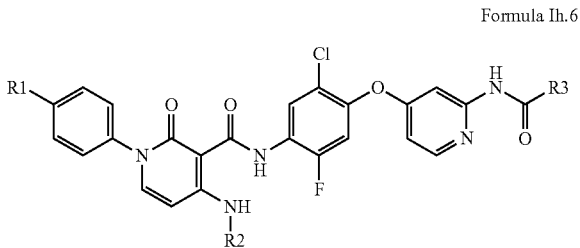

wherein
R4, R5, R6, R7, R8, m, and p are as broadly defined above for Formula I; and R1 is fluoro or H, R2 is C1-C6 alkyl or C3-C8 branched alkyl, and R3 is C1-C6 alkyl, C3-C8 branched alkyl, C3-C8 cycloalkyl, or —NR6(R7) or R4.

The following embodiments are descriptive of Formula I, Formula Ia, Formula Ia.1, Formula Ia.2, Formula Ia.3, Formula Ia.4, Formula Id, Formula Id.1, Formula Id.2, Formula Id.3, Formula Id.4.

In some embodiments, each X1 and X2 is individually and independently halogen. In other embodiments, each X1 and X2 is individually and independently F or Cl. In further embodiments, each X1 and X2 is F.

In some embodiments, each R1 is individually and independently halogen. In other embodiments, each R1 is individually and independently F or H. In further embodiments, each R1 is F.

In some embodiments, n is 1 and R1 is halogen. In other embodiments, n is 1 and R1 is F or H. In further embodiments, n is 1 and R1 is F.

In some embodiments, each R1, X1 and X2 is individually and independently halogen. In other embodiments, each R1, X1 and X2 is individually and independently F or Cl. In further embodiments, each R1, X1 and X2 is F.

In some embodiments, n is 1 and each R1, X1 and X2 is individually and independently halogen. In other embodiments, n is 1 and each R1, X1 and X2 is individually and independently F or Cl. In further embodiments n is 1 and each R1, X1 and X2 is F.

Utility

Compounds described herein find utility in the treatment of mammalian cancers and especially human cancers including, but not limited to, solid tumors, gastric cancers, melanomas, glioblastomas, ovarian cancer, pancreatic cancer, prostate cancer, lung cancers, non small cell lung cancer, breast cancers, kidney cancers, cervical carcinomas, metastasis of primary tumor sites, colonic cancers, myeloproliferative diseases, diseases wherein the etiology or progression is dependent on c-MET kinase activity, or on the activity of oncogenic forms-, aberrant fusion protein forms, and mutant forms of c-MET kinase.

Compounds described herein find utility in the treatment of polycystic kidney disease and other related ciliopathies.

Administration of Compounds

In some embodiments, the compound is administered by a method selected from the group consisting of oral, parenteral, inhalation, and subcutaneous.

Treatment Methods

The disclosed methods also include treating individuals suffering from a condition selected from the group consisting of cancer, hyperproliferative diseases, metabolic diseases, neurodegenerative diseases or diseases characterized by angiogenesis. These methods comprise administering to such individuals compounds disclosed herein, and especially those of section 1, said diseases including, but not limited to, solid tumors, malignant melanomas, glioblastomas, ovarian cancer, pancreatic cancer, prostate cancer, lung cancers, breast cancers, kidney cancers, hepatic cancers, cervical carcinomas, metastasis of primary tumor sites, myeloproliferative diseases, leukemias, papillary thyroid carcinoma, non-small cell lung cancer, mesothelioma, hypereosinophilic syndrome, gastrointestinal stromal tumors, colonic cancers, ocular diseases characterized by hyperproliferation leading to blindness including various retinopathies, diabetic retinopathy and age-related macular degeneration and hypereosinophilic syndrome, a disease caused by c-MET kinase, oncogenic forms thereof, aberrant fusion proteins thereof and polymorphs thereof. The administration method is not critical, and may be from the group consisting of oral, parenteral, inhalation, and subcutaneous.

Pharmaceutical Preparations

The compounds disclosed herein may form a part of a pharmaceutical composition by combining one or more such compounds with a pharmaceutically acceptable carrier. Additionally, the compositions may include an additive selected from the group consisting of adjuvants, excipients, diluents, and stabilizers.

Methods of Making

The compounds of the invention are available by the general synthetic methods illustrated in the Schemes below and the accompanying examples.

Compounds I of the invention are assembled as illustrated in Scheme 1. In one embodiment, an acid of formula 2 is reacted with an amine of formula 4 in the presence of a standard peptide coupling reagent familiar to those skilled in the art to prepare an amide of formula 1. Suitable reagents for the conversion of 2 to 1 include TBTU (O-(benzotriazol-1-yl)-N,N,N',N'-tetramethyluronium tetrafluoroborate), PyBOP (benzotriazol-1-yloxy)tripyrrolidinophosphonium hexafluorophosphate), EDC (1-ethyl-3-(3-dimethylaminopropyl)carbodiimide hydrochloride) and BOP-Cl (bis(2-oxo-3-oxazolidinyl)phosphonic chloride). In another embodiment, an acid of formula 2 can be converted to an acid chloride of formula 3, for example by reaction with thionyl chloride. Further reaction of acid chloride 3 with amine 4 provides a compound of formula 1. In another embodiment, amine 5 is reacted with acid 2 or acid chloride 3, as described above, to provide intermediate chloride 6. Further reaction of chloride 6 with a carbonylamine of formula 7 in the presence of a palladium catalyst affords a compound of formula 1. Suitable conditions for the transformation of 6 to 1 include treatment with tris(dibenzylideneacetone)dipalladium(0) [Pd$_2$(dba)$_3$] in the presence of a ligand, for example Xantphos, and a base, for example Cs$_2$CO$_3$, in a solvent, for example dioxane, at temperatures between ambient temp and 200° C., optionally with microwave irradiation.

Scheme 1

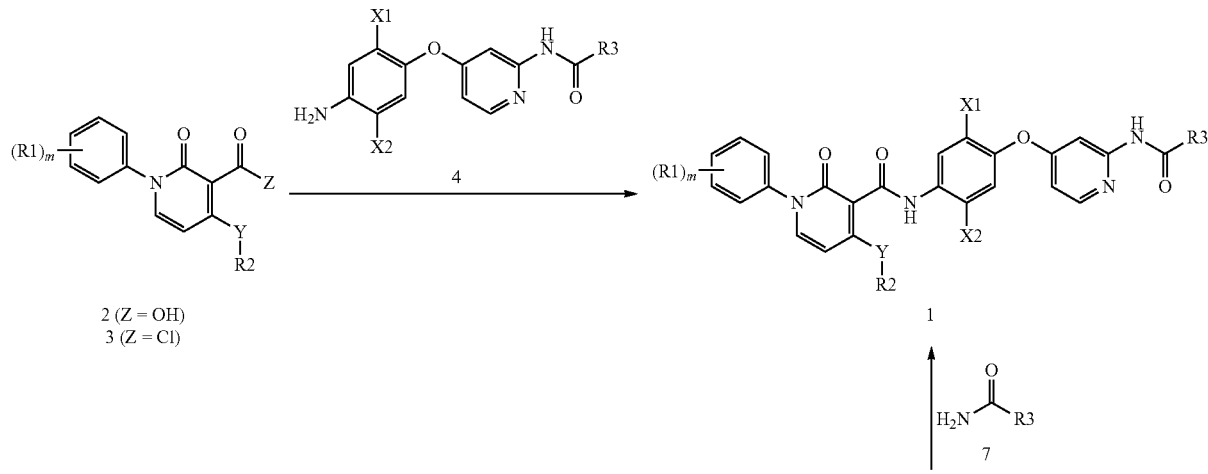

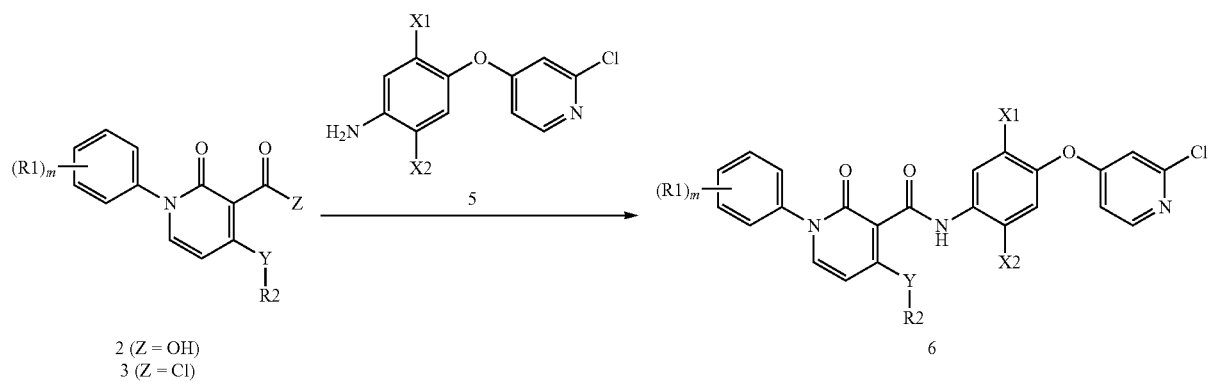

In other embodiments, a compound of formula 1 is prepared as illustrated in Scheme 2. Reaction of compound 6 with tert-butyl carbamate (8) in the presence of a palladium catalyst (as described in Scheme 1) affords compound 9. Removal of the tert-butyl carbamate protecting group upon exposure to acid, for example trifluoroacetic acid, provides intermediate 10. Reaction of amine 10 with reagent 11 (wherein Z is a leaving group or other activating group for an acylation/carbonylation reaction) provides a compound of formula 1. In one embodiment, the Z moiety of 11 is a halide. In another embodiment, reagent 11 is an activated ester or carbamate or an anhydride or mixed anhydride (Z is a fragment linked to the —(CO)R3 moiety of 11 with an oxygen atom). In another embodiment, the Z moiety of 11 is imidazole. Conditions for the transformation of 10 to 1 include the optional addition of a base, for example pyridine or 4-dimethylaminopyridine (DMAP).

In another embodiment, a compound of formula 14 [a subset of formula 1 wherein R3 is NR6(R7)] can be prepared from activated carbamate 12, which is in turn prepared by the treatment of amine 10 with a suitable chloroformate 16. In one embodiment, the R group of 16 and 12 is 2-propenyl. In another embodiment, the R group of 16 and 12 is 2,2,2-trichloroethyl. In another embodiment the R group of 16 and 12 is aryl, for example phenyl or 4-nitrophenyl. Treatment of actviated carbamate 12 with amine 13 provides a urea of formula 14. Suitable conditions for the transformation of 12 to 14 include mixing with amine 13 in a polar aprotic solvent, such as THF, optionally in the presence of an additional base, for example N-methylpyrrolidine, and optionally with heating and/or microwave irradiation. In another embodiment, a compound of formula 14 wherein R6 is hydrogen can be prepared directly from amine 10 by treatment with isocyanate 15.

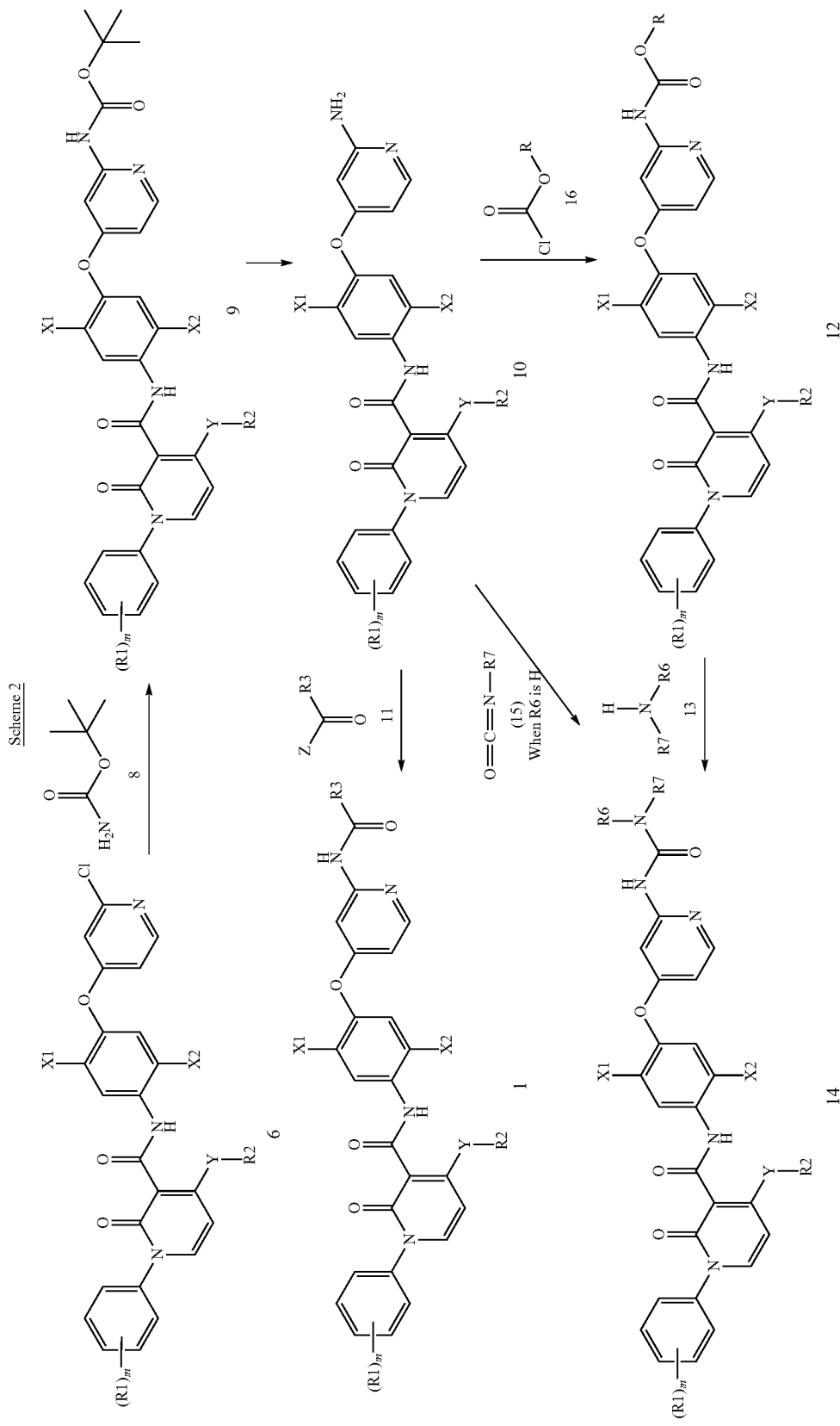
Scheme 2

In another embodiment (Scheme 3), a compound of formula 1 can be prepared from a halide of formula 19 (W is halogen) by reaction with reagent 20 (wherein Y is NH or O). Intermediate 19 is prepared from acid 17 or acid chloride 18 using the conditions of Scheme 1.

one embodiment (wherein Y is O), said transformation represents a net "trans-etherification" in which an R2* alkyl moiety is converted into a different R2 moiety. In another embodiment (Y is NH), said transformation represents the conversion of an alkoxy to an aminoalkyl moiety. In a similar

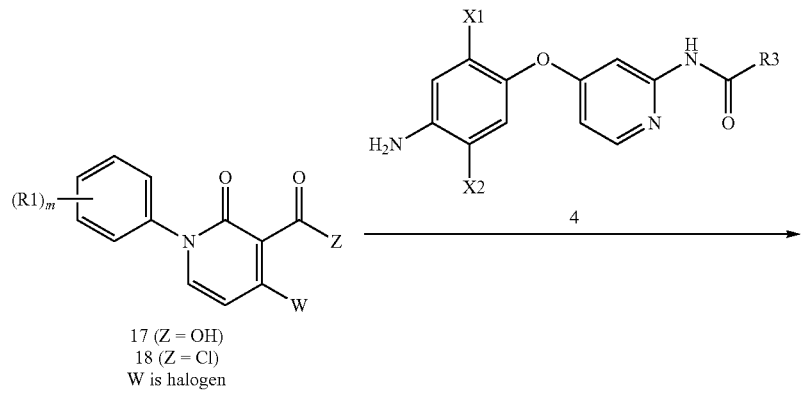

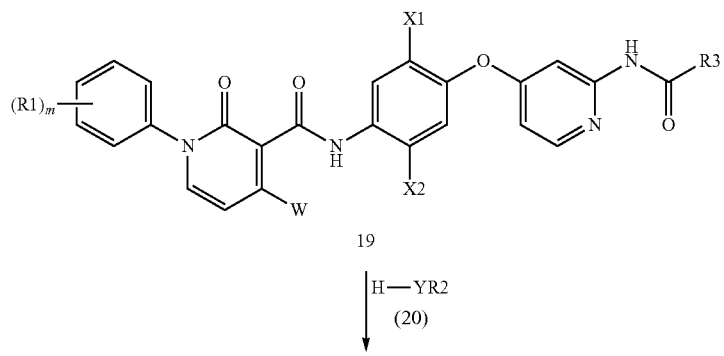

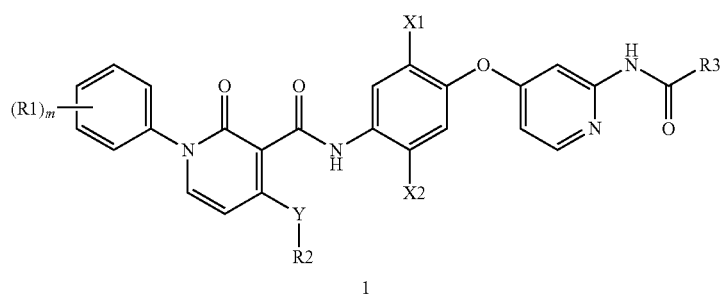

In a similar manner, a compound of formula 1 can also be prepared from an ether of formula 21 (wherein R2* is alkyl) by reaction with a compound of formula 20 (Scheme 4). In manner, intermediate 22 can be reacted with 20 to provide compound 6, which in turn can be converted to formula 1 as described in Scheme 1.

Scheme 4

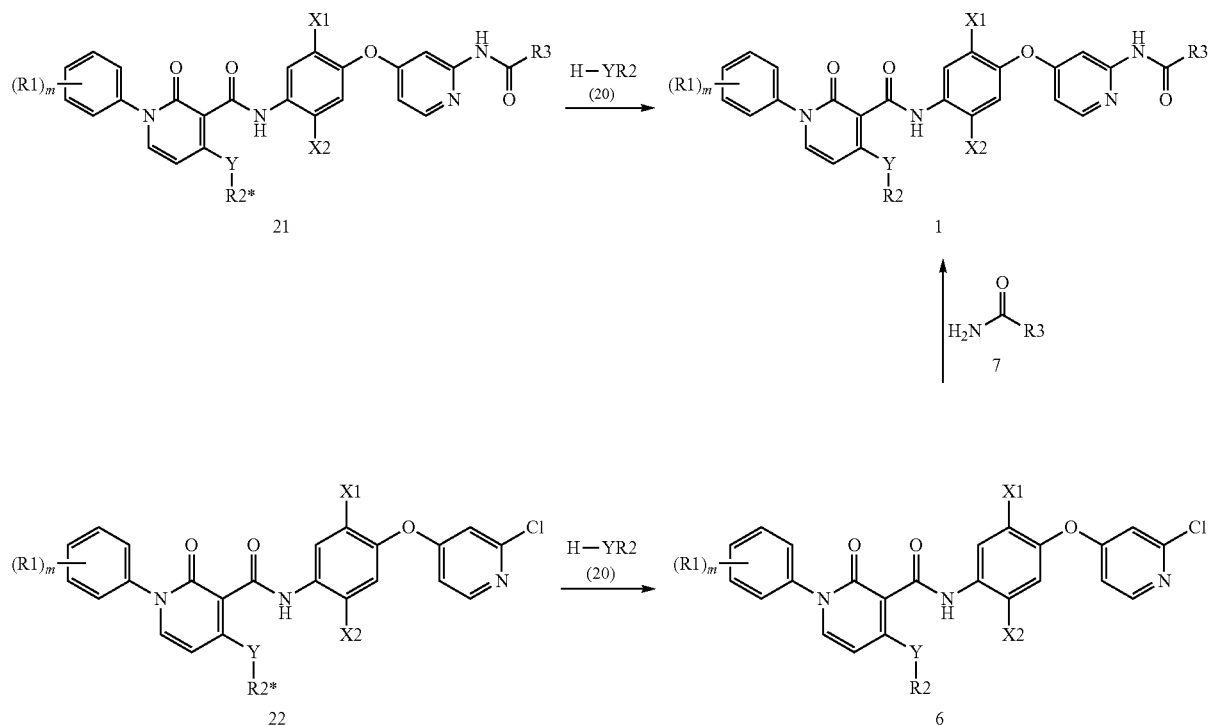

Amines 4 and 5 useful for the invention are synthesized as indicated below in Scheme 5. In one embodiment, amines 4 and 5 are prepared by a stepwise sequence commencing with the reaction of 4-fluoro-nitrobenzene 23 with 2-chloro-4-hydroxypyridine (24) in the presence of a base to provide the nitro-chloropyridine 25. This nucleophilic substitution reaction is typically performed in an aprotic solvent at temperatures ranging from ambient temp to 200° C., optionally with microwave heating. Additional conditions include the addition of a base, for example potassium carbonate, potassium tert-butoxide or sodium hydride. Reduction of the nitro group of 25 under standard reducing conditions provides amine 5. Examples of suitable conditions for the conversion of 25 to 5 include Raney nickel and hydrogen, iron powder/ammonium chloride, or zinc powder/ammonium chloride. Further reaction of chloropyridine 5 with a compound of formula 7 in the presence of a palladium catalyst provides a compound of formula 4. Alternately, compound 4 can be prepared from compound 25 by first reacting with compound 7 to provide 26. Subsequent reduction of the nitro moiety of 26 as described above provides 4.

In another embodiment, an amine of formula 5 can be prepared by the reaction of 4-aminophenol 27 with 2,4-dichloropyridine (28). This nucleophilic substitution reaction is typically performed in an aprotic solvent at temperatures ranging from ambient temp to 200° C., optionally with microwave heating. Additional conditions include the addition of a base, for example potassium carbonate, potassium tert-butoxide or sodium hydride.

Scheme 5

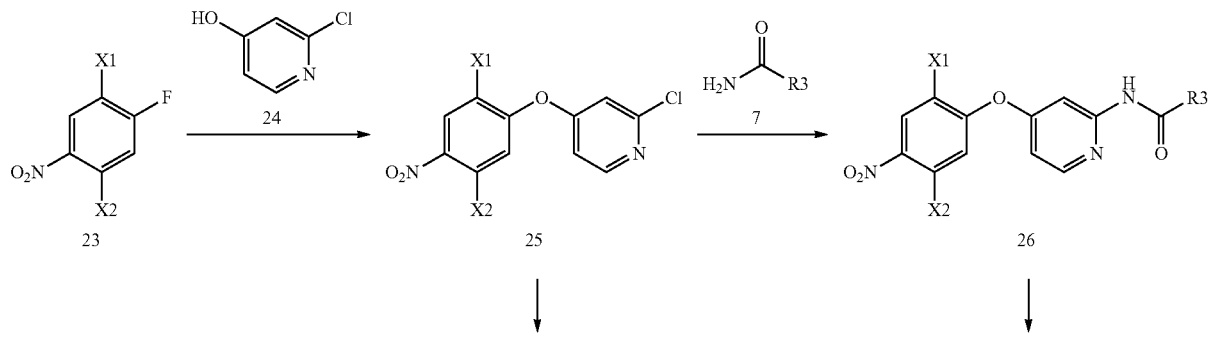

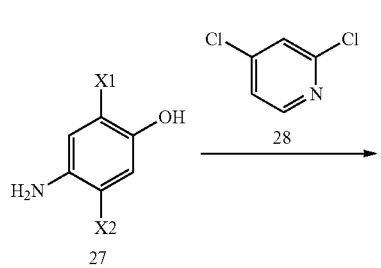
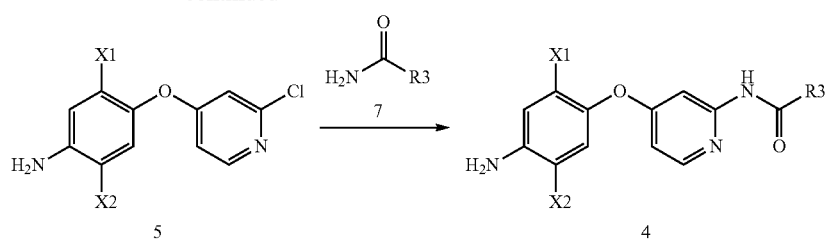

General pyridine acid 2 is prepared as indicated in Schemes 6 and 7. In one embodiment, acid 2 can be prepared by the sequence illustrated in Scheme 6. Condensation of ethyl cyanoacetate (28) with a trialkyorthoformate 29 provides a compound of formula 30. Further reaction of 30 with a dialkylacetal of dimethylformamide 31 [for example, dimethylformamide dimethylacetal (R=CH$_3$)] provides 32. Cyclization of 32 upon treatment with an acid, for example acetic acid, provides pyridone 33. Reaction of pyridone 33 with an arylboronic acid 34 in the presence of copper(II) acetate and pyridine affords N-aryl pyridone 35. Saponification of 35 under standard conditions, for example LiOH in aqueous ethanol, affords acid 36, an example of general acid 2 in which Y—R2 is O—R2* (wherein R2* is alkyl). Further conversion of the OR2* moiety of 36 to the Y—R2 moiety of 2 is accomplished, if needed, by treatment of 36 with a compound of formula 20, optionally in the presence of a base, for example potassium carbonate.

Scheme 6

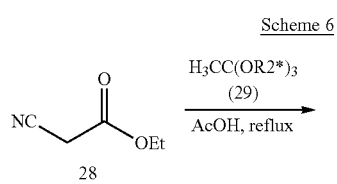
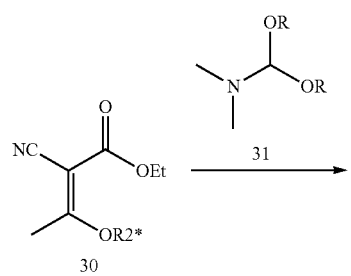
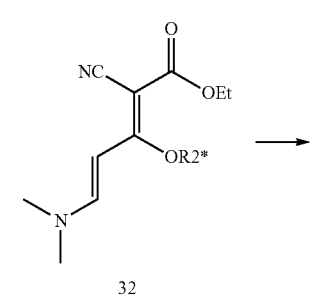

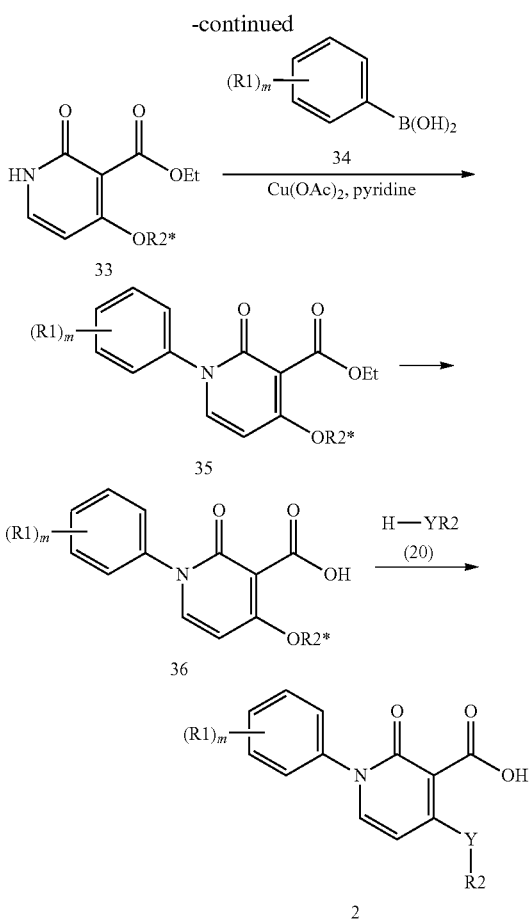

In another embodiment, general acid 2 can be prepared from an acid of formula 40 as illustrated in Scheme 7. Thus, 4-iodo-2-methoxynicotinaldehyde (37; See: WO95/29917) is de-methylated, for example by treatment with iodotrimethylsilane, to provide 2-hydroxy-4-iodonicotinaldehyde (38). Reacton of 38 with arylboronic acid 34 in the presence of copper(II) acetate and pyridine affords N-aryl pyridone aldehyde 39. Oxidation of 39 using sodium chlorite provides acid 40. Alternately, treatment of methyl 2-hydroxy-4-iodonicotinate (41) with arylboronic acid 34 in the presence of copper (II) acetate and pyridine affords N-aryl pyridone ester 42. Saponification of 42 under standard conditions, for example sodium hydroxide, affords acid 40. Treatment of iodo acid 40 with a compound of formula 20, optionally in the presence of a base, for example potassium carbonate, and/or optionally with heating, provides acid 2. Additionally, acid 40 can be used as a general example of acid 17 (W is Iodo, Scheme 3).

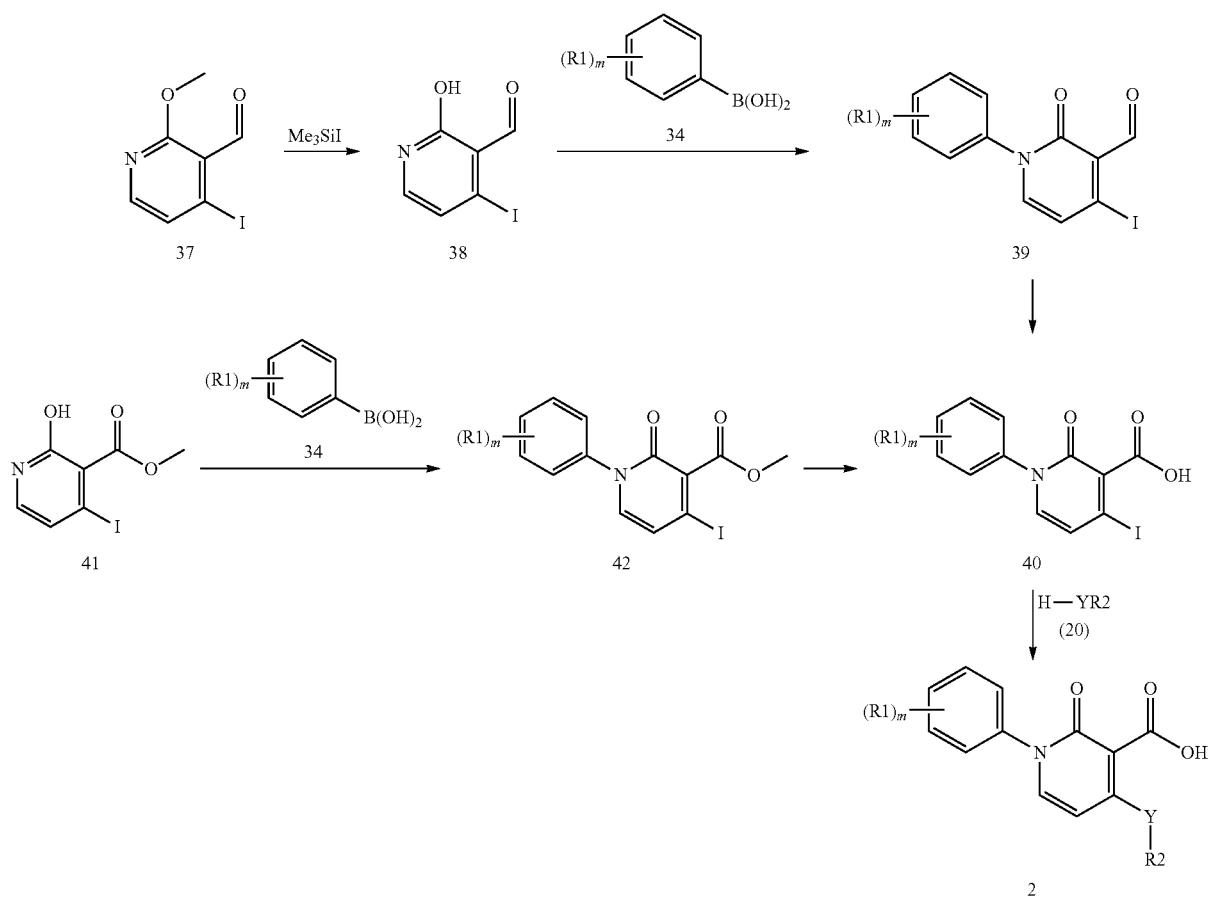

Scheme 7

Using the synthetic procedures and methods described herein and methods known to those skilled in the art, the following compounds were made:

N-(4-((2-acetamidopyridin-4-yl)oxy)-2,5-difluorophenyl)-4-ethoxy-1-(4-fluorophenyl)-2-oxo-1,2-dihydropyridine-3-carboxamide;

N-(2,5-difluoro-4-((2-propionamidopyridin-4-yl)oxy)phenyl)-4-ethoxy-1-(4-fluorophenyl)-2-oxo-1,2-dihydropyridine-3-carboxamide;

N-(4-((2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide;

N-(2,5-difluoro-4-((2-pivalamidopyridin-4-yl)oxy)phenyl)-4-ethoxy-1-(4-fluorophenyl)-2-oxo-1,2-dihydropyridine-3-carboxamide;

N-(2,5-difluoro-4-((2-isobutyramidopyridin-4-yl)oxy)phenyl)-4-ethoxy-1-(4-fluorophenyl)-2-oxo-1,2-dihydropyridine-3-carboxamide;

N-(4-((2-(cyclopropanecarboxamido)pyridin-4-yl)oxy)-2,5-difluorophenyl)-4-(ethylamino)-1-(4-fluorophenyl)-2-oxo-1,2-dihydropyridine-3-carboxamide;

N-(4-((2-acetamidopyridin-4-yl)oxy)-2,5-difluorophenyl)-1-(4-fluorophenyl)-4-(methylamino)-2-oxo-1,2-dihydropyridine-3-carboxamide;

N-(4-((2-acetamidopyridin-4-yl)oxy)-2,5-difluorophenyl)-4-(ethylamino)-1-(4-fluorophenyl)-2-oxo-1,2-dihydropyridine-3-carboxamide;

N-(4-((2-acetamidopyridin-4-yl)oxy)-2,5-difluorophenyl)-1-(4-fluorophenyl)-4-isopropoxy-2-oxo-1,2-dihydropyridine-3-carboxamide;

N-(2,5-difluoro-4-((2-propionamidopyridin-4-yl)oxy)phenyl)-1-(4-fluorophenyl)-4-isopropoxy-2-oxo-1,2-dihydropyridine-3-carboxamide;

1-(4-(2,5-difluoro-4-(1-(4-fluorophenyl)-4-(methylamino)-2-oxo-1,2-dihydropyridine-3-carboxamido)phenoxy)pyridin-2-yl)-3-methylurea;

N-(4-((2-acetamidopyridin-4-yl)oxy)-5-chloro-2-fluorophenyl)-4-ethoxy-1-(4-fluorophenyl)-2-oxo-1,2-dihydropyridine-3-carboxamide;

N-(5-chloro-2-fluoro-4-((2-propionamidopyridin-4-yl)oxy)phenyl)-4-ethoxy-1-(4-fluorophenyl)-2-oxo-1,2-dihydropyridine-3-carboxamide;

N-(5-chloro-4-(2-(cyclopropanecarboxamido)pyridin-4-yl)oxy)-2-fluorophenyl)-4-ethoxy-1-(4-fluorophenyl)-2-oxo-1,2-dihydropyridine-3-carboxamide;

N-(4-((2-(3,3-dimethylureido)pyridin-4-yl)oxy)-2,5-difluorophenyl)-4-ethoxy-1-(4-fluorophenyl)-2-oxo-1,2-dihydropyridine-3-carboxamide;

and N-(2,5-difluoro-4-((2-propionamidopyridin-4-yl)oxy)phenyl)-4-(ethoxy-d5)-1-(4-fluorophenyl)-2-oxo-1,2-dihydropyridine-3-carboxamide.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

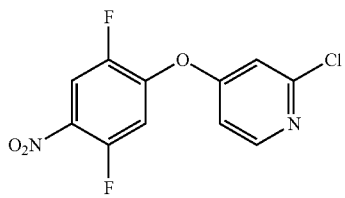 [SMILES: O=[N+]([O-])c1cc(F)c(Oc2ccnc(Cl)c2)cc1F]

Example A1

To a solution of 2-chloropyridin-4-ol (100 g, 772 mmol) in anhydrous DMF (2 L) was added $K_2CO_3$ (128 g, 926 mmol) in one portion at RT. The mixture was stirred for 10 min at RT, and was then treated with 1,2,4-trifluoro-5-nitrobenzene (88 mL, 772 mmol) slowly over 10 min. The internal temp of the reaction mixture was maintained below 24° C. during the addition. The reaction was stirred at RT for 1 h and then it was stopped by adding ice/water (10 L). The mixture was stirred for 2 h and then filtered to remove the solids. The solids were washed with water (5 L), hexanes (3 L) and then dried under vacuum at 50° C. to give 194.7 g of crude material. The solids were treated with MTBE (200 mL), stirred for 2 h, collected by filtration, washed with MTBE (50 mL) and dried under vacuum at 40° C. for 3 h to afford 2-chloro-4-(2,5-difluoro-4-nitrophenoxy)pyridine (164.6 g, 74.5% yield). $^1$H NMR (400 MHz, DMSO-$d_6$): δ 8.48 (dd, J=10.2, 7.0 Hz, 1H), 8.41 (d, J=5.6 Hz, 1H), 7.90 (dd, J=11.6, 6.7 Hz, 1H), 7.41 (d, J=2.1 Hz, 1H), 7.26 (dd, J=5.6, 2.4 Hz, 1H); MS (ESI): m/z 287.0 (M+H$^+$).

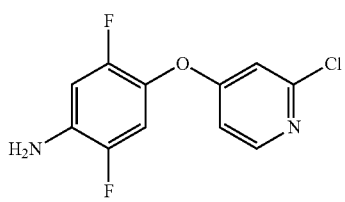

Example A2

In a Parr Shaker flask was combined Example A1 (11.68 g, 40.8 mmol) and MeOH (200 mL) under argon. Raney Ni (50% wet, 0.955 g, 8.15 mmol) was added. The argon was removed and replaced with hydrogen (10-20 psi) and the reaction mixture was shaken under hydrogen for 4 h. The completed reaction mixture was filtered through a pad of diatomaceous earth and the filtrate was concentrated to dryness to provide 4-(2-chloropyridin-4-yloxy)-2,5-difluoroaniline (8.2 g, 72% yield). $^1$H NMR (400 MHz, DMSO-$d_6$): δ 8.28 (d, J=5.9 Hz, 1H), 7.25 (dd, J=11.2, 7.5 Hz, 1H), 7.02 (dd, J=2.2 Hz, 1H), 6.95 (dd, J=5.8, 2.0 Hz, 1H), 6.74 (dd, J=12.3, 8.3 Hz, 1H), 5.57 (s, 2H); MS (ESI): m/z 257.0 (M+H$^+$).

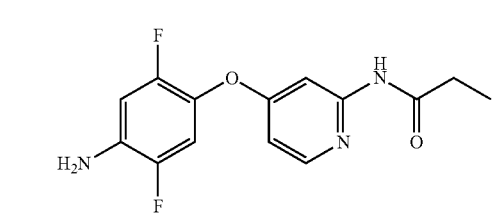 [SMILES: CCC(=O)Nc1cc(Oc2cc(F)c(N)cc2F)ccn1]

Example A3

A solution of Example A1 (35 g, 122 mmol) in anhydrous 1,4-dioxane (900 mL) was degassed with nitrogen for 10 min and to it was added propionamide (10.5 g, 143 mmol), 1,1'-bis(diphenylphosphino) ferrocene (dppf, 6.6 g, 12.0 mmol, 0.1 equiv.), $Cs_2CO_3$ (58.4 g, 179 mmol) and $Pd_2(dba)_3$ (5.47 g, 5.97 mmol). The mixture was degassed with nitrogen for another 15 min and then heated to 85° C. (internal temp) and stirred at that temp for 4 h. The reaction mixture was cooled to RT, filtered through a bed of diatomaceous earth and washed with EtOAc (1 L). The combined filtrates were concentrated under reduced pressure and purified by a silica gel chromatography (EtOAc/hexanes) to afford 30 g. This material was further purified by a trituration with diisopropyl ether (600 mL) and drying under vacuum at 40° C. to provide N-(4-(2,5-difluoro-4-nitrophenoxy)pyridin-2-yl)propionamide (27.2 g, 69% yield). MS (ESI): m/z 324.1 (M+H$^+$). This material was carried to next step without further purification.

To a suspension of N-(4-(2,5-difluoro-4-nitrophenoxy)pyridin-2-yl)propionamide (27.2 g, 84.2 mmol) in EtOH (750 mL) was added a solution of $NH_4Cl$ (18 g, 337 mmol) in water (188 mL) and Fe powder (97%, 325 mesh, 18.8 g, 337 mmol) in one portion at RT. The mixture was then heated at 80° C. for 1 h, cooled to ambient temp, filtered through a bed of diatomaceous earth, and washed with MeOH (1 L). The combined filtrates were concentrated to dryness and purified by silica gel chromatography (EtOAc/hexanes) to give N-(4-(4-amino-2,5-difluorophenoxy)pyridin-2-yl)propionamide (17.4 g, 70.5% yield). $^1$H-NMR (400 MHz, $CDCl_3$): δ 8.07 (d, J=5.6 Hz, 1H), 8.00 (br s, 1H), 7.77 (d, J=2 Hz, 1H), 6.85 (dd, J=10.4, 7.2 Hz, 1H), 6.63-6.58 (m, 2H), 3.79 (s, 2H), 2.38 (q, J=7.6 Hz, 2H), 1.20 (t, J=7.6 Hz, 3H); MS (ESI): m/z 294.1 (M+H$^+$).

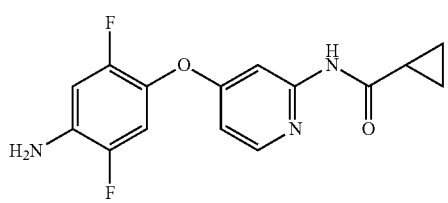 [SMILES: Nc1cc(F)c(Oc2ccnc(NC(=O)C3CC3)c2)cc1F]

Example A4

A mixture of Example A2 (100 mg, 0.39 mmol), cyclopropanecarboxamide (100 mg, 1.17 mmol), Xantphos [4,5-bis(diphenylphosphino)-9,9-dimethylxanthene] (23 mg, 0.039 mmol), $Cs_2CO_3$ (254 mg, 0.78 mmol) and $Pd_2(dba)_3$ (22 mg, 0.023 mmol) in dioxane (10 mL) was heated at 100° C. for 2 hours. The mixture was cooled to RT and filtered to remove inorganic salts. The filtrate was concentrated under vacuum. The residue was diluted with water (100 mL) and extracted with EtOAc (3×100 mL). The combined organics were washed with brine, dried over $Na_2SO_4$ and concentrated in vacuo. The crude product was purified by silica gel chromatography to afford N-(4-(4-amino-2,5-difluorophenoxy)pyridin-2-yl)cyclopropanecarboxamide (56 mg, 47% yield). MS (ESI): m/z 306.1 (M+H$^+$).

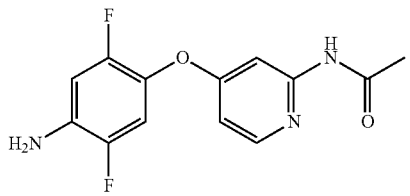 [SMILES: CC(=O)Nc1cc(Oc2cc(F)c(N)cc2F)ccn1]

Example A5

Using the procedure of Example A4, Example A2 (300 mg, 1.17 mmol), acetamide (207 mg, 3.51 mmol) Xantphos (68 mg, 0.12 mmol), $Cs_2CO_3$ (764 mg, 2.34 mmol) and $Pd_2(dba)_3$ (65 mg, 0.07 mmol) and dioxane (10 mL) were combined to give N-(4-(4-amino-2,5-difluorophenoxy)pyridin-2-yl)acetamide as a white solid (250 mg, 76.4% yield). $^1$H NMR (400 MHz, DMSO-d$_6$): δ 10.55 (s, 1H), 8.15 (d, J=5.6 Hz, 1H), 7.62 (d, J=2.4 Hz, 1H), 7.16 (dd, J=11.2, 7.6 Hz, 1H), 6.76 (dd, J=12.0, 8.0 Hz, 1H), 6.64 (dd, J=6.0, 2.4 Hz, 1H), 5.54 (s, 2H), 2.04 (s, 3H).

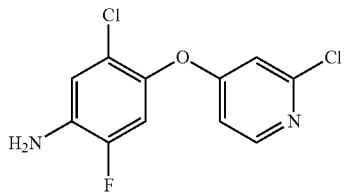 [SMILES: Nc1cc(Cl)c(Oc2ccnc(Cl)c2)cc1F]

Example A6

Method 1: To a solution of 2-chloro-5-fluorophenol (5.0 g; 34 mmol) in EtOH (125 mL) was added ferric nitrate (14.06 g, 34 mmol). The resulting mixture was heated at 50-55° C. for 3 h. The mixture was cooled to RT, diluted with water (50 mL), and extracted with EtOAc (3×50 mL). The combined organics were washed with water and brine and concentrated to dryness. Toluene (15 mL) was added to the residue and the mixture was heated to 50° C. for 10 min to give a clear solution. Then n-heptane was slowly added to the solution to effect precipitation while maintaining the temperature at 50° C. The resulting slurry was stirred at 50-55° C. for 30 min, then slowly cooled to 30-35° C. The solid was collected, was washed with n-heptane (15 mL), and dried in vacuo at 30-35° C. to give 2-chloro-5-fluoro-4-nitrophenol (2.95 g, 45% yield) as a fluffy solid.

Zinc dust (10 g, 160 mmol) was added portion wise to a solution of 2-chloro-5-fluoro-4-nitro-phenol (3.0 g, 16 mmol) and $NH_4Cl$ (8.4 g, 160 mmol) in THF (150 mL) and MeOH (150 mL) and the mixture was stirred at RT for 0.5 h. The reaction mixture was filtered, and the filter cake was washed with EtOAc (3×50 mL). The combined filtrate was washed with brine (3×100 mL), dried over $Na_2SO_4$ and concentrated to provide 4-amino-2-chloro-5-fluorophenol (2.5 g, 100% yield). $^1$H NMR (400 MHz, DMSO-d$_6$): δ 9.39 (s, 1H), 6.76 (d, J=9.2 Hz, 1H), 6.65 (d, J=12.4 Hz, 1H), 4.70 (s, 2H).

A solution of 4-amino-2-chloro-5-fluorophenol (6.0 g, 37 mmol), 2,4-dichloro-pyridine (5.3 g, 37 mmol) and $K_2CO_3$ (5.2 g, 37 mmol) in DMSO (100 mL) was heated at 80° C. under nitrogen overnight. The mixture was cooled to RT, poured into water (300 mL), and extracted with EtOAc (3×200 mL). The combined organics were washed with brine (3×100 mL), dried over $Na_2SO_4$, and concentrated in vacuo. The residue was purified by silica gel chromatography (EtOAc/petroleum ether) to give 5-chloro-4-(2-chloro-pyridin-4-yloxy)-2-fluoro-phenylamine as a white solid (3.0 g, 32% yield). $^1$H NMR (300 MHz, DMSO-d$_6$): δ 8.33 (d, J=5.7 Hz, 1H), 7.34-7.31 (m, 1H), 7.01-6.82 (m, 3H), 5.63 (br s, 2H).

Example A6, Method 2: A suspension of sodium hydride (60% in mineral oil) (0.620 g, 15.5 mmol) in dry DMF (30 mL) under argon was treated portion wise with 2-chloro-4-hydroxypyridine (1.34 g, 10.3 mmol) at 0° C. The mixture was stirred at 0° C. for 30 min, and then slowly warmed to RT. A solution of 5-chloro-2,4-difluoronitrobenzene (2 g, 10.3 mmol) in DMF (4.4 mL) was added to the suspension, and the mixture was heated at 90° C. for 15 h under argon. The mixture was cooled to RT, diluted with EtOAc (100 mL), washed with 10% aq LiCl (3×100 mL) and brine (2×100 mL), dried (MgSO$_4$), concentrated to dryness, and purified by silica gel chromatography (EtOAc/hexanes) to yield 2-chloro-4-(2-chloro-5-fluoro-4-nitrophenoxy)pyridine as a bright yellow oil (1.42 g, 45% yield). $^1$H NMR (400 MHz, DMSO-d$_6$): δ 8.56 (dd, 1H), 8.35 (dd, 1H), 7.88 (dd, 1H), 7.32 (dd, 1H), 7.18 (m, 1H); MS (ESI) m/z: 303.0 (M+H$^+$).

2-Chloro-4-(2-chloro-5-fluoro-4-nitrophenoxy)pyridine (1.31 g, 4.31 mmol) was dissolved in THF (108 mL) and MeOH (108 mL). Ammonium chloride (2.31 g, 43.1 mmol) was added, followed by zinc dust (2.82 g, 43.1 mmol). The reaction mixture was stirred at RT for 1 h. The solids were filtered through diatomaceous earth and the filtrate was concentrated under reduced pressure to yield 5-chloro-4-(2-chloropyridin-4-yloxy)-2-fluorobenzenamine as a brown solid which was used without purification assuming a 100% yield. MS (ESI) m/z: 273.0 (M+H$^+$).

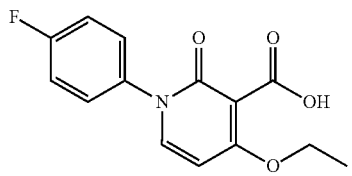 [SMILES: CCOc1ccn(-c2ccc(F)cc2)c(=O)c1C(=O)O]

Example B1

A mixture of ethyl 2-cyanoacetate (120 g, 1.06 mol) and triethylorthoacetate (354 g, 2.12 mol) in glacial acetic acid (33 g, 0.53 mol) was heated at 120-130° C. overnight. The mixture was concentrated under vacuum to provide crude ethyl 2-cyano-3-ethoxybut-2-enoate. The residue was carried into the next reaction without further purification assuming 100% conversion.

A mixture of ethyl 2-cyano-3-ethoxybut-2-enoate (194 g theory, 1.06 mol) and N,N-dimethylformamide dimethyl acetal (160 g, 1.325 mol) was heated at 70° C. for 2 h. The mixture was concentrated under high vacuum to provide crude ethyl 2-cyano-5-(dimethylamino)-3-ethoxypenta-2,4-dienoate. The residue was used directly without further purification.

A mixture of ethyl 2-cyano-5-(dimethylamino)-3-ethoxypenta-2,4-dienoate (150 g, 0.63 mol) and HOAc (600 mL) was refluxed overnight. The mixture was concentrated to dryness under high vacuum, treated with water (300 mL) and washed with EtOAc (2×250 mL) to remove the impurities. The pH of the aqueous was adjusted with $NaHCO_3$ to pH ~9-10. The mixture was extracted with DCM (3×300 mL). The combined organics were washed with brine, dried over $Na_2SO_4$ and concentrated. The residue was purified by silica gel chromatography to afford ethyl 4-ethoxy-2-oxo-1,2-dihydropyridine-3-carboxylate (90 g, 66.6% yield).

A mixture of ethyl 4-ethoxy-2-oxo-1,2-dihydropyridine-3-carboxylate (60 g, 0.284 mol), 4-fluoro phenylboronic acid (120 g, 0.853 mol), $Cu(OAc)_2$ (113 g, 0.568 mol) and pyridine (88 g, 1.137 mol) in DCM (500 mL) was stirred at RT for 4 h open to air. The reaction mixture was filtered and the solids were washed with water. The filtrate was extracted with DCM (2×250 mL). The combined organics were dried over $Na_2SO_4$ and concentrated to afford ethyl 4-ethoxy-1-(4-fluorophenyl)-2-oxo-1,2-dihydropyridine-3-carboxylate. The product was carried forward without further purification. (77 g, 95% yield).

A mixture of ethyl 4-ethoxy-1-(4-fluorophenyl)-2-oxo-1,2-dihydropyridine-3-carboxylate (60 g, 0.196 mol) and LiOH (30 g, 0.6 mol) in EtOH (200 mL) and water (100 mL) was stirred at RT for 16 h. The mixture was concentrated. The residue was diluted with water (300 mL) and was washed with EtOAc (100 mL). The aqueous layer was acidified to pH<2 with conc HCl and was extracted with EtOAc (3×300 mL). The extracts were washed with brine, dried over $Na_2SO_4$ and concentrated. Petroleum ether (PE) (200 mL) was added. The resultant precipitate was collected by filtration, washed with PE and dried to afford 4-ethoxy-1-(4-fluorophenyl)-2-oxo-1,2-dihydropyridine-3-carboxylic acid. (43 g, 78.9% yield). $^1H$ NMR (400 MHz, DMSO-$d_6$): δ 7.95 (d, J=8.0 Hz, 1H), 7.48 (m, 2H), 7.35 (m, 2H), 6.58 (d, J=7.6 Hz, 1H), 4.28 (q, J=7.2 Hz, 2H), 1.32 (t, J=7.2 Hz, 3H).

tic acid (44 g, 193 mmol) were combined in toluene (700 mL), treated 2,6-lutidine (45 mL, 385 mmol), and stirred vigorously for 1 day. Additional 4-fluorophenylboronic acid (5 g) was added and the reaction was stirred vigorously for an additional 3 days. The reaction mixture was concentrated and then suspended in 10% methanol/EtOAc. Diatomaceous earth was added and the mixture was stirred for 5 minutes. The mixture was filtered through a plug of diatomaceous earth. The filtrate was concentrated, and suspended in EtOAc and water. The mixture was again filtered through diatomaceous earth, rinsing forward with EtOAc. The filtrate was washed with 1N HCl, dried over $Na_2SO_4$, and concentrated under vacuum. The resulting solid was triturated with EtOAc to yield 1-(4-fluorophenyl)-4-iodo-2-oxo-1,2-dihydropyridine-3-carbaldehyde (8.0 g, 42% yield) as a yellow solid.

1-(4-fluorophenyl)-4-iodo-2-oxo-1,2-dihydropyridine-3-carbaldehyde (8 g, 23 mmol) and sodium phosphate monobasic (8 g, 58.4 mmol) were stirred vigorously in a mixture of THF (35 mL), tert-butanol (35 mL), and water (35 mL) at 0° C. 2-Methyl-2-butene (2.0 M in THF 36.1 mL, 72.2 mmol) was added to the reaction mixture, followed by sodium chlorite (4.8 g, 53.7 mmol). The ice bath was removed and the reaction mixture was warmed to RT and stirred vigorously for 1 h. 1N HCl (20 mL) was added. The mixture was stirred for 5 min. The solids were collected by filtration and washed with water, EtOAc, and ether. The layers of the filtrate were separated, the aqueous layer was extracted with EtOAc, and the combined organics were dried over $MgSO_4$ and concentrated in vacuo. The resulting solid was suspended in EtOAc, filtered, and washed with EtOAc and ether to yield additional product. The pale yellow solids (8.22 g) were combined, dissolved in a minimal amount of 1N aqueous NaOH, treated with EtOAc, and stirred vigourously for 5 min. The layers were separated, and the aqueous layer was washed with EtOAc. The aqueous layer was acidified to pH 1 with conc HCl. The pale yellow solid that precipitated out of solution was collected by filtration, washed with water, EtOAc, and ether, and dried under vacuum to afford 1-(4-fluorophenyl)-4-iodo-2-oxo-1,2-dihydropyridine-3-carboxylic acid (5.4 g, 64.5% yield). $^1H$ NMR (400 MHz, DMSO-$d_6$): δ 13.5 (s, 1H), 7.43-7.47 (m, 3H), 7.30-7.35 (m, 2H), 6.76 (d, J=7.2 Hz, 1H).

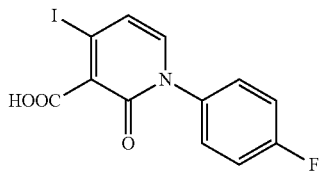 [SMILES: O=C(O)c1c(I)ccn(-c2ccc(F)cc2)c1=O]

Example B2

4-Iodo-2-methoxynicotinaldehyde (25 g, 83 mmol, prepared according to WO95/29917) and sodium iodide (37.0 g, 249 mmol) were combined in MeCN (500 mL). Chlorotrimethylsilane (31.4 mL, 249 mmol) was added dropwise over 15 min. The reaction mixture was stirred at RT for 2 h and then concentrated under vacuum. The crude product was suspended in a mixture of EtOAc, water, and saturated aqueous $NaHCO_3$, then filtered to give a dark brown solid. This solid was triturated with MeCN to yield 4-iodo-2-oxo-1,2-dihydropyridine-3-carbaldehyde (12 g, yield 50.5%) as a yellow solid. MS (ESI) m/z: 250.0 (M+H$^+$).

4-Iodo-2-oxo-1,2-dihydropyridine-3-carbaldehyde (12.0 g, 48.3 mmol), 4-fluorophenylboronic acid (20.1 g, 144.7 mmol), copper(II) acetate (17.55 g, 96.75 mmol), and myris-

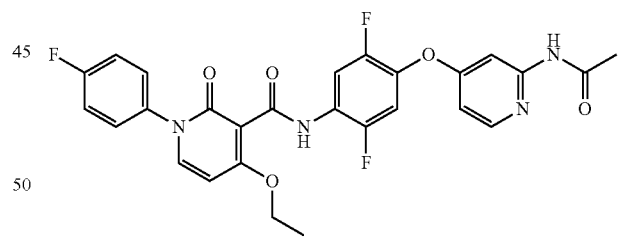

Example 1

A solution of Example B1 (35 g, 126 mmol) in toluene (400 mL) was treated with $SOCl_2$ (120 g, 1.01 mol) and one drop of DMF, and was heated to reflux for 2 h. The mixture was concentrated in vacuo to afford 4-ethoxy-1-(4-fluoro-phenyl)-2-oxo-1,2-dihydro-pyridine-3-carbonyl chloride (33.5 g, 100% yield). The residue was carried into the next reaction without further purification.

To a solution of Example A2 (29 g, 113 mmol) and triethylamine (23 g, 226 mmol) in THF (400 mL) was added freshly prepared 4-ethoxy-1-(4-fluoro-phenyl)-2-oxo-1,2-dihydro-pyridine-3-carbonyl chloride (33.5 g, 113 mmol) and the mixture was stirred at RT overnight. The mixture was concentrated in vacuo, and the residue was diluted with water (500 mL) and extracted with EtOAc (3×500 mL). The combined organics were washed with brine, dried over Na₂SO₄ and concentrated to afford N-(4-((2-chloropyridin-4-yl)oxy)-2,5-difluorophenyl)-4-ethoxy-1-(4-fluorophenyl)-2-oxo-1,2-dihydropyridine-3-carboxamide (51 g, 87% yield).

A mixture of N-(4-((2-chloropyridin-4-yl)oxy)-2,5-difluorophenyl)-4-ethoxy-1-(4-fluorophenyl)-2-oxo-1,2-dihydropyridine-3-carboxamide (36 g, 69.9 mmol), acetamide (12.4 g, 209 mmol), Xantphos (4 g, 6.9 mmol), Cs₂CO₃ (45.5 g, 140 mmol) and Pd₂(dba)₃ (3.84 g, 4.2 mmol) in dioxane (500 mL) was heated at 100° C. under nitrogen for 2 h. The reaction mixture was cooled to RT, filtered to remove inorganic salts, and concentrated under vacuum. The residue was treated with water (300 mL) and extracted with EtOAc (3×400 mL). The combined organics were washed with brine, dried over Na₂SO₄ and concentrated dryness. The residue was purified by silica gel chromatography to afford N-(4-((2-acetamidopyridin-4-yl)oxy)-2,5-difluorophenyl)-4-ethoxy-1-(4-fluorophenyl)-2-oxo-1,2-dihydropyridine-3-carboxamide (15 g, 44% yield). ¹H NMR (400 MHz, DMSO-d₆): δ 11.23 (s, 1H), 10.60 (s, 1H), 8.34 (dd, J=12.8, 7.2 Hz, 1H), 8.20 (d, J=5.6 Hz, 1H), 7.94 (d, J=8.0 Hz, 1H), 7.68 (s, 1H), 7.56-7.51 (m, 3H), 7.40-7.36 (m, 2H), 6.73 (dd, J=5.6, 2.4 Hz, 1H), 6.56 (d, J=8.0 Hz, 1H), 4.30 (q, J=6.8 Hz, 2H), 2.05 (s, 3H), 1.35 (t, J=6.8 Hz, 3H); MS (ESI) m/z: 539.1 (M+H⁺).

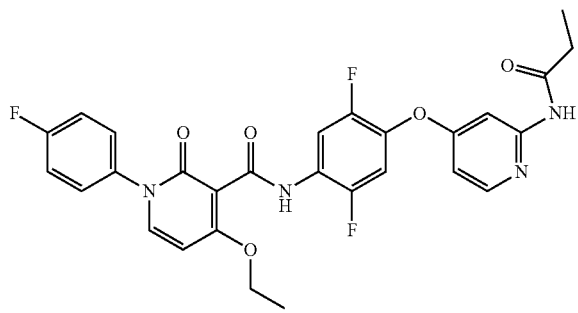 [SMILES: CCOc1ccn(-c2ccc(F)cc2)c(=O)c1C(=O)Nc1cc(F)c(Oc2ccnc(NC(=O)CC)c2)cc1F]

Example 2

A solution of Example B1, (5.2 g, 18.8 mmol) in SOCl₂ (50 mL, 685 mmol) was heated at 60° C. for 2 h. The mixture was azeotroped with toluene and concentrated to dryness. The solid was dissolved in DCM (150 mL), cooled to 0° C. and treated with a solution of Example A3 (5 g, 17.1 mmol) and pyridine (0.14 mL, 1.74 mmol) in DCM (100 mL) over 20 min. The reaction mixture was stirred at 0° C. for 10 min and then warmed to RT for 2 h. Water (5 mL) was added and the mixture was concentrated in vacuo. The residue was triturated with water (200 mL) and the solids were collected by filtration, washed with water and dried under vacuum. The solids were dissolved in DCM (400 mL), washed with saturated NaHCO₃ (2×100 mL) and brine (100 mL), dried over Na₂SO₄, and concentrated to dryness. The solids were triturated with hexanes/EtOAc (1:1), collected by filtration and dried under vacuum to give N-(2,5-difluoro-4-((2-propionamidopyridin-4-yl)oxy)phenyl)-4-ethoxy-1-(4-fluorophenyl)-2-oxo-1,2-dihydropyridine-3-carboxamide (7.5 g, 82.4% yield). ¹H NMR (400 MHz, DMSO-d₆): δ 11.22 (s, 1H), 10.52 (s, 1H), 8.33 (dd, J=12.6, 7.2 Hz, 1H), 8.18 (d, J=5.7 Hz, 1H), 7.92 (d, J=7.8 Hz, 1H), 7.68 (d, J=2.4 Hz, 1H), 7.50-7.48 (m, 3H), 7.36 (t, J=8.7 Hz, 2H), 6.72 (dd, J=5.7, 2.4 Hz, 1H), 6.55 (d, J=7.9 Hz, 1H), 4.28 (q, J=7.0 Hz, 2H), 2.33 (q, J=7.5 Hz, 2H), 1.34 (t, J=7.0 Hz, 3H), 0.99 (t, J=7.5 Hz, 3H); MS (ESI) m/z: 553.2 (M+H⁺).

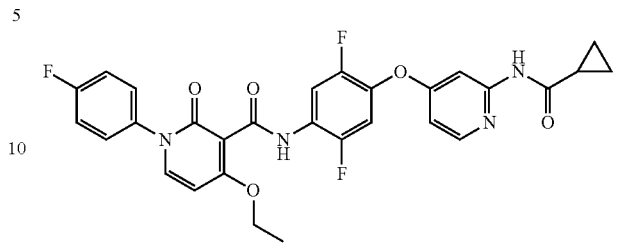

Example 3

A mixture of N-(4-((2-chloropyridin-4-yl)oxy)-2,5-difluorophenyl)-4-ethoxy-1-(4-fluorophenyl)-2-oxo-1,2-dihydropyridine-3-carboxamide (0.100 g, 0.194 mmol, see: Example 1), cyclopropanecarboxamide (0.033 g, 0.388 mmol), Cs₂CO₃ (0.095 g, 0.291 mmol) and Xantphos (5.05 mg, 8.72 μmmol) in dioxane (2 mL) was sparged with argon, treated with Pd₂(dba)₃ (2.66 mg, 2.91 μmmol), sparged again with argon, then fitted with a reflux condensor capped with an argon-filled balloon and heated to 100° C. overnight. The mixture was cooled to RT and partitioned between water and EtOAc. The organic layer was washed with brine, dried over MgSO4, concentrated to dryness and purified via silica gel chromatography (EtOAc/Hex) to afford N-(4-((2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide (33 mg, 30% yield) as a solid. MS (ESI) m/z: 565.2 (M+H+).

A suspension of N-(4-((2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide (0.029 g, 0.051 mmol) in MeCN (0.5 mL) was heated to 80° C., treated with methanesulfonic acid (3.34 μl, 0.051 mmol), then cooled to RT and stirred overnight. Ether was added drop wise until solids precipitated. The mixture was stirred for several hours. The solids were collected by filtration, rinsed with ether and dried under vacuum to afford N-(4-((2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide methanesulfonate (15 mg, 44% yield) as a white solid. ¹H NMR (400 MHz, DMSO-d₆): δ 11.22 (s, 1H), 10.99 (s, 1H), 8.33 (dd, J=12.6, 7.2 Hz, 1H), 8.20 (d, J=5.8 Hz, 1H), 7.92 (d, J=7.8 Hz, 1H), 7.63-7.45 (m, 4H), 7.36 (m, 2H), 6.79 (d, J=5.7 Hz, 1H), 6.55 (d, J=7.9 Hz, 1H), 4.28 (q, J=7.0 Hz, 2H), 2.29 (s, 3H), 1.93 (m, 1H), 1.33 (t, J=7.0 Hz, 3H), 0.77 (m, 4H); MS (ESI) m/z: 565.2 (M+H+).

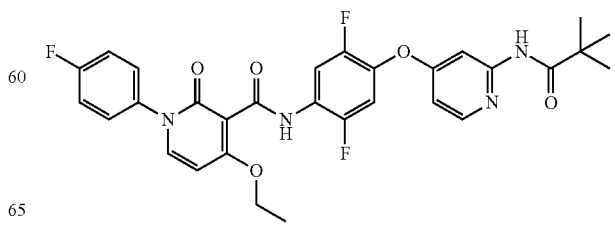

Example 4

N-(4-((2-chloropyridin-4-yl)oxy)-2,5-difluorophenyl)-4-ethoxy-1-(4-fluorophenyl)-2-oxo-1,2-dihydropyridine-3-carboxamide (0.15 g, 0.29 mmol, see: Example 1) was combined with pivalamide (0.12 g, 1.16 mmol), Xantphos (0.02 g, 0.033 mmol), and $Cs_2CO_3$ (0.14 g, 0.44 mmol) in dioxane (5 mL). The mixture was sparged with argon for several min, treated with $Pd_2(dba)_3$ (0.015 g, 0.016 mmol), and heated at 100° C. overnight. The mixture was cooled to RT and filtered, washing with dioxane. The filtrate was concentrated to dryness and the residue was purified by reverse-phase chromatography [10%-45% $CH_3CN/H_2O$ with 0.1% TFA]. The pure fractions were combined and co-evaporated with MeOH. The aqueous layer was neutralized with $NaHCO_3$ and extracted with EtOAc. The organic layer was washed with brine, dried over $Na_2SO_4$, and concentrated to obtain N-(2,5-difluoro-4-((2-pivalamidopyridin-4-yl)oxy)phenyl)-4-ethoxy-1-(4-fluorophenyl)-2-oxo-1,2-dihydropyridine-3-carboxamide (50 mg, 29.6% yield). $^1$H NMR (400 MHz, DMSO-$d_6$): δ 11.23 (s, 1H), 9.89 (s, 1H), 8.34 (dd, J=12.6, 7.2 Hz, 1H), 8.21 (d, J=5.7 Hz, 1H), 7.92 (d, J=7.8 Hz, 1H), 7.66 (d, J=2.4 Hz, 1H,) 7.51-7.48 (m, 3H), 7.36 (t, J=8.7 Hz, 2H), 6.76 (dd, J=5.7, 2.5 Hz, 1H), 6.55 (d, J=7.9 Hz, 1H), 4.28-4.27 (m, 2H), 1.34 (t, J=6.98 Hz, 3H), 1.05 (s, 9H); MS (ESI) m/z: 581.2 (M+H+).

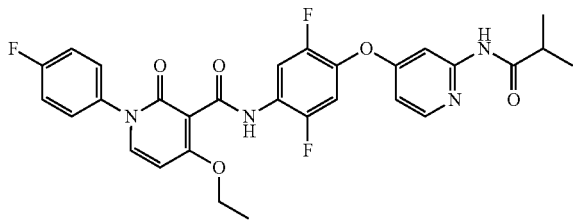 [SMILES: CCOc1ccn(-c2ccc(F)cc2)c(=O)c1C(=O)Nc1cc(F)c(Oc2ccnc(NC(=O)C(C)C)c2)cc1F]

Example 5

Using the procedure of Example 4, N-(4-((2-chloropyridin-4-yl)oxy)-2,5-difluorophenyl)-4-ethoxy-1-(4-fluorophenyl)-2-oxo-1,2-dihydropyridine-3-carboxamide (0.15 g, 0.29 mmol), isobutyramide (0.10 g, 1.16 mmol), Xantphos (0.02 g, 0.032 mmol), and $Cs_2CO_3$ (0.14 g, 0.44 mmol), $Pd_2(dba)_3$ (0.015 g, 0.015 mmol), and dioxane (5 mL) were combined to obtain N-(2,5-difluoro-4-((2-isobutyramidopyridin-4-yl)oxy)phenyl)-4-ethoxy-1-(4-fluorophenyl)-2-oxo-1,2-dihydropyridine-3-carboxamide (55 mg, 35% yield). $^1$H NMR (400 MHz, DMSO-$d_6$): δ 11.23 (s, 1H), 10.52 (s, 1H), 8.34-8.33 (m, 1H), 8.19 (d, J=5.7 Hz, 1H), 7.92 (d, J=7.8 Hz, 1H), 7.69 (d, J=2.4 Hz, 1H), 7.50-7.49 (m, 3H), 7.36 (t, J=8.7 Hz, 2H), 6.74 (dd, J=5.7, 2.5 Hz, 1H), 6.55 (d, J=7.9 Hz, 1H), 4.28 (q, J=7.0 Hz, 2H), 2.69 (m, 1H), 1.34 (t, J=7.0 Hz, 3H), 1.02 (d, J=6.8 Hz, 6H); MS (ESI) m/z: 581.2 (M+H+).

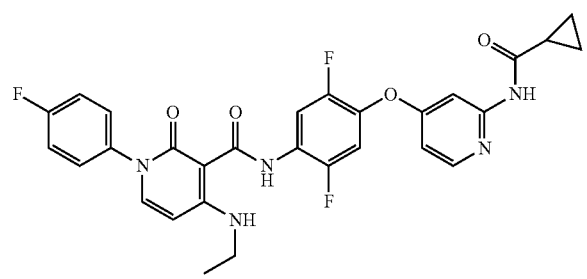 [SMILES: CCNc1ccn(-c2ccc(F)cc2)c(=O)c1C(=O)Nc1cc(F)c(Oc2ccnc(NC(=O)C3CC3)c2)cc1F]

Example 6

Example B2 (120 mg, 0.334 mmol), $SOCl_2$ (190 mg, 1.17 mmol) and one drop of DMF were combined in toluene (20 mL) and heated at reflux for 2 h. The mixture was concentrated under vacuum to afford 1-(4-fluorophenyl)-4-iodo-2-oxo-1,2-dihydropyridine-3-carbonyl chloride (120 mg, 95% yield), which was used without further purification.

A mixture of 1-(4-fluorophenyl)-4-iodo-2-oxo-1,2-dihydropyridine-3-carbonyl chloride (69 mg, 0.18 mmol), Example A4 (56 mg, 0.18 mmol) and DIEA (47 mg, 0.36 mmol) in THF (5 mL) was stirred at RT overnight. The mixture was concentrated to afford crude N-(4-((2-(cyclopropanecarboxamido)pyridin-4-yl)oxy)-2,5-difluorophenyl)-1-(4-fluorophenyl)-4-iodo-2-oxo-1,2-dihydropyridine-3-carboxamide (100 mg). This crude material mixture was treated with a methanolic solution of ethylamine (10 mL) and the mixture was heated at 80° C. for 3 hours. The mixture was concentrated in vacuo and the residue was purified by prep-HPLC to afford N-(4-((2-(cyclopropanecarboxamido)pyridin-4-yl)oxy)-2,5-difluorophenyl)-4-(ethylamino)-1-(4-fluorophenyl)-2-oxo-1,2-dihydropyridine-3-carboxamide (28 mg, 27.6% yield, 2 steps). $^1$H NMR (400 MHz, DMSO-$d_6$): δ 13.23 (s, 1H), 10.92 (s, 1H), 10.47 (m, 1H), 8.47 (m, 1H), 8.19 (d, J=5.8 Hz, 1H), 7.69 (m, 1H), 7.60 (s, 1H), 7.55-7.42 (m, 3H), 7.33 (m, 2H), 6.74 (m, 1H), 6.27 (m, 1H), 3.41 (m, 2H), 1.93 (m, 1H), 1.23 (t, J=7.3 Hz, 3H), 0.75 (d, J=6.2 Hz, 4H); MS (ESI) m/z: 564.1 (M+H+).

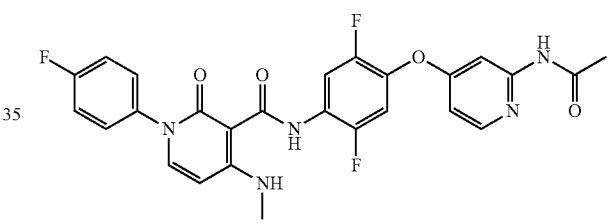

Example 7

A mixture of 1-(4-fluorophenyl)-4-iodo-2-oxo-1,2-dihydropyridine-3-carbonyl chloride (135 mg, 0.358 mmol, see: Example 6), Example A5 (100 mg, 0.358 mmol) and DIEA (47 mg, 0.36 mmol) in THF (5 mL) was stirred at RT overnight. The mixture was concentrated to afford crude 1-(4-fluoro-phenyl)-4-iodo-2-oxo-1,2-dihydro-pyridine-3-carboxylic acid [4-(2-acetylamino-pyridin-4-yloxy)-2,5-difluoro-phenyl]-amide (180 mg, 81.1% yield), which was used without further purification.

A methanolic solution of methylamine (10 mL) was added to 1-(4-fluoro-phenyl)-4-iodo-2-oxo-1,2-dihydro-pyridine-3-carboxylic acid [4-(2-acetylamino-pyridin-4-yloxy)-2,5-difluoro-phenyl]-amide (90 mg, 0.145 mmol) and the resultant mixture was stirred at 80° C. for 3 h. The mixture was concentrated to dryness and the crude product was recrystallized from MeOH to afford N-(4-((2-acetamidopyridin-4-yl)oxy)-2,5-difluorophenyl)-1-(4-fluorophenyl)-4-(methylamino)-2-oxo-1,2-dihydropyridine-3-carboxamide (65 mg, 85.5% yield). $^1$H NMR (400 MHz, DMSO-$d_6$): δ 13.21 (s, 1H), 10.57 (s, 1H), 10.34 (m, 1H), 8.47 (dd, J=13.0, 7.2 Hz, 1H), 8.17 (d, J=5.8 Hz, 1H), 7.72 (d, J=7.8 Hz, 1H), 7.65 (s, 1H), 7.55-7.42 (m, 3H), 7.33 (m, 2H), 6.69 (d, J=5.9 Hz, 1H), 6.24 (d, J=7.9 Hz, 1H), 3.01 (d, J=5.0 Hz, 3H), 2.02 (s, 3H); MS (ESI) m/z: 524.01 (M+H+).

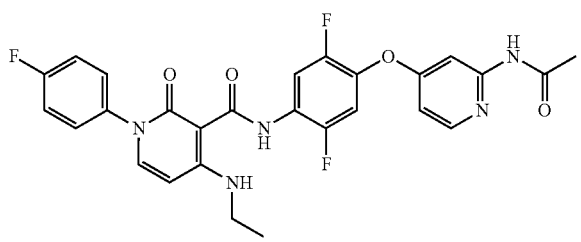

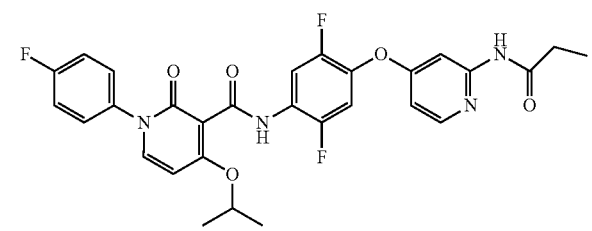

Example 8

Using the procedure of Example 7, 1-(4-fluoro-phenyl)-4-iodo-2-oxo-1,2-dihydro-pyridine-3-carboxylic acid [4-(2-acetylamino-pyridin-4-yloxy)-2,5-difluoro-phenyl]-amide (90 mg, 0.145 mmol) and a methanolic solution of ethylamine (10 mL) were combined to afford N-(4-((2-acetamidopyridin-4-yl)oxy)-2,5-difluorophenyl)-4-(ethylamino)-1-(4-fluorophenyl)-2-oxo-1,2-dihydropyridine-3-carboxamide (60 mg, 76.9% yield). $^1$H NMR (400 MHz, DMSO-$d_6$): δ 13.23 (s, 1H), 10.58 (s, 1H), 10.49 (m, 1H), 8.47 (dd, J=12.9, 7.2 Hz, 1H), 8.18 (d, J=5.8 Hz, 1H), 7.70 (d, J=7.9 Hz, 1H), 7.65 (m, 1H), 7.52 (dd, J=11.2, 7.4 Hz, 1H), 7.47 (m, 2H), 7.34 (m, 2H), 6.70 (dd, J=5.8, 2.5 Hz, 1H), 6.28 (d, J=7.9 Hz, 1H), 3.42 (m, 2H), 2.03 (s, 3H), 1.24 (t, J=7.2 Hz, 3H); MS (ESI) m/z: 538.0 (M+H$^+$).

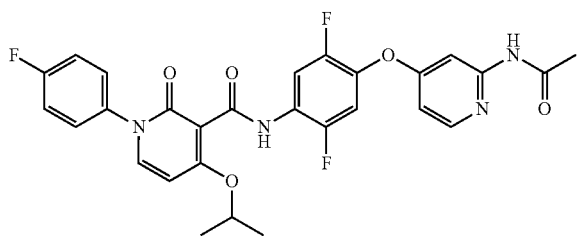 [SMILES: CC(=O)Nc1cc(Oc2cc(F)c(NC(=O)c3c(OC(C)C)ccn(-c4ccc(F)cc4)c3=O)cc2F)ccn1]

Example 9

A mixture of Example 1 (0.400 g, 0.743 mmol) and K$_2$CO$_3$ (0.400 g, 2.89 mmol) in isopropanol (10 mL) was heated at 120° C. for 1 h with microwave irradiation. The solids were removed by filtration and washed with THF. The filtrate was concentrated to dryness. The residue was stirred in water (15 mL) and the remaining solids were collected and crystallized from MeCN to provide N-(4-((2-acetamidopyridin-4-yl)oxy)-2,5-difluorophenyl)-1-(4-fluorophenyl)-4-isopropoxy-2-oxo-1,2-dihydropyridine-3-carboxamide, (0.295 g, 71.9% yield) as white solid. $^1$H NMR (400 MHz, DMSO-$d_6$): δ 11.03 (s, 1H), 10.58 (s, 1H), 8.29 (dd, J=12.6, 7.2 Hz, 1H), 8.18 (d, J=5.7 Hz, 1H), 7.87 (d, J=7.8 Hz, 1H), 7.67 (s, 1H), 7.50-7.49 (m, 3H), 7.35 (t, J=8.7 Hz, 2H), 6.71 (dd, J=5.7, 2.4 Hz, 1H), 6.55 (d, J=7.9 Hz, 1H), 4.85 (m, 1H), 2.03 (s, 3H), 1.31 (d, J=6.0 Hz, 6H); MS (ESI) m/z: 553.1 (M+H$^+$).

Example 10

A mixture of N-(4-((2-chloropyridin-4-yl)oxy)-2,5-difluorophenyl)-4-ethoxy-1-(4-fluorophenyl)-2-oxo-1,2-dihydropyridine-3-carboxamide (0.250 g, 0.485 mmol, see: Example 1) and K$_2$CO$_3$ (0.250 g, 1.809 mmol) in isopropanol (10 mL) was heated at 120° C. for 40 min with microwave irradiation. The reaction mixture was concentrated to dryness, was stirred in water (10 mL), filtered, washed, and dried in vacuo to provide N-(4-((2-chloropyridin-4-yl)oxy)-2,5-difluorophenyl)-1-(4-fluorophenyl)-4-isopropoxy-2-oxo-1,2-dihydropyridine-3-carboxamide (190 mg, 74.0% yield) as white solid. $^1$H NMR (400 MHz, DMSO-$d_6$): δ 11.05 (s, 1H), 8.31 (m, 2H), 7.87 (d, J=7.8 Hz, 1H), 7.51-7.48 (m, 3H), 7.36 (t, J=8.7 Hz, 2H), 7.17 (d, J=2.3 Hz, 1H), 7.04 (dd, J=5.8, 2.3 Hz, 1H), 6.55 (d, J=8.0 Hz, 1H), 4.85 (m, 1H), 1.31 (d, J=6.0 Hz, 6H); MS (ESI) m/z: 530.1 (M+H$^+$).

N-(4-((2-Chloropyridin-4-yl)oxy)-2,5-difluorophenyl)-1-(4-fluorophenyl)-4-isopropoxy-2-oxo-1,2-dihydropyridine-3-carboxamide (180 mg, 0.340 mmol), Cs$_2$CO$_3$ (400 mg, 1.228 mmol), propionamide (200 mg, 2.74 mmol) and Xantphos (20 mg, 0.035 mmol) were combined in dioxane (10 mL), sparged with argon under sonication, treated with Pd$_2$(dba)$_3$ (15 mg, 0.016 mmol) and heated to 90° C. overnight. The solids were collected by filtration and washed with DCM and MeCN. The filtrate was evaporated and the residue purified by silica gel chromatography (0-100% EtOAc/DCM) to provide N-(2,5-difluoro-4-((2-propionamidopyridin-4-yl)oxy)phenyl)-1-(4-fluorophenyl)-4-isopropoxy-2-oxo-1,2-dihydropyridine-3-carboxamide (95 mg, 49.4% yield) as a white solid. $^1$H NMR (400 MHz, DMSO-$d_6$): δ 11.05 (s, 1H), 10.52 (s, 1H), 8.30 (dd, J=12.6, 7.2 Hz, 1H), 8.18 (d, J=5.7 Hz, 1H), 7.87 (d, J=7.9 Hz, 1H), 7.68 (d, J=2.4 Hz, 1H), 7.51-7.48 (m, 3H), 7.35 (t, J=8.7 Hz, 2H), 6.72 (dd, J=5.7, 2.4 Hz, 1H), 6.55 (d, J=8.0 Hz, 1H); 4.85 (m, 1H), 2.34 (q, J=7.5 Hz, 2H), 1.31 (d, J=6.0 Hz, 6H), 0.99 (t, J=7.5 Hz, 3H); MS (ESI) m/z: 567.1 (M+H$^+$).

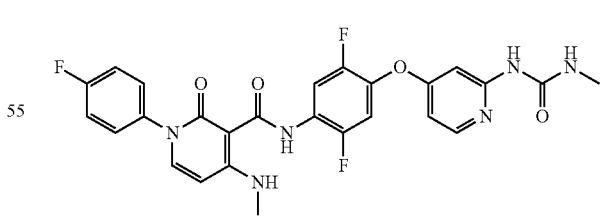

Example 11

A mixture of Example 1 (1.00 g, 1.86 mmol) and K$_2$CO$_3$ (1.000 g, 7.24 mmol) in EtOH (4 mL) was heated at 120° C. under microwave irradiation for 1 h. The reaction mixture was filtered, washed with EtOH and the filtrate was evaporated to dryness. The crude was stirred in water (15 mL) for a few minutes and collected by filtration. The residue was further purified by successive crystallization from MeOH and MeCN to provide N-(4-((2-aminopyridin-4-yl)oxy)-2,5-difluorophenyl)-4-ethoxy-1-(4-fluorophenyl)-2-oxo-1,2-dihydropyridine-3-carboxamide (350 mg, 38.0% yield) as a white solid. MS (ESI) m/z: 497.1 (M+H$^+$).

N-(4-((2-Aminopyridin-4-yl)oxy)-2,5-difluorophenyl)-4-ethoxy-1-(4-fluorophenyl)-2-oxo-1,2-dihydropyridine-3-carboxamide (0.12 g, 0.24 mmol) was dissolved in pyridine (2 mL), treated with isopropenyl chloroformate (0.030 mL, 0.27 mmol), and stirred at RT overnight. The solution was concentrated to obtain crude prop-1-en-2-yl (4-(4-(4-ethoxy-1-(4-fluorophenyl)-2-oxo-1,2-dihydropyridine-3-carboxamido)-2,5-difluorophenoxy)pyridin-2-yl)carbamate which was used for the next reaction (assuming 100% yield).

Prop-1-en-2-yl (4-(4-(4-ethoxy-1-(4-fluorophenyl)-2-oxo-1,2-dihydropyridine-3-carboxamido)-2,5-difluorophenoxy)pyridin-2-yl)carbamate (0.14 g, 0.24 mmol) was treated with a solution of N-methylamine (2.0 M in THF, 4 mL, 8 mmol) and N-methylpyrrolidine (0.021 g, 0.24 mmol), and was stirred at RT for 3 h. The solid was collected by filtration and further purified by silica gel chromatography (EtOAc). The purified residue was treated with MeCN/H$_2$O (1:1, 4 mL), frozen and lyophilized to obtain 1-(4-(2,5-difluoro-4-(1-(4-fluorophenyl)-4-(methylamino)-2-oxo-1,2-dihydropyridine-3-carboxamido)phenoxy)pyridin-2-yl)-3-methylurea (23 mg, 18% yield) as an off-white powder. $^1$H NMR (400 MHz, DMSO-d$_6$): δ 13.21 (s, 1H), 10.35 (d, J=6.0 Hz, 1H), 9.13 (s, 1H), 8.48 (dd, J=12.9, 7.2 Hz, 1H), 8.06 (d, J=5.9 Hz, 1H), 7.83 (s, 1H), 7.72 (d, J=7.8 Hz, 1H), 7.48 (m, 3H), 7.34 (t, J=8.5 Hz, 2H), 6.92 (s, 1H), 6.57 (dd, J=6.0, 2.4 Hz, 1H), 6.24 (d, J=7.9 Hz, 1H), 3.01 (d, J=5.0 Hz, 3H), 2.66 (d, J=4.6 Hz, 3H); MS (ESI) m/z: 539.2 (M+H+).

(0.48 g, 82% yield). $^1$H NMR (400 MHz, DMSO-d$_6$): δ 11.22 (s, 1H), 8.54 (d, J=7.8 Hz, 1H), 8.29 (d, J=5.8 Hz, 1H), 7.92 (d, J=7.8 Hz, 1H), 7.58 (d, J=11.0 Hz, 1H), 7.48 (dd, J=8.7, 4.9 Hz, 2H), 7.36 (t, J=8.7 Hz, 2H), 7.11 (d, J=2.3 Hz, 1H), 6.98 (dd, J=5.7, 2.3 Hz, 1H), 6.55 (d, J=7.9 Hz, 1H), 4.28 (q, J=7.0 Hz, 2H), 1.33 (t, J=7.0 Hz, 3H); MS (ESI) m/z: 532.1 (M+H$^+$).

N-(5-chloro-4-((2-chloropyridin-4-yl)oxy)-2-fluorophenyl)-4-ethoxy-1-(4-fluorophenyl)-2-oxo-1,2-dihydropyridine-3-carboxamide (0.05 g, 0.094 mmol) was combined with acetamide (8 mg, 0.14 mmol), Cs$_2$CO$_3$ (0.05 g, 0.14 mmol) and Xantphos (6 mg, 0.010 mmol) in dioxane (2 mL) and the mixture sparged with argon for several minutes. Pd$_2$(dba)$_3$ (5 mg, 0.005 mmol) was added and the mixture was sparged again with argon. The reaction vessel was sealed and heated at 100° C. overnight. The cooled reaction mixture was diluted with brine and extracted with EtOAc (2×). The organics were dried over Na$_2$SO$_4$, filtered and concentrated in vacuo. The crude was purified by silica gel chromatography (50-100% EtOAc/hexanes). The purified residue was treated with CH$_3$CN:H$_2$O (1:1, 2 mL), frozen and lyophilized to obtain N-(4-((2-acetamidopyridin-4-yl)oxy)-5-chloro-2-fluorophenyl)-4-ethoxy-1-(4-fluorophenyl)-2-oxo-1,2-dihydropyridine-3-carboxamide (27 mg, 50.5% yield). $^1$H NMR (400 MHz, DMSO-d$_6$): δ 11.19 (s, 1H), 10.57 (s, 1H), 8.50 (d, J=7.9 Hz, 1H), 8.17 (d, J=5.7 Hz, 1H), 7.92 (d, J=7.8 Hz, 1H), 7.61 (br s, 1H), 7.49 (m, 3H), 7.36 (t, J=8.7 Hz, 2H), 6.65 (dd, J=5.7, 2.4 Hz, 1H), 6.55 (d, J=7.9 Hz, 1H), 4.28 (q, J=7.0 Hz, 2H), 2.03 (s, 3H), 1.34 (t, J=7.0 Hz, 3H); MS (ESI) m/z: 555.1 (M+H$^+$).

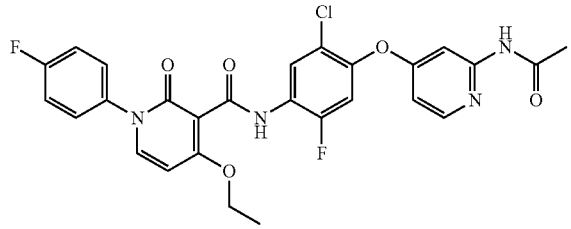

Example 12

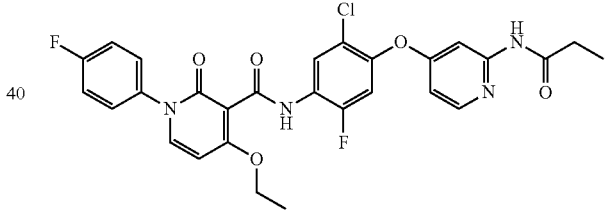

Example 13

Example B1 (0.50 g, 1.80 mmol) was combined with thionyl chloride (4 mL, 54.8 mmol) under argon and heated to 60° C. for 1 h. The mixture was concentrated to dryness, then treated with anhydrous toluene and concentrated to dryness. This process was repeated twice more to afford crude 4-ethoxy-1-(4-fluorophenyl)-2-oxo-1,2-dihydropyridine-3-carbonyl chloride, which was used without further purification (assuming 100% yield). A solution of Example A6 (0.30 g, 1.1 mmol) and triethylamine (0.31 mL, 2.2 mmol) in DCM (3 mL), under argon was added to a suspension of crude 4-ethoxy-1-(4-fluorophenyl)-2-oxo-1,2-dihydropyridine-3-carbonyl chloride (0.52 g, 1.76 mmol) in DCM (2 mL) cooled in an ice-water bath. The purple suspension was stirred at 0° C. for 30 min, then warmed to RT and stirred overnight. The mixture was concentrated in vacuo and purified by silica gel chromatography (EtOAc/hexanes) to obtain N-(5-chloro-4-((2-chloropyridin-4-yl)oxy)-2-fluorophenyl)-4-ethoxy-1-(4-fluorophenyl)-2-oxo-1,2-dihydropyridine-3-carboxamide Using the procedure of Example 12, N-(5-chloro-4-((2-chloropyridin-4-yl)oxy)-2-fluorophenyl)-4-ethoxy-1-(4-fluorophenyl)-2-oxo-1,2-dihydropyridine-3-carboxamide (0.05 g, 0.094 mmol), propionamide (10 mg, 0.14 mmol), Cs$_2$CO$_3$ (0.05 g, 0.14 mmol), Xantphos (6 mg, 0.010 mmol), Pd$_2$(dba)$_3$ (5 mg, 0.005 mmol) and dioxane (2 mL) were combined to obtain N-(5-chloro-2-fluoro-4-((2-propionamidopyridin-4-yl)oxy)phenyl)-4-ethoxy-1-(4-fluorophenyl)-2-oxo-1,2-dihydropyridine-3-carboxamide (9 mg, 16% yield). $^1$H NMR (400 MHz, DMSO-d$_6$): δ 11.16 (s, 1H), 10.46 (s, 1H), 8.46 (d, J=7.8 Hz, 1H), 8.13 (d, J=5.7 Hz, 1H), 7.87 (d, J=7.8 Hz, 1H), 7.57 (d, J=2.4 Hz, 1H), 7.45 (m, 3H), 7.31 (t, J=8.7 Hz, 2H), 6.62 (dd, J=5.7, 2.4 Hz, 1H), 6.50 (d, J=7.9 Hz, 1H), 4.23 (q, J=7.0 Hz, 2H), 2.28 (q, J=7.5 Hz, 2H), 1.29 (t, J=7.0 Hz, 3H), 0.95 (t, J=7.5 Hz, 3H); MS (ESI) m/z: 569.1 (M+H$^+$).

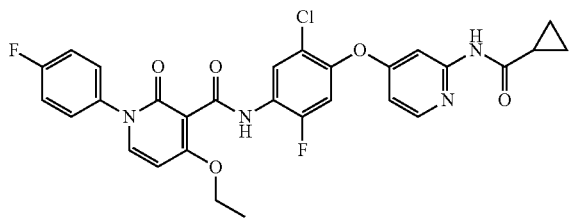 [SMILES: CCOc1ccn(-c2ccc(F)cc2)c(=O)c1C(=O)Nc1cc(Cl)c(Oc2ccnc(NC(=O)C3CC3)c2)cc1F]

Example 14

Using the procedure of Example 12, N-(5-chloro-4-((2-chloropyridin-4-yl)oxy)-2-fluorophenyl)-4-ethoxy-1-(4-fluorophenyl)-2-oxo-1,2-dihydropyridine-3-carboxamide (0.05 g, 0.094 mmol), cyclopropancarboxamide (12 mg, 0.14 mmol), Cs$_2$CO$_3$ (0.05 g, 0.14 mmol), Xantphos (6 mg, 0.010 mmol), Pd$_2$(dba)$_3$ (5 mg, 0.005 mmol) and dioxane (2 mL) were combined to obtain N-(5-chloro-4-(2-(cyclopropanecarboxamido)pyridin-4-yl)oxy)-2-fluorophenyl)-4-ethoxy-1-(4-fluorophenyl)-2-oxo-1,2-dihydropyridine-3-carboxamide (27 mg, 48.4% yield). $^1$H NMR (400 MHz, DMSO-d$_6$): δ 11.20 (s, 1H), 10.88 (s, 1H), 8.50 (d, J=7.8 Hz, 1H), 8.19 (d, J=5.7 Hz, 1H), 7.92 (d, J=7.8 Hz, 1H), 7.59 (d, J=2.4 Hz, 1H), 7.50 (m, 3H), 7.36 (t, J=8.7 Hz, 2H), 6.68 (dd, J=5.7, 2.4 Hz, 1H), 6.55 (d, J=7.9 Hz, 1H), 4.28 (q, J=7.0 Hz, 2H), 1.95 (m, 1H), 1.33 (t, J=7.0 Hz, 3H), 0.76 (t, J=5.9 Hz, 4H); MS (ESI) m/z: 581.1 (M+H$^+$).

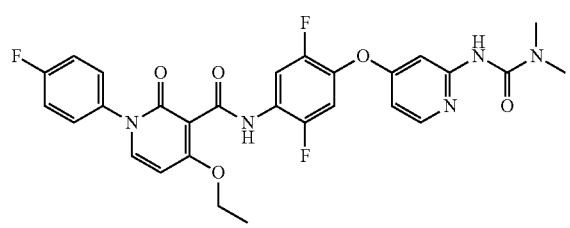

Example 15

Using the procedure of Example 4, N-(4-((2-chloropyridin-4-yl)oxy)-2,5-difluorophenyl)-4-ethoxy-1-(4-fluorophenyl)-2-oxo-1,2-dihydropyridine-3-carboxamide (0.100 g, 0.194 mmol), N,N-dimethylurea (0.102 g, 1.163 mmol), Cs$_2$CO$_3$ (0.158 g, 0.485 mmol), Xantphos (0.034 g, 0.058 mmol), Pd$_2$(dba)$_3$ (0.023 g, 0.025 mmol), and dioxane (5 mL) were combined to afford N-(4-((2-(3,3-dimethylureido)pyridin-4-yl)oxy)-2,5-difluorophenyl)-4-ethoxy-1-(4-fluorophenyl)-2-oxo-1,2-dihydropyridine-3-carboxamide (40 mg, 36.4% yield) as a white solid. $^1$H NMR (400 MHz, DMSO-d$_6$): δ 11.19 (s, 1H), 8.92 (s, 1H), 8.31 (dd, J=12.6, 7.2 Hz, 1H), 8.10 (d, J=5.7 Hz, 1H), 7.92 (d, J=7.8 Hz, 1H), 7.52-7.46 (m, 3H), 7.41-7.33 (m, 3H), 6.62 (dd, J=5.7, 2.4 Hz, 1H), 6.55 (d, J=7.9 Hz, 1H), 4.28 (q, J=7.0 Hz, 2H), 2.87 (s, 6H), 1.33 (t, J=7.0 Hz, 3H); MS (ESI) m/z: 568.2 (M+H+).

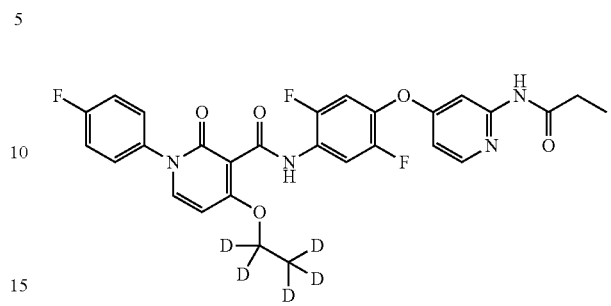

Example 16

A suspension of NaH (60% in mineral oil) (0.073 g, 1.824 mmol) in THF (5 mL) was treated slowly with ethanol-d$_6$ (5 g, 96 mmol) and stirred until a clear solution resulted. Example 2 (0.252 g, 0.456 mmol) was added and the mixture was stirred at RT for 90 min. The reaction was diluted with saturated NH$_4$Cl and the resultant precipitate was collected by filtration, and rinsed with H$_2$O and MeCN. Additional solids precipitated from the filtrate. These were also collected by filtration, and rinsed with H$_2$O and MeCN. The two crops were dried in the vacuum oven and combined to provide N-(2,5-difluoro-4-((2-propionamidopyridin-4-yl)oxy)phenyl)-4-(ethoxy-d5)-1-(4-fluorophenyl)-2-oxo-1,2-dihydropyridine-3-carboxamide (213 mg, 84% yield). $^1$H NMR (400 MHz, DMSO-d$_6$): δ 11.22 (s, 1H), 10.52 (s, 1H), 8.33 (dd, J=12.6, 7.2 Hz, 1H), 8.18 (d, J=5.7 Hz, 1H), 7.92 (d, J=7.9 Hz, 1H), 7.68 (d, J=2.4 Hz, 1H), 7.50-7.49 (m, 3H), 7.36 (t, J=8.7 Hz, 2H), 6.72 (dd, J=5.7, 2.4 Hz, 1H), 6.55 (d, J=7.9 Hz, 1H), 2.33 (q, J=7.5 Hz, 2H), 0.99 (t, J=7.4 Hz, 3H); MS (ESI) m/z: 558.2 (M+H+).

Biological Data c-MET Kinase Assay

Activity of c-MET kinase (Seq. ID No. 2) was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 μl) contained c-MET (c-MET residues: 956-1390, from Invitrogen, catalogue #PV3143, 6 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) in 90 mM Tris buffer containing 0.25 mM DTT, 0.2% octylglucoside and 1% DMSO, pH 7.5. Test compounds were incubated with c-MET (Seq. ID No. 2) and other reaction reagents at 22° C. for 0.5 h before ATP (100 μM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

c-MET Kinase (Seq ID No. 2)

MSYYHHHHHHDYDIPTTENLYFQGAMLVPRGSPWIPFTMKKRKQIKDLGSELV

RYDARVHTPHLDRLVSARSVSPTTEMVSNESVDYRATFPEDQFPNSSQNGSCRQVQYPLT

DMSPILTSGDSDISSPLLQNTVHIDLSALNPELVQAVQHVVIGPSSLIVHFNEVIGRGHFGCV

YHGTLLDNDGKKIHCAVKSLNRITDIGEVSQFLTEGIIMKDFSHPNVLSLLGICLRSEGSPLV

VLPYMKHGDLRNFIRNETHNPTVKDLIGFGLQVAKGMKYLASKKFVHRDLAARNCMLDE

KFTVKVADFGLARDMYDKEYYSVHNKTGAKLPVKWMALESLQTQKFTTKSDVWSFGVL

LWELMTRGAPPYPDVNTFDITVYLLQGRRLLQPEYCPDPLYEVMLKCWHPKAEMRPSFSE

LVSRISAIFSTFIGEHYVHVNATYVNVKCVAPYPSLLSSEDNADDEVDTRPASFWETS.

c-KIT kinase Assay

Activity of c-KIT kinase (Seq. ID No. 1) was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 µl) contained c-KIT (cKIT residues T544-V976, from ProQinase, 5.4 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 1% DMSO, pH 7.5. Test compounds were incubated with c-KIT (Seq. ID No. 1) and other reaction reagents at 22° C. for less than 2 min before ATP (200 µM) was added to start the reaction. The absorption at 340 nm was monitored continuously for 0.5 hours at 30° C. on Polarstar Optima plate reader (BMG). The reaction rate was calculated using the 0 to 0.5 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

KDR Kinase Assay

Assay K1

The activity of KDR kinase was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 µl) contained KDR (Seq ID No. 3, 1.5 nM to 7.1 nM, nominal concentration), polyE4Y (1 mg/mL), pyruvate kinase (3.5 units), lactate dehydrogenase (5.5 units), phosphoenolpyruvate (1 mM), and NADH (0.28 mM) in 60 mM Tris buffer containing 0.13% octyl-glucoside, 13 mM MgCl$_2$, 6.8 mM DTT, test compound, and 3.5% DMSO at pH 7.5. The reaction was initiated by adding ATP (0.2 mM, final concentration). The absorption at 340 nm was continuously monitored for 3 h at 30° C. on a Polarstar Optima plate reader (BMG) or instrument of similar capacity. The reaction rate was calculated using the 1 h to 2 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

Assay K2

KDR kinase assay K2 is the same as for assay K1 except that (1) a nominal concentration of 2.1 nM of enzyme was c-KIT with N-terminal GST fusion (Seq ID No. 1)

LGYWKIKGLVQPTRLLLEYLEEKYEEHLYERDEGDKWRNKKFELGLEFPNLPY

YIDGDVKLTQSMAIIRYIADKHNMLGGCPKERAEISMLEGAVDIRYGVSRIAYSKDFETLK

VDFLSKLPEMLKMFEDRLCHKTYLNGDHVTHPDFMLYDALDVVLYMDPMCLDAFPKLV

CFKKRIEAIPQIDKYLKSSKYIWPLQGWQATFGGGDHPPKSDLVPRHNQTSLYKKAGSAAA

VLEENLYFQGTYKYLQKPMYEVQWKVVEEINGNNYVYIDPTQLPYDHKWEFPRNRLSFG

KTLGAGAFGKVVEATAYGLIKSDAAMTVAVKMLKPSAHLTEREALMSELKVLSYLGNH

MNIVNLLGACTIGGPTLVITEYCCYGDLLNFLRRKRDSFICSKQEDHAEAALYKNLLHSKE

SSCSDSTNEYMDMKPGVSYVVPTKADKRRSVRIGSYIERDVTPAIMEDDELALDLEDLLSF

SYQVAKGMAFLASKNCIHRDLAARNILLTHGRITKICDFGLARDIKNDSNYVVKGNARLPV

KWMAPESIFNCVYTFESDVWSYGIFLWELFSLGSSPYPGMPVDSKFYKMIKEGFRMLSPEH

APAEMYDIMKTCWDADPLKRPTFKQIVQLIEKQISESTNHIYSNLANCSPNRQKPVVDHSV

RINSVGSTASSSQPLLVHDDV.

employed (2) the reaction was pre-incubated with test compound at 30° C. for 2 h prior to initiation with ATP and (3) 1.0 mM ATP (final concentration) was used to initiate the reaction.

Assay K3

KDR kinase assay K3 is the same as for assay K1 except that (1) a nominal concentration of 1.1 nM of enzyme was employed, (2) the buffer components per 100 μl reaction mixture were as follows: 75 mM Tris buffer containing 0.066% octyl-glucoside, 17 mM MgCl$_2$, and 1% DMSO at pH 7.5, (3) the final concentration of DTT was 0.66 mM, (4) the reaction was pre-incubated with test compound at 30° C. for 1 h prior to initiation with ATP, and (5) 1.0 mM ATP (final concentration) was used to initiate the reaction.

```
KDR protein sequence used for screening
                                                      (Seq. ID No. 3)
DPDELPLDEHCERLPYDASKWEFPRDRLKLGKPLGRGAFGQVIEADAFGIDKTATCRTVAVKML

KEGATHSEHRALMSELKILIHIGHHLNVVNLLGACTKPGGPLMVIVEFCKFGNLSTYLRSKRNEF

VPYKVAPEDLYKDFLTLEHLICYSFQVAKGMEFLASRKCIHRDLAARNILLSEKNVVKICDFGLA

RDIYKDPDYVRKGDARLPLKWMAPETIFDRVYTIQSDVWSFGVLLWEIFSLGASPYPGVKIDEEF

CRRLKEGTRMRAPDYTTPEMYQTMLDCWHGEPSQRPTFSELVEHLGNLLQANAQQD
```

FMS kinase Assay

Activity of FMS kinase was determined by following the production of ADP from the FMS kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophotometrically. The reaction mixture (100 μl) contained FMS (purchased from Millipore) (10 nM), polyE4Y (1 mg/ml), MgCl$_2$ (10 mM), pyruvate kinase (4 units), lactate dehydrogenase (0.7 units), phosphoenol pyruvate (1 mM), and NADH (0.28 mM) and ATP (500 μM) in 90 mM Tris buffer containing 0.2% octyl-glucoside and 1% DMSO, pH 7.5. Immediately, the inhibition reaction was started by mixing serial diluted test compound with the above reaction mixture. The absorption at 340 nm was monitored continuously for 4 hours at 30° C. on Synergy 2 plate reader. The reaction rate was calculated using the 3 to 4 h time frame. Percent inhibition was obtained by comparison of reaction rate with that of a control (i.e. in the absence of test compound). IC50 values were calculated from a series of percent inhibition values determined at a range of inhibitor concentrations using software routines as implemented in the GraphPad Prism software package.

```
cFMS protein sequence (Y538-end) used for
screening
                                    (Seq. ID No. 4)
Y KYKQKPKYQV RWKIIESYEG NSYTFIDPTQ LPYNEKWEFP

RNNLQFGKTL GAGAFGKVVE ATAFGLGKED AVLKVAVKML

KSTAHADEKE ALMSELKIMS HLGQHENIVN LLGACTHGGP

VLVITEYCCY GDLLNFLRRK AEAMLGPSLS PGQDPEGGVD

YKNIHLEKKY VRRDSGFSSQ GVDTYVEMRP VSTSSNDSFS

EQDLDKEDGR PLELRDLLHF SSQVAQGMAF LASKNCIHRD

VAARNVLLTN GHVAKIGDFG LARDIMNDSN YIVKGNARLP

VKWMAPESIF DCVYTVQSDV WSYGILLWEI FSLGLNPYPG

ILVNSKFYKL VKDGYQMAQP AFAPKNIYSI MQACWALEPT

HRPTFQQICS FLQEQAQEDR RERDYTNLPS SSRSGGSGSS

SSELEEESSS EHLTCCEQGD IAQPLLQPNN YQFC
```

EBC-1 Cell Culture

EBC-1 cells (catalog #JCRB0820) were obtained from the Japan Health Science Research Resources Bank, Osaka, Japan. Briefly, cells were grown in DMEM supplemented with 10% characterized fetal bovine serum (Invitrogen, Carlsbad, Calif.) at 37° C., 5% $CO_2$, 95% humidity. Cells were allowed to expand until reaching 70-95% confluency at which point they were subcultured or harvested for assay use.

EBC-1 Cell Proliferation Assay

A serial dilution of test compound was dispensed into a 96-well black clear bottom plate (Corning, Corning, N.Y.). For each cell line, five thousand cells were added per well in 200 μL complete growth medium. Plates were incubated for 67 hours at 37° C., 5% $CO_2$, 95% humidity. At the end of the incubation period 40 μL of a 440 μM solution of resazurin (Sigma, St. Louis, Mo.) in PBS was added to each well and incubated for an additional 5 hours at 37° C., 5% $CO_2$, 95% humidity. Plates were read on a Synergy2 reader (Biotek, Winooski, Vt.) using an excitation of 540 nM and an emission of 600 nM. Data was analyzed using Prism software (GraphPad, San Diego, Calif.) to calculate $IC_{50}$ values.

EBC-1 Phospho-MET ELISA

Fifteen thousand cells in DMEM supplemented with 0.5% characterized fetal bovine serum (FBS; Invitrogen, Carlsbad, Calif.) were added per well in a 96-well black clear bottom plate (Corning, Corning, N.Y.). Cells were then incubated overnight at 37 degrees Celsius, 5% $CO_2$, 95% humidity. A serial dilution of test compound was dispensed into another 96-well black clear bottom plate (Corning, Corning, N.Y.) containing DMEM supplemented with 0.5% FBS. Diluted compound was then added to plates containing cells and incubated for 6 hours at 37 degrees Celsius, 5% $CO_2$, 95% humidity. Cells were stimulated with 40 ng/mL HGF (R&D Systems, Minneapolis, Minn.) for 10 minutes, and then lysed. Phospho-MET in cell lysates was detected using the DuoSet IC Human Phospho-HGF R/c-MET ELISA (R&D Systems, Minneapolis, Minn.). Data was analyzed using Prism software (Graphpad, San Diego, Calif.) to calculate IC50 values.

MKN-45 Cell Culture

MKN-45 cells (catalog #JCRB0254) were obtained from the Japan Health Science Research Resources Bank, Osaka, Japan. Briefly, cells were grown in RPMI 1640 media supplemented with 10% characterized fetal bovine serum (Invitrogen, Carlsbad, Calif.) at 37° C., 5% CO2, 95% humidity. Cells were allowed to expand until reaching 70-95% confluency at which point they were subcultured or harvested for assay use.

MKN-45 Cell Proliferation Assay

A serial dilution of test compound was dispensed into a 96-well black clear bottom plate (Corning, Corning, N.Y.). Five thousand cells were added per well in 200 µL complete growth medium. Plates were incubated for 67 hours at 37° C., 5% $CO_2$, 95% humidity. At the end of the incubation period 40 µL of a 440 µM solution of resazurin (Sigma, St. Louis, Mo.) in PBS was added to each well and plates were incubated for an additional 5 h at 37° C., 5% $CO_2$, 95% humidity. Plates were read on a Synergy2 reader (Biotek, Winooski, Vt.) using an excitation of 540 nM and an emission of 600 nM. Data was analyzed using Prism software (GraphPad, San Diego, Calif.) to calculate $IC_{50}$ values.

MKN-45 Phospho-MET ELISA

Twenty-five thousand cells in RPMI-1640 supplemented with 10% characterized fetal bovine serum (Invitrogen, Carlsbad, Calif.) were added per well in a 96-well black clear bottom plate (Corning, Corning, N.Y.). Cells were then incubated overnight at 37 degrees Celsius, 5% $CO_2$, 95% humidity. Media was then aspirated and cells were washed with PBS. A serial dilution of test compound was dispensed into another 96-well black clear bottom plate (Corning, Corning, N.Y.) containing serum-free RPMI-1640. Compound was added to plates containing cells and incubated for 6 hours at 37 degrees Celsius, 5% $CO_2$, 95% humidity. Cells were stimulated with 40 ng/mL HGF (R&D Systems, Minneapolis, Minn.) for 10 minutes, and then lysed. Phospho-MET in cell lysates was detected using the DuoSet IC Human Phospho-HGF R/c-MET ELISA (R&D Systems, Minneapolis, Minn.). Data was analyzed using Prism software (Graphpad, San Diego, Calif.) to calculate IC50 values.

A549 Cell Culture

A549 cells (catalog #CCL-185) were obtained from the American Type Culture Collection (ATCC, Manassas, Va.). Briefly, cells were grown in DMEM supplemented with 10% characterized fetal bovine serum (Invitrogen, Carlsbad, Calif.) at 37 degrees Celsius, 5% CO2, 95% humidity. Cells were allowed to expand until reaching 70-95% confluency at which point they were subcultured or harvested for assay use.

A549 Cell Migration Assay

Forty thousand cells in DMEM supplemented with 10% characterized fetal bovine serum (FBS; Invitrogen, Carlsbad, Calif.) were added per well in a 96-well black clear bottom Oris Collagen-Coated cell migration plate containing cell seeding stoppers (Platypus Technologies, Madison, Wis.). Cells were then incubated overnight at 37 degrees Celsius, 5% $CO_2$, 95% humidity. Cell seeding stoppers were removed creating an area for cell migration in the center of each well of the plate. Media was replaced with DMEM supplemented with 0.5% FBS. A serial dilution of test compound was dispensed into another 96-well black clear bottom plate (Corning, Corning, N.Y.) containing DMEM supplemented with 0.5% FBS. Diluted compound was then added to plates containing cells and incubated for 4 hours at 37 degrees Celsius, 5% $CO_2$, 95% humidity. After 4 hours, 40 ng/mL HGF (R&D Systems, Minneapolis, Minn.) was added, and the cells were allowed to migrate for 48 h. After 48 h, media was removed, and cells were washed with serum-free DMEM media. Calcein-AM (Invitrogen, Carlsbad, Calif.) was added to the cells and incubated for 20 min to fluorescently label cells. Media was removed, and serum-free DMEM was added. A plate mask (Platypus Technologies, Madison, Wis.) that obscures each well except for the area for cell migration in the center of the well was attached to the bottom of the migration plate and fluorescence was detected using a fluorescent plate reader. Data was analyzed using Prism software (Graphpad, San Diego, Calif.) to calculate IC50 values.

Compounds of Formula I were found to exhibit inhibitory activity in one or more of the aforementioned assays when evaluated at concentrations ≤10 µM. In some embodiments, compounds of Formula I exhibit greater inhibitory activity against cMET than inhibition of cKIT, KDR, or FMS.

Compounds of the present invention unexpectedly afford selective or highly potent inhibitors of cMET kinase. As shown below, Example 1 and Example 2 of the present invention demonstrated an unexpected increased potency in cMET kinase inhibition assays when compared with the compound disclosed in WO 2008/058229 ("the '229 Compound") and further described in *J. Med. Chem.* (2009) 52: 1251-1254. Also shown below is Compound A, which is outside the scope of the present invention, which was synthesized and compared to Example 1 and Example 2.

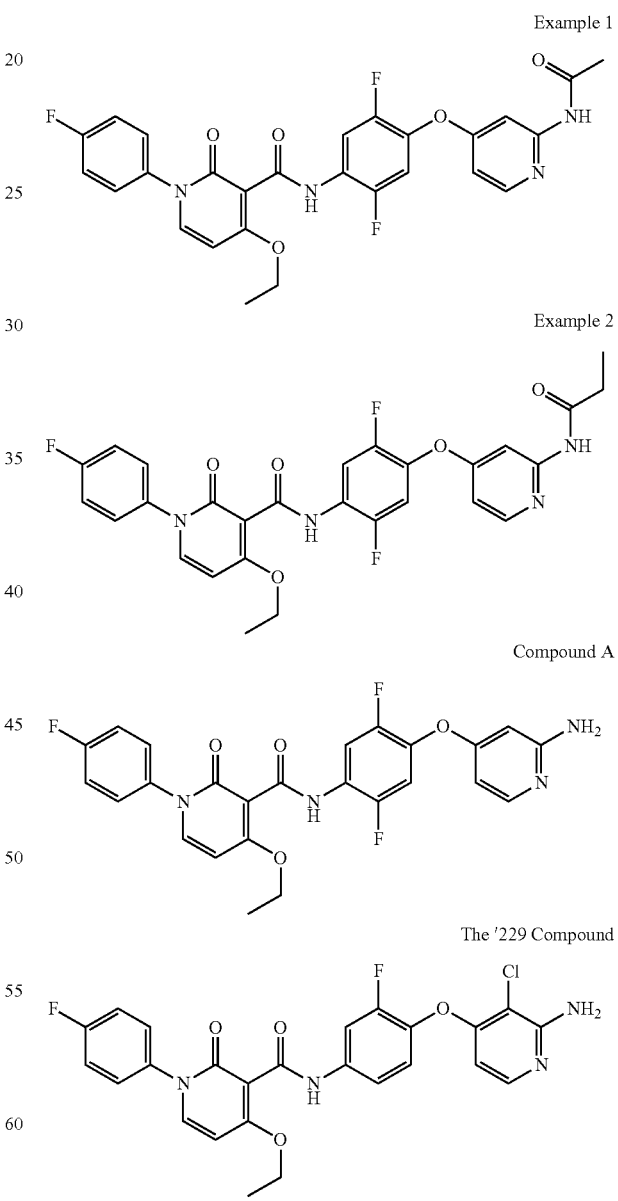

Example 1

Example 2

Compound A

The '229 Compound

Comparative biological data for Example 1 of the present invention, the '229 Compound, and Compound A are shown in Table 1.

TABLE 1

| | Fold potency decrease versus Example 1 | | | | | | | |
|---|---|---|---|---|---|---|---|---|
| | Col. 2 | Col. 3 | Col. 4 | Col. 5 | Col. 6 | Col. 7 | Col. 8 | Col. 9 |
| Compound | cMET WT | MET (D1246H) Mutant | MET (D1246N) Mutant | MET (Y1248C) Mutant | MET (Y1248H) Mutant | EBC-1 p-MET | MKN-45 p-MET | A549 MIG |
| Example 1 | 1 | 1 | 1 | 1 | 1 | 1 | 1 | 1 |
| The '229 Compound | 3.9 X | 8.5 X | 2 X | 3.8 X | 2.3 X | 22.5 X | 73.8 X | 2.4 X |
| Compound A | 2.4 X | 6.7 X | 4.4 X | 6 X | 2.6 X | 11.7 X | 18.8 X | 3.4 X |

Example 1 is 3.9× more potent than the '229 Compound in the WT MET biochemical assay (column 2), 2.3-8.5× more potent than the '229 Compound in the various oncogenic Mutant MET kinase biochemical assays (columns 3-6), 22.5× more potent than the '229 Compound in the EBC-1 cellular MET cancer cell assay (column 7), 73.8× more potent than the '229 Compound in the MKN-45 cellular MET cancer cell assay (column 8), and 2.4× more potent than the '229 Compound in the A549 HGF-stimulated MET-dependent migration assay (column 9).

The three structural differences between Example 1 and the '229 Compound are 1) the presence of chlorine at the 3-position of the pyridine ring in the '229 Compound and its absence in Example 1; 2) the presence of a 2,5-di-fluoro substitution pattern in the central ring of Example 1, whereas the '229 Compound has only the 5-mono fluoro substituent; and 3) the presence of an aminoacyl moiety at the 2-position of the pyridine ring in Example 1 whereas the '229 Compound lacks the acyl residue, having a primary amino substituent. It is unexpected that these structural differences between Example 1 and the '229 Compound would account for the significant increases in MET kinase biochemical and whole cell potency of Example 1 over the '229 Compound.

Compound A, while not disclosed in prior art, was made for comparison to Example 1. Compound A is outside the scope of the present invention and further demonstrates the unexpected potency of Example 1 to another closely related compound. Example 1 is unexpectedly more potent than Compound A as a MET kinase inhibitor both in biochemical and cellular biological assays. Example 1 is 2.4× more potent than Compound A in the WT MET biochemical assay (column 2), 2.6-6.7× more potent than Compound A in the various oncogenic Mutant MET kinase biochemical assays (columns 3-6), 11.7× more potent than Compound A in the EBC-1 cellular MET cancer cell assay (column 7), 18.8× more potent than Compound A in the MKN-45 cellular MET cancer cell assay (column 8), and 3.4× more potent than Compound A in the A549 HGF-stimulated MET-dependent migration assay (column 9). The only structural difference between Example 1 and Compound A is the presence of an aminoacyl moiety at the 2-position of the pyridine ring in Example 1 whereas Compound A lacks the acyl residue, having a primary amino substituent. It is unexpected that this structural difference between Example 1 and Compound A would account for the significant increase in MET kinase potency of Example 1 over Compound A.

Comparative biological data for Example 2 of the present invention, the '229 Compound, and Compound A are shown in Table 2.

TABLE 2

| | Fold potency decrease versus Example 2 | | | | | | | |
|---|---|---|---|---|---|---|---|---|
| | Col. 2 | Col. 3 | Col. 4 | Col. 5 | Col. 6 | Col. 7 | Col. 8 | Col. 9 |
| Compound | cMET WT | MET (D1246H) Mutant | MET (D1246N) Mutant | MET (Y1248C) Mutant | MET (Y1248H) Mutant | EBC-1 p-MET | MKN-45 p-MET | A549 MIG |
| Example 2 | 1 | 1 | 1 | 1 | 1 | 1 | 1 | 1 |
| The '229 Compound | 4.4 X | 5.1 X | 2.5 X | 3.6 X | 15.7 X | 41.5 X | 73.7 X | 6.3 X |
| Compound A | 2.7 X | 4 X | 5.7 X | 5.7 X | 18.3 X | 21.5 X | 18.8 X | 8.9 X |

Example 2 is 4.4× more potent than the '229 Compound in the WT MET biochemical assay (column 2), 2.5-15.7× more potent than the '229 Compound in the various oncogenic Mutant MET kinase biochemical assays (columns 3-6), 41.5× more potent than the '229 Compound in the EBC-1 cellular MET cancer cell assay (column 7), 73.7× more potent than the '229 Compound in the MKN-45 cellular MET cancer cell assay (column 8), and 6.3× more potent than the '229 Compound in the A549 HGF-stimulated MET-dependent migration assay (column 9). The three structural differences between Example 2 and the '229 Compound are the same as for the comparison above between Example 1 and the '229 Compound: 1) the presence of chlorine at the 3-position of the pyridine ring in the '229 Compound and its absence in Example 2; 2) the presence of a 2,5-di-fluoro substitution pattern in the central ring of Example 2, whereas the '229 Compound has only the 5-mono fluoro substituent; and 3) the presence of an aminoacyl moiety at the 2-position of the pyridine ring in Example 2 whereas the '229 Compound lacks the acyl residue, having a primary amino substituent. It is unexpected that these structural differences between Example 2 and the '229 Compound would account for the significant increases in MET kinase potency of Example 2 over the '229 Compound.

Compound A, while apparently not disclosed in prior art, was made for comparison to Example 2 as was made above for comparison with Example 1. Compound A is outside the scope of the present invention and further demonstrates the unexpected potency of Example 2 to another closely related compound. Example 2 is unexpectedly more potent than Compound A as a MET kinase inhibitor both in biochemical and cellular biological assays. Example 2 is 2.7× more potent than Compound A in the WT MET biochemical assay (column 2), 4-18.3× more potent than Compound A in the various oncogenic Mutant MET kinase biochemical assays (columns 3-6), 21.5× more potent than Compound A in the EBC-1 cellular MET cancer cell assay (column 7), 18.8× more potent than Compound A in the MKN-45 cellular MET cancer cell assay (column 8), and 8.9× more potent than Compound A in the A549 HGF-stimulated MET-dependent migration assay (column 9). The only structural difference between Example 2 and Compound A is the presence of an aminoacyl moiety at the 2-position of the pyridine ring in Example 2 whereas Compound A lacks the acyl residue, having a primary amino substituent. It is unexpected that this structural difference between Example 2 and Compound A would account for the significant increase in MET kinase potency of Example 2 over Compound A.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of Formula I,

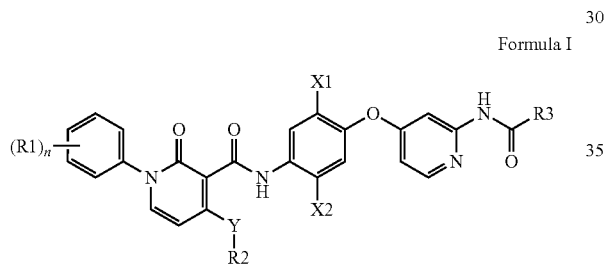

Formula I or a pharmaceutically acceptable salt, enantiomer, stereoisomer or tautomer thereof, wherein:

X1 is halogen;
X2 is halogen;
Y is O, —NH;
each R1 is individually and independently halogen or H;
each R2 is individually and independently C1-C6 alkyl, deuteroC1-C6alkyl wherein the alkyl moiety can be partially or fully deuterated, C3-C8 branched alkyl, deuteroC3-C8 branched alkyl wherein the alkyl moiety can be partially or fully deuterated, or C3-C8 cycloalkyl;
R3 is C1-C6 alkyl, C3-C8 branched alkyl, C3-C8 cycloalkyl, —NR6(R7), or —R4, wherein each alkyl, branched or cycloalkyl may be optionally substituted with cyano, C1-C6alkoxy, or hydroxy;
each R4 is independently and individually selected from the group consisting of

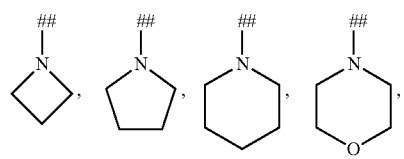

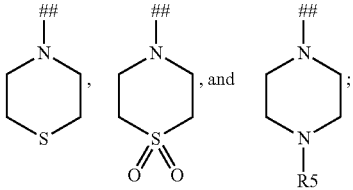

and wherein the symbol (##) is the point of attachment of the R4 moiety;
R5 is C1-C6 alkyl;
each R6 and R7 is individually and independently H, C1-C6 alkyl, or branched C3-C8 alkyl;
n is 0, 1, or 2.

2. The compound of claim 1, wherein the compound is a compound of Formula Ia,

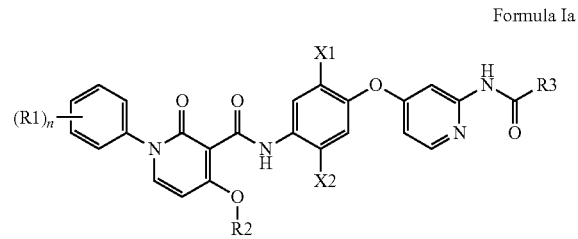

Formula Ia or a pharmaceutically acceptable salt, enantiomer, stereoisomer or tautomer thereof.

3. The compound of claim 2, wherein the compound is a compound of Formula Ib,

Formula Ib or a pharmaceutically acceptable salt, enantiomer stereoisomer or tautomer thereof.

4. The compound of claim 3, wherein the compound is a compound of Formula Ic,

Formula Ic or a pharmaceutically acceptable salt, enantiomer stereoisomer or tautomer thereof.

5. The compound of claim 4, wherein R3 is C1-C6 alkyl, C3-C8 branched alkyl, C3-C8 cycloalkyl or a pharmaceutically acceptable salt, enantiomer stereoisomer or tautomer thereof.

6. The compound of claim 4, wherein R3 is —NR6(R7) or R4, or a pharmaceutically acceptable salt, enantiomer stereoisomer or tautomer thereof.

7. A compound of any one of claims 1-6 wherein R1 is fluoro or H and n is 1.

8. A compound of claims any one of 1-7 wherein R2 is C1-C6 alkyl or C3-C8 branched alkyl.

9. The compound of claim 1, wherein the compound is a compound of Formula Id,

Formula Id or a pharmaceutically acceptable salt, enantiomer, stereoisomer or tautomer thereof.

10. The compound of claim 9, wherein the compound is a compound of Formula Ie,

Formula Ie or a pharmaceutically acceptable salt, enantiomer stereoisomer or tautomer thereof.

11. The compound of claim 10, wherein the compound is a compound of Formula If,

Formula If or a pharmaceutically acceptable salt, enantiomer stereoisomer or tautomer thereof.

12. The compound of claim 11, wherein R3 is C1-C6 alkyl, C3-C8 branched alkyl, C3-C8 cycloalkyl or a pharmaceutically acceptable salt, enantiomer stereoisomer or tautomer thereof.

13. The compound of claim 11, wherein R3 is —NR6(R7) or R4 or a pharmaceutically acceptable salt, enantiomer stereoisomer or tautomer thereof.

14. A compound of any one of claims 9-13 wherein R1 is fluoro or H and n is 1.

15. A compound of claims any one of 9-14 wherein R2 is C1-C6 alkyl or C3-C8 branched alkyl.

16. A compound selected from the group consisting of N-(4-((2-acetamidopyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-propionamidopyridin-4-yl)oxy)phenyl)-4-ethoxy-1-(4-fluorophenyl)-2-oxo-1,2-dihydropyridine-3-carboxamide, N-(4-(2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-pivalamidopyridin-4-yl)oxy)phenyl)-4-ethoxy-1-(4-fluorophenyl)-2-oxo-1,2-dihydropyridine-3-carboxamide, N-(2,5-difluoro-4-((2-isobutyramidopyridin-4-yl)oxy)phenyl)-4-ethoxy-1-(4-fluorophenyl)-2-oxo-1,2-dihydropyridine-3-carboxamide, N-(4-(2-(cyclopropanecarboxamido)pyridin-4-yl)oxy)-2,5-difluorophenyl)-4-(ethylamino)-1-(4-fluorophenyl)-2-oxo-1,2-dihydropyridine-3-carboxamide, N-(4-((2-acetamidopyridin-4-yl)oxy)-2,5-difluorophenyl)-1-(4-fluorophenyl)-4-(methylamino)-2-oxo-1,2-dihydropyridine-3-carboxamide, N-(4-((2-acetamidopyridin-4-yl)oxy)-2,5-difluorophenyl)-4-(ethylamino)-1-(4-fluorophenyl)-2-oxo-1,2-dihydropyridine-3-carboxamide, N-(4-((2-acetamidopyridin-4-yl)oxy)-2,5-difluorophenyl)-1-(4-fluorophenyl)-4-isopropoxy-2-oxo-1,2-dihydropyridine-3-carboxamide, N-(2,5-difluoro-4-((2-propionamidopyridin-4-yl)oxy)phenyl)-1-(4-fluorophenyl)-4-isopropoxy-2-oxo-1,2-dihydropyridine-3-carboxamide, 1-(4-(2,5-difluoro-4-(1-(4-fluorophenyl)-4-(methylamino)-2-oxo-1,2-dihydropyridine-3-carboxamido)phenoxy)pyridin-2-yl)-3-methylurea, N-(4-((2-acetamidopyridin-4-yl)oxy)-5-chloro-2-fluorophenyl)-4-ethoxy-1-(4-fluorophenyl)-2-oxo-1,2-dihydropyridine-3-carboxamide, N-(5-chloro-2-fluoro-4-((2-propionamidopyridin-4-yl)oxy)phenyl)-4-ethoxy-1-(4-fluorophenyl)-2-oxo-1,2-dihydropyridine-3-carboxamide, N-(5-chloro-4-((2-(cyclopropanecarboxamido)pyridin-4-yl)oxy)-2-fluorophenyl)-4-ethoxy-1-(4-fluorophenyl)-2-oxo-1,2-dihydropyridine-3-carboxamide, N-(4-((2-(3,3-dimethylureido)pyridin-4-yl)oxy)-2,5-difluorophenyl)-4-ethoxy-1-(4-fluorophenyl)-2-oxo-1,2-dihydropyridine-3-carboxamide, and N-(2,5-difluoro-4-((2-propionamidopyridin-4-yl)oxy)phenyl)-4-(ethoxy-d5)-1-(4-fluorophenyl)-2-oxo-1,2-dihydropyridine-3-carboxamide, or a pharmaceutically acceptable salt, or tautomer thereof.

17. The compound N-(4-((2-acetamidopyridin-4-yl)oxy)-2,5-difluorophenyl)-4-ethoxy-1-(4-fluorophenyl)-2-oxo-1,2-dihydropyridine-3-carboxamide, or a pharmaceutically acceptable salt, or tautomer thereof.

18. The compound N-(2,5-difluoro-4-((2-propionamidopyridin-4-yl)oxy)phenyl)-4-ethoxy-1-(4-fluorophenyl)-2-oxo-1,2-dihydropyridine-3-carboxamide, or a pharmaceutically acceptable salt, or tautomer thereof.

19. The compound N-(4-((2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide, or a pharmaceutically acceptable salt, or tautomer thereof.

20. The compound N-(4-((2-(3,3-dimethylureido)pyridin-4-yl)oxy)-2,5-difluorophenyl)-4-ethoxy-1-(4-fluorophenyl)-2-oxo-1,2-dihydropyridine-3-carboxamide, or a pharmaceutically acceptable salt, or tautomer thereof.

21. The compound N-(2,5-difluoro-4-((2-isobutyramidopyridin-4-yl)oxy)phenyl)-4-ethoxy-1-(4-fluorophenyl)-2-oxo-1,2-dihydropyridine-3-carboxamide, or a pharmaceutically acceptable salt, or tautomer thereof.

22. A pharmaceutical composition, comprising a compound of claim 1 and a pharmaceutically acceptable carrier.

23. The composition of claim 22, further comprising an additive selected from adjuvants, excipients, diluents, or stabilizers.

* * * * *